United States Patent
Romagnani et al.

(10) Patent No.: US 10,864,245 B2
(45) Date of Patent: Dec. 15, 2020

(54) ACTIVATION AND EXPANSION OF NKG2C+ NK CELLS

(71) Applicant: Deutsches Rheuma-Forschungszentrum Berlin, Berlin (DE)

(72) Inventors: Chiara Romagnani, Berlin (DE); Timo Rückert, Berlin (DE); Quirin Hammer, Berlin (DE)

(73) Assignee: DEUTSCHES RHEUMA-FORSCHUNGSZENTRUM BERLIN, Berlin (DE)

( * ) Notice: Subject to any disclaimer, the term of this patent is extended or adjusted under 35 U.S.C. 154(b) by 0 days.

(21) Appl. No.: 16/355,577

(22) Filed: Mar. 15, 2019

(65) Prior Publication Data
US 2019/0314445 A1  Oct. 17, 2019

(30) Foreign Application Priority Data
Mar. 16, 2018 (EP) ..................... 18162281

(51) Int. Cl.
| | |
|---|---|
| A61K 38/08 | (2019.01) |
| A61P 31/20 | (2006.01) |
| A61P 35/02 | (2006.01) |
| A61P 35/00 | (2006.01) |
| A61K 35/17 | (2015.01) |
| A61K 38/20 | (2006.01) |
| A61K 45/06 | (2006.01) |
| C12N 5/0783 | (2010.01) |

(52) U.S. Cl.
CPC .............. *A61K 38/08* (2013.01); *A61K 35/17* (2013.01); *A61K 38/20* (2013.01); *A61K 38/208* (2013.01); *A61K 38/2086* (2013.01); *A61K 45/06* (2013.01); *A61P 31/20* (2018.01); *A61P 35/00* (2018.01); *A61P 35/02* (2018.01); *C12N 5/0638* (2013.01)

(58) Field of Classification Search
CPC ........ A61K 38/08; A61K 35/17; A61K 38/20; A61K 38/208; A61K 38/2086; A61K 45/06; A61K 38/04; A61K 38/03; A61P 31/20; A61P 35/02; A61P 35/00; A61P 31/12; C12N 5/0638
See application file for complete search history.

(56) References Cited

U.S. PATENT DOCUMENTS

| | | | |
|---|---|---|---|
| 2003/0171280 A1* | 9/2003 | Soderstrom | C07K 14/47 424/184.1 |
| 2015/0361180 A1* | 12/2015 | Braud | G01N 33/56977 800/13 |
| 2018/0298404 A1* | 10/2018 | Frueh | C12Q 1/68 |
| 2019/0071502 A1* | 3/2019 | Weidanz | A61K 47/6849 |

FOREIGN PATENT DOCUMENTS

| | | | |
|---|---|---|---|
| WO | WO 03/011895 A2 | 2/2003 | |
| WO | WO-2018005559 A1 * | 1/2018 | ......... C12N 15/1037 |

OTHER PUBLICATIONS

Prod'homme V, Tomasec P, Cunningham C, Lemberg MK, Stanton RJ, McSharry BP, Wang EC, Cuff S, Martoglio B, Davison AJ, Braud VM, Wilkinson GW. Human cytomegalovirus UL40 signal peptide regulates cell surface expression of the NK cell ligands HLA-E and gpUL18. J Immunol. Mar. 15, 2012;188(6):2794-804. Epub Feb. 15, 2012.*
Beldi-Ferchiou A, Caillat-Zucman S. Control of NK Cell Activation by Immune Checkpoint Molecules. Int J Mol Sci. Oct. 12, 2017;18(10). pii: E2129.*
Foley B, Cooley S, Verneris MR, Curtsinger J, Luo X, Waller EK, Anasetti C, Weisdorf D, Miller JS. Human cytomegalovirus (CMV)-induced memory-like NKG2C(+) NK cells are transplantable and expand in vivo in response to recipient CMV antigen. J Immunol. Nov. 15, 2012;189(10):5082-8. Epub Oct. 17, 2012.*
Kuijpers TW, Baars PA, Dantin C, van den Burg M, van Lier RA, Roosnek E. Human NK cells can control CMV infection in the absence of T cells. Blood. Aug. 1, 2008;112(3):914-5.*
Kraemer T, Blasczyk R, Bade-Doeding C. HLA-E: a novel player for histocompatibility. J Immunol Res. 2014;2014:352160. Epub Oct. 20, 2014.*
Hoare HL, Sullivan LC, Clements CS, et. al. Subtle changes in peptide conformation profoundly affect recognition of the non-classical MHC class I molecule HLA-E by the CD94-NKG2 natural killer cell receptors. J Mol Biol. Apr. 11, 2008;377(5):1297-303. Epub Feb. 12, 2008.*
Adam, S., G. et al. 2006 "Cmv4, a New Locus Linked to the NK Cell Gene Complex, Controls Innate Resistance to Cytomegalovirus in Wild-Derived Mice", The Journal of Immunology, vol. 176, pp. 5478-5485.

(Continued)

*Primary Examiner* — Rachel B Gill
(74) *Attorney, Agent, or Firm* — Knobbe, Martens, Olson & Bear, LLP

(57) ABSTRACT

The invention relates to an isolated peptide for use as a medicament, wherein said peptide has 9 to 30 amino acids and comprises or consists of an amino acid sequence according to SEQ ID NO 1 (VMAPRTLXL), wherein X is an amino acid with a hydrophobic side chain (A, I, L, F, V, P, G), preferably V, L, I or F. The invention further relates to the peptide of the invention for use as a medicament to expand and/or activate NKG2C+ natural killer (NK) cells. The invention further relates to the peptide of the invention for use in the treatment and/or prevention of a medical condition associated with pathogenic cells expressing HLA-E and a peptide comprising an amino acid sequence according to SEQ ID NO 1 or 2. Additionally, the invention relates to a genetically modified virus encoding a peptide comprising or consisting of a polypeptide of the invention for use as a medicament to expand and/or activate NKG2C+ natural killer (NK) cells.

13 Claims, 24 Drawing Sheets

Specification includes a Sequence Listing.

(56) References Cited

OTHER PUBLICATIONS

Andreatta, M. et al., "Gapped Sequence Alignment Using Artificial Neural Networks: Application To The MHC Class I System", Bioinformatics, vol. 32, No. 4, pp. 511-517, 2016.
Arase, H. et al., "Direct Recognition of Cytomegalovirus by Activating and Inhibitory NK Cell Receptors", Science, vol. 296, pp. 1323-1327, 2002.
Beaulieu, A., M. et al., "The Transcription Factor Zbtb32 Controls The Proliferative Burst Of Virus-Specific Natural Killer Cells Responding To Infection", Nature Immunology, vol. 15, No. 6, pp. 546-555, 2014.
Beziat, V. et al., "CMV Drives Clonal Expansion of NKG2C1 NK Cells Expressing Self-Specific Kirs in Chronic Hepatitis Patients", European Journal of Immunology, vol. 42, pp. 447-457, 2012.
Beziat, V. et al., "NK Cell Responses To Cytomegalovirus Infection Lead To Stable Imprints In The Human Kir Repertoire And Involve Activating KIRs", Immunobiology, vol. 121, No. 14, pp. 2678-2689.
Biron, S., A. et al., "Severe Herpesvirus Infection In an Adolescent without Natural killer Cells", Medical Intelligence, vol. 320, No. 26, pp. 1731-1735, 1989.
Björkström, A., K. et al., "Rapid Expansion And Long-Term Persistence Of Elevated NK Cell Numbers In Humans Infected With Hantavirus", The Journal of Experimental Medicine, vol. 208, No. 1, pp. 13-21, 2010.
Borrego, F. et al., "Recognition of Human Histocompatibility Leukocyte Antigen (HLA)-E Complexed with HLA Class I Signal Sequence—derived Peptides by CD94/NKG2 Confers Protection from Natural Killer Cell—mediated Lysis", The Journal of Experimental Medicine, vol. 187, No. 5, pp. 813-818, 1998.
Borst, E. et al., "Cloning of the Human Cytomegalovirus (HCMV) Genome as an Infectious Bacterial Artificial Chromosome in Escherichia coli: a New Approach for Construction of HCMV Mutants", Journal of Virology, vol. 73, No. 10, pp. 8320-8329, 1999.
Braud, V. et al., "The Human Major Histocompatibility Complex Class lb Molecule HLA-E Binds Signal Sequence-Derived Peptides With Primary Anchor Residues At Positions 2 and 9", European Journal of Immunology, vol. 27, pp. 1164-1169, 1997.
Braud, A., M. et al., "HLA-E Binds to Natural Killer Cell Receptors CD94/NKG2A, B and C", Nature, vol. 391, pp. 795-799, 1998.
Brooks, A., G. et al., "Specific Recognition of HLA-E, But Not Classical, HLA Class I Molecules by Soluble CD94/NKG2A and NK Cells", The Journal of Immunology, vol. 162, pp. 305-313, 1999.
Carosella, A., D. et al., "HLA-G: From Biology To Clinical Benefits", Trends in Immunology, vol. 29, No. 3, pp. 125-132, 2008.
Cerboni, C. et al., "Synergistic Effect Of IFN-Q and Human Cytomegalovirus Protein UL40 In The HLA-Edependent Protection From NK Cell-Mediated Cytotoxicity", European Journal of Immunology, vol. 31, pp. 2926-2935, 2001.
Chiesa, M.D. et al., "Human Cytomegalovirus Infection Promotes Rapid Maturation of NK Cells Expressing Activating Killer Ig-like Receptor in Patients Transplanted with NKG2C2/2 Umbilical Cord Blood", The Journal of Immunology, vol. 192, pp. 1471-1479, 2014.
Cichocki, F. et al., "$CD56^{dim}CD57^{+}NKG2C^{+}$ NK Cell Expansion Is Associated With Reduced Leukemia Relapse After Reduced Intensity HCT", Leukemia, vol. 30, No. 2, pp. 456-463, 2016.
Cooper, M., A. et al. "Cytokine-Induced Memory-Like Natural Killer Cells", Proceedings of the National Academy of Sciences of the U.S.A., vol. 106, No. 6, pp. 1915-1919, 2009.
Cossarizza, A. et al., "Guidelines For The Use of Flow Cytometry And Cell Sorting In Immunological Studies", European Journal of Immunology, vol. 47, pp. 1584-1797, 2017.
Crnković-Mertens, I. et al., "Virus Attenuation after Deletion of the Cytomegalovirus Fc Receptor Gene Is Not due to Antibody Control", Journal of Virology, vol. 72, No. 2, pp. 1377-1382, 1998.
Crooks, G., E. et al., "WebLogo: A Sequence Logo Generator, Genome Research", vol. 14, pp. 1188-1190, 2004.
Curigliano, G. et al., "Molecular Pathways: Human Leukocyte AntigenG(HLA-G)", Molecular Pathways, vol. 19, No. 20, pp. 5564-5571, 2013.
De Boera, R., J. et al., "Estimating Lymphocyte Division and Death Rates from CFSE Data", Bulletin of Mathematical Biology, vol. 68, pp. 1011-1031, 2006.
Djaoud, Z. et al., "Cytomegalovirus-Infected Primary Endothelial Cells Trigger NKG2C+ Natural Killer Cells", Journal of Innate Immunity, vol. 8, pp. 374-385, 2016.
Elbasani, E. et al., "Analysis of Essential Viral Gene Functions after Highly Efficient Adenofection of Cells with Cloned Human Cytomegalovirus Genomes", Viruses, vol. 6, pp. 354-370, 2014.
European Search Report in European Application No. EP 18 16 2281, dated Aug. 30, 2018.
Foley, B. et al., "Cytomegalovirus Reactivation After Allogeneic Transplantation Promotes A Lasting Increase In Educated $NKG2C^{+}$ Natural Killer Cells With Potent Function", Blood, vol. 112, No. 11, pp. 2665-2674, 2012.
Garcia-Sastre, A. et al., "Type 1 Interferons and the Virus-Host Relationship: A Lesson in Détente", Science, vol. 312, pp. 879-883, 2006.
Garrigue, I. et al., "Variability of UL18, UL40, UL111a and US3 Immunomodulatory Genes Among Human Cytomegalovirus Clinical Isolates From Renal Transplant Recipients", Journal of Clinical Virology, vol. 40, pp. 120-128, 2007.
Gett, A., G. et al., "A Cellular Calculus For Signal Integration By T Cells", Nature Immunology, vol. 1, No. 3, pp. 239-244, 2000.
Gibson, D., G. et al., "Enzymatic assembly of DNA Molecules Up To Several Hundred Kilobases", Nature Methods, vol. 6, No. 5, pp. 343-347, 2009.
Goodier, M., R. et al., "Rapid NK Cell Differentiation In A Population With Near-Universal Human Cytomegalovirus Infection Is Attenuated By NKG2C Deletions", Immunobiology, vol. 124, No. 14, pp. 2213-2223, 2014.
Guma, M. et al., "Expansion of $CD94/NKG2C^{+}$ NK Cells in Response To Human Cytomegalovirus-Infected Fibroblasts", Blood, vol. 107, No. 9, pp. 3624-3631, 2006.
Guma, M. et al., "Imprint Of Human Cytomegalovirus Infection On The NK Cell Receptor Repertoire", Immunobiology, vol. 104, No. 12, pp. 3664-3671, 2004.
Hammer, Q. et al., "About Training and Memory: NK-Cell Adaptation to Viral Infections", Advance in Immunology, vol. 133, 171-207, 2017.
Hammer, Q. et al., "OMIP-039: Detection and Analysis of Human Adaptive NKG2C1 Natural Killer Cells", Cytometry, pp. 997-1000, 2017.
Heatley, S., L. et al., "Polymorphism in Human Cytomegalovirus UL40 Impacts on Recognition of Human Leukocyte Antigen-E (HLA-E) by Natural Killer Cells", Journal of Biological Chemistry, vol. 288, No. 12, pp. 8679-8690, 2013.
Hobom, U. et al., "Fast Screening Procedures for Random Transposon Libraries of Cloned Herpesvirus Genomes: Mutational Analysis of Human Cytomegalovirus Envelope Glycoprotein Genes", Journal of Virology, vol. 74, No. 17, pp. 7720-7729, 2000.
Jackson, S., E. et al., "Human Cytomegalovirus Immunity and Immune Evasion", Virus Research, vol. 157, pp. 151-160, 2011.
Kaiser, B., K. et al., "Structural basis for NKG2A/CD94 recognition of HLA-E", Proceedings of the National Academy of Sciences of the U.S.A., vol. 105, No. 18, pp. 6696-6701, 2008.
Kielczewska, A. et al., "Ly49P Recognition Of Cytomegalovirusinfected Cells Expressing H2-D K And Cmvencoded M04 Correlates With The NK Cell Antiviral Response", Journal of Experimental Medicine, vol. 206, No. 3, pp. 515-523, 2009.
Kim, D. et al., "TopHat2: Accurate Alignment Of Transcriptomes In The Presence Of Insertions, Deletions And Gene Fusions", Genome Biology, vol. 14, pp. 1-13, 2013.
Kochan, G. et al., "Role Of Non-Classical MHC Class I Molecules In Cancer Immunosuppression", Oncoimmunology, vol. 2, No. 11, pp. 1-8, 2013.
Kuijpers, T., w. et al., "Human NK cells can control CMV infection in the absence of T cells", Blood, vol. 112, No. 3, pp. 914-915, 2008.
Langmead, B. et al., "Fast gapped-read alignment with Bowtie 2", Nature Methods, vol. 9, No. 4, pp. 357-360, 2012.

(56) References Cited

OTHER PUBLICATIONS

Lee, N. et al., "HLA-E is a Major Ligand For The Natural Killer Inhibitory Receptor CD94yNKG2A", Proceedings of the National Academy of Sciences of the U.S.A., vol. 95, pp. 5199-5204, 1998.
Lee, J. et al., "Epigenetic Modification and Antibody-Dependent Expansion of Memory-like NK Cells in Human Cytomegalovirus-Infected Individuals", Immunity, vol. 42, pp. 431-442, 2015.
Liao, Y. et al., "Featurecounts: An Efficient General Purpose Program For Assigning Sequence Reads To Genomic Features", Bioinformatics, vol. 30, No. 7, pp. 923-930, 2014.
Lin, A. et al., "Human Leukocyte Antigen-G (HLA-G) Expression in Cancers: Roles in Immune Evasion, Metastasis and Target for Therapy", Molecular Medicine, vol. 21, pp. 782-791, 2015.
Liu, L., L. et al., "Critical Role of CD2 Co-stimulation in Adaptive Natural Killer Cell Responses Revealed in NKG2C-Deficient Humans", Cell Reports, vol. 15, pp. 1088-1099, 2016.
Llano, M. et al., "HLA-E-Bound Peptides Influence Recognition By Inhibitory And Triggering CD94/NKG2 Receptors: Preferential Response To An HLA-G-Derived Nonamer", European Journal of Immunology, vol. 28, pp. 285-2863, 1998.
Lopez-Verger, S. et al., Expansion Of A Unique CD57+NKG2Chi Natural Killer Cell Subset During Acute Human Cytomegalovirus Infection, Proceedings of the National Academy of Sciences of the U.S.A., vol. 108, No. 36, pp. 14725-14732, 2011.
Love, M., I. et al., Moderated Estimation Of Fold Change And Dispersion For RNA-Seq Data With Deseq2, Genome Biology, vol. 15, No. 550, pp. 1-21, 2014.
Luetke-Eversloh, M. et al., "Human Cytomegalovirus Drives Epigenetic Imprinting of the IFNG Locus in NKG2Chi Natural Killer Cells", PLOS Pathogens, vol. 10, No. 10, pp. 1-13, 2014.
Michaelsson, J. et al., "A Signal Peptide Derived from hsp60 Binds HLA-E and Interferes with CD94/NKG2A Recognition", Journal of Experimental Medicine, vol. 196, No. 11, pp. 1403-1414, 2002.
Nabekura, T. et al., "Costimulatory Molecule DNAM-1 Is Essential for Optimal Differentiation of Memory Natural Killer Cells during Mouse Cytomegalovirus Infection", Immunity, vol. 40, pp. 225-234, 2014.
O'Sullivan, T., E. et al., "Natural Killer Cell Memory", Immunity, vol. 43, pp. 634-645, 2015.
Paul, P. et al., "HLA-G, -E, -F Preworkshop: Tools and Protocols for Analysis of Non-Classical Class I Genes Transcription and Protein Expression", Human Immunology, vol. 61, pp. 1177-1195, 2000.
Petitdemange, C. et al., "Unconventional Repertoire Profile Is Imprinted During Acute Chikungunya Infection For Natural Killer Cells Polarization Toward Cytotoxicity", PLOS Pathogens, vol. 7, No. 9, pp. 1-13, 2011.
Petrie, E., J. et al., "CD94-NKG2A Recognition Of Human Leukocyte Antigen (HLA)-E Bound To An HLA Class I Leader Sequence", The Journal of Experimental Medicine, vol. 205, No. 3, pp. 725-735, 2008.
Pietra, G. et al., "HLA-E-Restricted Recognition Ff Cytomegalovirusderived Peptides By Human CD8+ Cytolytic T Lymphocytes", Proceedings of the National Academy of Sciences of the U.S.A., vol. 100, No. 19, pp. 10896-10901, 2003.
Pupuleku, A. et al., "Elusive Role of the CD94/NKG2C NK Cell Receptor in the Response to Cytomegalovirus: Novel Experimental Observations in a Reporter Cell System", Frontiers in Immunology, vol. 8, No. 1317, pp. 1-12, 2017.
Ravens, S. et al., "Human gd T Cells Are Quickly Reconstituted After Stem-Cell Transplantation And Show Adaptive Clonal Expansion In Response To Viral Infection", Nature Immunology, vol. 18, No. 4, 393-403, 2017.
Roederer, M. et al., "SPICE: Exploration and Analysis of Post-Cytometric Complex Multivariate Datasets", Cytometry Part A, 79A:167-174, 2011.
Roederer, M. "Interpretation of Cellular Proliferation Data: Avoid the Panglossian", Cytometry Part A: 95-101, 2011.
Rolle, A. Et Al., "IL-12—Producing Monocytes And HLA-E Control HCMV-Driven NKG2C+ NK Cell Expansion", The Journal of clinical Investigation, vol. 124, No. 12, pp. 5305-5316, 2014.
Romee, R. et al., "Cytokine activation induces human memory-like NK cells", Blood, vol. 120, No. 24, pp. 4751-4761, 2012.
Schlums, H. et al., "Cytomegalovirus Infection Drives Adaptive Epigenetic Diversification of NK Cells with Altered Signaling and Effector Function", Immunity, vol. 42, No. 3, pp. 443-456, 2015.
Seliger, B. et al., "Structure, Expression And Function Of HLA-G In Renal Cell Carcinoma", Seminars in Cancer Biology, vol. 17, pp. 444-450, 2007.
Sinzger, C. et al., "Cloning And Sequencing Of A Highly Productive, Endotheliotropic Virus Strain Derived From Human Cytomegalovirus TB40/E", Journal of General Virology, vol. 89, pp. 359-368, 2008.
Smith, G. A. et al., "A Self-Recombining Bacterial Artificial Chromosome And Its Application For Analysis Of Herpesvirus Pathogenesis", Proceedings of the National Academy of Sciences of the U.S.A., vol. 97, No. 9, pp. 4873-4878, 2000.
Smith, H. R. et al., "Recognition Of A Virus-Encoded Ligand By A Natural Killer Cell Activation Receptor", Proceedings of the National Academy of Sciences of the U.S.A., vol. 99, No. 13, pp. 8826-8831, 2002.
Smyth, M. J. et al., "Non-Classical MHC Class I Molecules Regulating Natural Killer Cell Function", Oncoimmunology, vol. 2, No. 3, pp. 1-2, 2013.
Sullivan, C. et al., "The Heterodimeric Assembly of the CD94-NKG2 Receptor Family and Implications for Human Leukocyte Antigen-E Recognition", Immunity, vol. 27, pp. 900-911, 2007.
Sun, J., C. et al, "Adaptive Immune Features Of Natural Killer Cells", Nature, vol. 457, pp. 557-561, 2009.
Sun, J., C. et al., "Proinflammatory cytokine signaling required for the generation of natural killer cell memory", vol. 209, No. 5, pp. 947-954, 2012.
Tischer, B., K. et al., "*En Passant* Mutagenesis: A Two Step Markerless Red Recombination System", Methods in Molecular Biology, vol. 634, pp. 421-430, 2010.
Tomasec, P. et al., "Surface Expression of HLA-E, an Inhibitor of Natural Killer Cells, Enhanced by Human Cytomegalovirus gpUL40", Science, vol. 287, pp. 1031-1034, 2000.
Ulbrecht, M. et al., "Cutting Edge: The Human Cytomegalovirus UL40 Gene Product Contains a Ligand for HLA-E and Prevents NK Cell-Mediated Lysis", The Journal of immunology, vol. 164, pp. 5019-5022, 2000.
Vales-Gomez, M. et al., "Kinetics and peptide dependency of the binding of the inhibitory NK receptor CD94/NKG2-A and the activating receptor CD94/NKG2-C to HLA-E", The EMBO Journal, vol. 18, No. 15, pp. 4250-4260, 1999.
Van De Berg, P.J., "Human Cytomegalovirus Induces Systemic Immune Activation Characterized by a Type 1 Cytokine Signature", The Journal of Infectious Diseases, vol. 202, No. 5, pp. 690-699, 2010.
Van Der Ploeg, K. et al. "Modulation of human leukocyte Antigen_C by Human Cytomegalovirus stimulates KIR2DS1 recognition by Natural Killer Cells" Frontiers in Immunology 8: 1-20.
Viver, E.et al., "Functions of Natural Killer Cells", Natural immunology, vol. 9, No. 5, pp. 503-510, 2008.
Wang, E., C. et al., "UL40-Mediated NK Evasion During Productive Infection With Human Cytomegalovirus", Proceedings of the National Academy of Sciences of the U.S.A., vol. 99, No. 11, pp. 7570-7575, 2002.

* cited by examiner a

RMA-S/HLA-E + VMAPRTLIL  RMA-S/HLA-E/LFA-3 + VMAPRTLIL b

| | No peptide | VMAPRTLIL | VMAPRTLFL |
|---|---|---|---|
| RMA-S/HLA-E |  |  |  |
| RMA-S/HLA-E/LFA-3 |  |  |  |

Pie legend: ☐ 0  ▨ 1  ▨ 2  ▨ 3  ■ 4 functions

Arc legend: ━ CCL3⁺  ━ CD107a⁺  ━ IFN-γ⁺  ━ TNF⁺ c d

SEQUENCE LISTING

```
<160> NUMBER OF SEQ ID NOS: 70

<210> SEQ ID NO 1
<211> LENGTH: 9
<212> TYPE: PRT
<213> ORGANISM: Artificial Sequence
<220> FEATURE:
<223> OTHER INFORMATION: synthesized peptide
<220> FEATURE:
<221> NAME/KEY: SITE
<222> LOCATION: (8)...(8)
<223> OTHER INFORMATION: Xaa is an amino acid with a hydrophobic side
      chain (Ala, Ile, Leu, Phe, Val, Pro, Gly), preferably Val, Leu,
      Ile or Phe.

<400> SEQUENCE: 1

Val Met Ala Pro Arg Thr Leu Xaa Leu
1               5

<210> SEQ ID NO 2
<211> LENGTH: 9
<212> TYPE: PRT
<213> ORGANISM: Artificial Sequence
<220> FEATURE:
```

<223> OTHER INFORMATION: synthesized peptide

<400> SEQUENCE: 2

Val Met Ala Pro Arg Thr Leu Phe Leu
1               5

<210> SEQ ID NO 3
<211> LENGTH: 9
<212> TYPE: PRT
<213> ORGANISM: Artificial Sequence
<220> FEATURE:
<223> OTHER INFORMATION: synthesized peptide

<400> SEQUENCE: 3

Val Met Ala Pro Arg Thr Leu Ile Leu
1               5

<210> SEQ ID NO 4
<211> LENGTH: 9
<212> TYPE: PRT
<213> ORGANISM: Artificial Sequence
<220> FEATURE:
<223> OTHER INFORMATION: synthesized peptide

<400> SEQUENCE: 4

Val Met Ala Pro Arg Thr Leu Leu Leu
1               5

<210> SEQ ID NO 5
<211> LENGTH: 9
<212> TYPE: PRT
<213> ORGANISM: Artificial Sequence
<220> FEATURE:
<223> OTHER INFORMATION: synthesized peptide

<400> SEQUENCE: 5

Val Met Ala Pro Arg Thr Leu Val Leu
1               5

<210> SEQ ID NO 6
<211> LENGTH: 9
<212> TYPE: PRT
<213> ORGANISM: Artificial Sequence
<220> FEATURE:
<223> OTHER INFORMATION: synthesized peptide

<400> SEQUENCE: 6

Val Met Ala Pro Arg Ser Leu Leu Leu
1               5

<210> SEQ ID NO 7
<211> LENGTH: 9
<212> TYPE: PRT
<213> ORGANISM: Artificial Sequence
<220> FEATURE:
<223> OTHER INFORMATION: synthesized peptide

<400> SEQUENCE: 7

Val Met Ala Pro Arg Ser Leu Ile Leu
1               5

<210> SEQ ID NO 8
<211> LENGTH: 9
<212> TYPE: PRT
<213> ORGANISM: Artificial Sequence
<220> FEATURE:
<223> OTHER INFORMATION: synthesized peptide

<400> SEQUENCE: 8

Val Met Thr Pro Arg Thr Leu Val Leu
1               5

<210> SEQ ID NO 9
<211> LENGTH: 9
<212> TYPE: PRT
<213> ORGANISM: Artificial Sequence
<220> FEATURE:
<223> OTHER INFORMATION: synthesized peptide

<400> SEQUENCE: 9

Val Met Ala Pro Arg Ile Leu Ile Leu
1               5

<210> SEQ ID NO 10
<211> LENGTH: 9
<212> TYPE: PRT
<213> ORGANISM: Artificial Sequence
<220> FEATURE:
<223> OTHER INFORMATION: synthesized peptide

<400> SEQUENCE: 10

Ala Met Ala Pro Arg Thr Leu Ile Leu
1               5

<210> SEQ ID NO 11
<211> LENGTH: 9
<212> TYPE: PRT
<213> ORGANISM: Artificial Sequence
<220> FEATURE:
<223> OTHER INFORMATION: synthesized peptide

<400> SEQUENCE: 11

Val Ile Ala Pro Arg Thr Leu Val Leu
1               5

<210> SEQ ID NO 12
<211> LENGTH: 9
<212> TYPE: PRT
<213> ORGANISM: Artificial Sequence
<220> FEATURE:
<223> OTHER INFORMATION: synthesized peptide

<400> SEQUENCE: 12

Val Met Ala Pro Gln Ser Leu Leu Leu
1               5

<210> SEQ ID NO 13
<211> LENGTH: 9
<212> TYPE: PRT
<213> ORGANISM: Artificial Sequence
<220> FEATURE:
<223> OTHER INFORMATION: synthesized peptide

<400> SEQUENCE: 13

Val Met Ala Pro Arg Thr Phe Val Leu
1               5

<210> SEQ ID NO 14
<211> LENGTH: 9
<212> TYPE: PRT
<213> ORGANISM: Artificial Sequence
<220> FEATURE:
<223> OTHER INFORMATION: synthesized peptide

```
<400> SEQUENCE: 14

Val Met Thr Pro Arg Thr Leu Ile Leu
1               5

<210> SEQ ID NO 15
<211> LENGTH: 9
<212> TYPE: PRT
<213> ORGANISM: Artificial Sequence
<220> FEATURE:
<223> OTHER INFORMATION: synthesized peptide

<400> SEQUENCE: 15

Val Thr Ala Pro Arg Thr Leu Ile Leu
1               5

<210> SEQ ID NO 16
<211> LENGTH: 9
<212> TYPE: PRT
<213> ORGANISM: Artificial Sequence
<220> FEATURE:
<223> OTHER INFORMATION: synthesized peptide

<400> SEQUENCE: 16

Val Thr Ala Pro Arg Thr Leu Leu Leu
1               5

<210> SEQ ID NO 17
<211> LENGTH: 9
<212> TYPE: PRT
<213> ORGANISM: Artificial Sequence
<220> FEATURE:
<223> OTHER INFORMATION: synthesized peptide

<400> SEQUENCE: 17

Val Met Ala Pro Trp Thr Leu Leu Leu
1               5

<210> SEQ ID NO 18
<211> LENGTH: 9
<212> TYPE: PRT
<213> ORGANISM: Artificial Sequence
<220> FEATURE:
<223> OTHER INFORMATION: synthesized peptide

<400> SEQUENCE: 18

Val Met Val Pro Arg Ser Leu Ile Leu
1               5

<210> SEQ ID NO 19
<211> LENGTH: 9
<212> TYPE: PRT
<213> ORGANISM: Artificial Sequence
<220> FEATURE:
<223> OTHER INFORMATION: synthesized peptide

<400> SEQUENCE: 19

Ala Met Ala Pro Arg Thr Leu Val Leu
1               5

<210> SEQ ID NO 20
<211> LENGTH: 9
<212> TYPE: PRT
<213> ORGANISM: Artificial Sequence
<220> FEATURE:
<223> OTHER INFORMATION: synthesized peptide

<400> SEQUENCE: 20
```

```
Val Ile Ala Pro Arg Thr Leu Ile Leu
1               5

<210> SEQ ID NO 21
<211> LENGTH: 9
<212> TYPE: PRT
<213> ORGANISM: Artificial Sequence
<220> FEATURE:
<223> OTHER INFORMATION: synthesized peptide

<400> SEQUENCE: 21

Val Ile Ala Pro Arg Thr Leu Leu Leu
1               5

<210> SEQ ID NO 22
<211> LENGTH: 9
<212> TYPE: PRT
<213> ORGANISM: Artificial Sequence
<220> FEATURE:
<223> OTHER INFORMATION: synthesized peptide

<400> SEQUENCE: 22

Val Leu Ala Pro Arg Thr Leu Ile Leu
1               5

<210> SEQ ID NO 23
<211> LENGTH: 9
<212> TYPE: PRT
<213> ORGANISM: Artificial Sequence
<220> FEATURE:
<223> OTHER INFORMATION: synthesized peptide

<400> SEQUENCE: 23

Val Met Ala Leu Arg Thr Leu Ile Leu
1               5

<210> SEQ ID NO 24
<211> LENGTH: 9
<212> TYPE: PRT
<213> ORGANISM: Artificial Sequence
<220> FEATURE:
<223> OTHER INFORMATION: synthesized peptide

<400> SEQUENCE: 24

Val Met Ala Pro Arg Gly Leu Ile Leu
1               5

<210> SEQ ID NO 25
<211> LENGTH: 9
<212> TYPE: PRT
<213> ORGANISM: Artificial Sequence
<220> FEATURE:
<223> OTHER INFORMATION: synthesized peptide

<400> SEQUENCE: 25

Val Met Ala Pro Arg Asn Leu Ile Leu
1               5

<210> SEQ ID NO 26
<211> LENGTH: 9
<212> TYPE: PRT
<213> ORGANISM: Artificial Sequence
<220> FEATURE:
<223> OTHER INFORMATION: synthesized peptide

<400> SEQUENCE: 26
```

Val Met Ala Pro Arg Thr Leu Phe Val
1               5

<210> SEQ ID NO 27
<211> LENGTH: 9
<212> TYPE: PRT
<213> ORGANISM: Artificial Sequence
<220> FEATURE:
<223> OTHER INFORMATION: synthesized peptide

<400> SEQUENCE: 27

Val Met Ala Pro Arg Thr Leu Leu Met
1               5

<210> SEQ ID NO 28
<211> LENGTH: 9
<212> TYPE: PRT
<213> ORGANISM: Artificial Sequence
<220> FEATURE:
<223> OTHER INFORMATION: synthesized peptide

<400> SEQUENCE: 28

Val Met Ala Pro Arg Thr Leu Val Met
1               5

<210> SEQ ID NO 29
<211> LENGTH: 9
<212> TYPE: PRT
<213> ORGANISM: Artificial Sequence
<220> FEATURE:
<223> OTHER INFORMATION: synthesized peptide

<400> SEQUENCE: 29

Val Met Ala Pro Arg Thr Ser Leu Leu
1               5

<210> SEQ ID NO 30
<211> LENGTH: 9
<212> TYPE: PRT
<213> ORGANISM: Artificial Sequence
<220> FEATURE:
<223> OTHER INFORMATION: synthesized peptide

<400> SEQUENCE: 30

Val Met Ala Pro Arg Thr Ser Val Leu
1               5

<210> SEQ ID NO 31
<211> LENGTH: 9
<212> TYPE: PRT
<213> ORGANISM: Artificial Sequence
<220> FEATURE:
<223> OTHER INFORMATION: synthesized peptide

<400> SEQUENCE: 31

Val Met Ala Pro Trp Thr Leu Ile Leu
1               5

<210> SEQ ID NO 32
<211> LENGTH: 9
<212> TYPE: PRT
<213> ORGANISM: Artificial Sequence
<220> FEATURE:
<223> OTHER INFORMATION: synthesized peptide

<400> SEQUENCE: 32

Val Met Ala Pro Trp Thr Leu Val Leu

```
1               5

<210> SEQ ID NO 33
<211> LENGTH: 9
<212> TYPE: PRT
<213> ORGANISM: Artificial Sequence
<220> FEATURE:
<223> OTHER INFORMATION: synthesized peptide

<400> SEQUENCE: 33

Val Met Asp Pro Arg Thr Leu Leu Leu
1               5

<210> SEQ ID NO 34
<211> LENGTH: 9
<212> TYPE: PRT
<213> ORGANISM: Artificial Sequence
<220> FEATURE:
<223> OTHER INFORMATION: synthesized peptide

<400> SEQUENCE: 34

Val Met Gly Pro Arg Thr Leu Ile Leu
1               5

<210> SEQ ID NO 35
<211> LENGTH: 9
<212> TYPE: PRT
<213> ORGANISM: Artificial Sequence
<220> FEATURE:
<223> OTHER INFORMATION: synthesized peptide

<400> SEQUENCE: 35

Val Met Gly Pro Arg Thr Leu Leu Leu
1               5

<210> SEQ ID NO 36
<211> LENGTH: 9
<212> TYPE: PRT
<213> ORGANISM: Artificial Sequence
<220> FEATURE:
<223> OTHER INFORMATION: synthesized peptide

<400> SEQUENCE: 36

Val Met Val Pro Gln Thr Leu Ile Leu
1               5

<210> SEQ ID NO 37
<211> LENGTH: 9
<212> TYPE: PRT
<213> ORGANISM: Artificial Sequence
<220> FEATURE:
<223> OTHER INFORMATION: synthesized peptide

<400> SEQUENCE: 37

Val Met Val Pro Arg Thr Leu Leu Leu
1               5

<210> SEQ ID NO 38
<211> LENGTH: 9
<212> TYPE: PRT
<213> ORGANISM: Artificial Sequence
<220> FEATURE:
<223> OTHER INFORMATION: synthesized peptide

<400> SEQUENCE: 38

Val Thr Ala Pro Arg Thr Leu Val Leu
1               5
```

```
<210> SEQ ID NO 39
<211> LENGTH: 9
<212> TYPE: PRT
<213> ORGANISM: Artificial Sequence
<220> FEATURE:
<223> OTHER INFORMATION: synthesized peptide

<400> SEQUENCE: 39

Val Val Ala Pro Arg Thr Leu Ile Leu
1               5

<210> SEQ ID NO 40
<211> LENGTH: 9
<212> TYPE: PRT
<213> ORGANISM: Artificial Sequence
<220> FEATURE:
<223> OTHER INFORMATION: synthesized peptide

<400> SEQUENCE: 40

Val Val Ala Pro Arg Thr Leu Leu Leu
1               5

<210> SEQ ID NO 41
<211> LENGTH: 9
<212> TYPE: PRT
<213> ORGANISM: Artificial Sequence
<220> FEATURE:
<223> OTHER INFORMATION: synthesized peptide

<400> SEQUENCE: 41

Val Met Val Pro Arg Thr Leu Ile Leu
1               5

<210> SEQ ID NO 42
<211> LENGTH: 9
<212> TYPE: PRT
<213> ORGANISM: Artificial Sequence
<220> FEATURE:
<223> OTHER INFORMATION: synthesized peptide

<400> SEQUENCE: 42

Val Met Ala Thr Arg Thr Leu Leu Leu
1               5

<210> SEQ ID NO 43
<211> LENGTH: 20
<212> TYPE: DNA
<213> ORGANISM: Artificial Sequence
<220> FEATURE:
<223> OTHER INFORMATION: synthesized peptide

<400> SEQUENCE: 43
ggctctgtct cgtcgtcatt                                           20

<210> SEQ ID NO 44
<211> LENGTH: 20
<212> TYPE: DNA
<213> ORGANISM: Artificial Sequence
<220> FEATURE:
<223> OTHER INFORMATION: synthesized peptide

<400> SEQUENCE: 44
taagggcact cgtgaggatg                                           20

<210> SEQ ID NO 45
```

```
<211> LENGTH: 20
<212> TYPE: DNA
<213> ORGANISM: Artificial Sequence
<220> FEATURE:
<223> OTHER INFORMATION: synthesized peptide

<400> SEQUENCE: 45
caacagtcgg cagaatgaac                                                    20

<210> SEQ ID NO 46
<211> LENGTH: 20
<212> TYPE: DNA
<213> ORGANISM: Artificial Sequence
<220> FEATURE:
<223> OTHER INFORMATION: synthesized peptide

<400> SEQUENCE: 46
ctggaacacg agcggacata                                                    20

<210> SEQ ID NO 47
<211> LENGTH: 20
<212> TYPE: DNA
<213> ORGANISM: Homo sapiens

<400> SEQUENCE: 47
ttcgtcatgg gtgtgaacca                                                    20

<210> SEQ ID NO 48
<211> LENGTH: 21
<212> TYPE: DNA
<213> ORGANISM: Homo sapiens

<400> SEQUENCE: 48
ggactgtggt catgagtcct t                                                  21

<210> SEQ ID NO 49
<211> LENGTH: 56
<212> TYPE: DNA
<213> ORGANISM: Homo sapiens

<400> SEQUENCE: 49
tctttcccta cacgacgctc ttccgatcta tgagttaata ttggatttat gttttt           56

<210> SEQ ID NO 50
<211> LENGTH: 63
<212> TYPE: DNA
<213> ORGANISM: Homo sapiens

<400> SEQUENCE: 50
gtgactggag ttcagacgtg tgctcttccg atctatataa ataacatacc ttctatattc       60
ttt                                                                      63

<210> SEQ ID NO 51
<211> LENGTH: 64
<212> TYPE: DNA
<213> ORGANISM: Artificial Sequence
<220> FEATURE:
<221> NAME/KEY: misc_feature
<222> LOCATION: (25)..(30)
<223> OTHER INFORMATION: n is a, c, g, or t
<220> FEATURE:
<223> OTHER INFORMATION: synthesized nucleotide sequence

<400> SEQUENCE: 51
caagcagaag acggcatacg agatnnnnnn gtgactggag ttcagacgtg tgctcttccg       60
```

<210> SEQ ID NO 52
<211> LENGTH: 63
<212> TYPE: DNA
<213> ORGANISM: Artificial Sequence
<220> FEATURE:
<221> NAME/KEY: misc_feature
<222> LOCATION: (30)..(35)
<223> OTHER INFORMATION: n is a, c, g, or t
<220> FEATURE:
<223> OTHER INFORMATION: synthesized nucleotide sequence

<400> SEQUENCE: 52
aatgatacgg cgaccaccga gatctacacn nnnnntcttt ccctacacga cgctcttccg    60
atc                                                                  63

<210> SEQ ID NO 53
<211> LENGTH: 87
<212> TYPE: DNA
<213> ORGANISM: Artificial Sequence
<220> FEATURE:
<223> OTHER INFORMATION: synthesized nucleotide sequence

<400> SEQUENCE: 53
gatcacatcc ccttgcagta ccagacgcag ggctataact tcgtataatg tatgctatac    60
gaagttatgg ctggtttatg catatcg                                        87

<210> SEQ ID NO 54
<211> LENGTH: 59
<212> TYPE: DNA
<213> ORGANISM: Artificial Sequence
<220> FEATURE:
<223> OTHER INFORMATION: synthesized nucleotide sequence

<400> SEQUENCE: 54
tgcatgccat ggtacccggg agctcgaatt cgaagcttct ttcccttgt caacagcaa      59

<210> SEQ ID NO 55
<211> LENGTH: 34
<212> TYPE: DNA
<213> ORGANISM: Artificial Sequence
<220> FEATURE:
<223> OTHER INFORMATION: synthesized nucleotide sequence

<400> SEQUENCE: 55
ctagcagatc tgcagggacg catcgtggcc ggat                                34

<210> SEQ ID NO 56
<211> LENGTH: 39
<212> TYPE: DNA
<213> ORGANISM: Artificial Sequence
<220> FEATURE:
<223> OTHER INFORMATION: synthesized nucleotide sequence

<400> SEQUENCE: 56
taaggatgca tgtttaaacg tgaccacgtc gtggaatgc                           39

<210> SEQ ID NO 57
<211> LENGTH: 66
<212> TYPE: DNA
<213> ORGANISM: Artificial Sequence
<220> FEATURE:
<223> OTHER INFORMATION: synthesized nucleotide sequence

```
<400> SEQUENCE: 57
gtggtcacgt ttaaacatgc atccttaatt aaggctgcga tctatcgagt tttcccagtc    60
acgacg                                                                66

<210> SEQ ID NO 58
<211> LENGTH: 35
<212> TYPE: DNA
<213> ORGANISM: Artificial Sequence
<220> FEATURE:
<223> OTHER INFORMATION: synthesized nucleotide sequence

<400> SEQUENCE: 58
taggaagctt gatatcgaac aaacgaccca acacc                                35

<210> SEQ ID NO 59
<211> LENGTH: 61
<212> TYPE: DNA
<213> ORGANISM: Artificial Sequence
<220> FEATURE:
<223> OTHER INFORMATION: synthesized nucleotide sequence

<400> SEQUENCE: 59
gccagatcac atcccttgc agtaccagac gcagggctag gacggtatcg ataagctgga      60
t                                                                     61

<210> SEQ ID NO 60
<211> LENGTH: 61
<212> TYPE: DNA
<213> ORGANISM: Artificial Sequence
<220> FEATURE:
<223> OTHER INFORMATION: synthesized nucleotide sequence

<400> SEQUENCE: 60
tgcatgccat ggtacccggg agctcgaatt cgaagcttct gacgcatcgt ggccggatct     60
c                                                                     61

<210> SEQ ID NO 61
<211> LENGTH: 76
<212> TYPE: DNA
<213> ORGANISM: Artificial Sequence
<220> FEATURE:
<223> OTHER INFORMATION: synthesized nucleotide sequence

<400> SEQUENCE: 61
acaggagtcc aagcgtcaga attaaagtcc gcggagccat aaccgcgcaa gtgaagccga     60
cgcatcgtgg ccggat                                                     76

<210> SEQ ID NO 62
<211> LENGTH: 76
<212> TYPE: DNA
<213> ORGANISM: Artificial Sequence
<220> FEATURE:
<223> OTHER INFORMATION: synthesized nucleotide sequence

<400> SEQUENCE: 62
aaattcagca acactcgtat cggcttcact tgcgcggtta tggctccgcg gactttaatg     60
gtgaccacgt cgtgga                                                     76

<210> SEQ ID NO 63
<211> LENGTH: 78
<212> TYPE: DNA
<213> ORGANISM: Artificial Sequence
```

```
<220> FEATURE:
<223> OTHER INFORMATION: synthesized nucleotide sequence

<400> SEQUENCE: 63
tcctcataca caggagtcca agcgtcagaa ataaagtccg cggagccata accgcgcaag    60
gacgcatcgt ggccggat                                                 78

<210> SEQ ID NO 64
<211> LENGTH: 78
<212> TYPE: DNA
<213> ORGANISM: Artificial Sequence
<220> FEATURE:
<223> OTHER INFORMATION: synthesized nucleotide sequence

<400> SEQUENCE: 64
aacactcgta tcggcttcac ttgcgcggtt atggctccgc ggactttatt tctgacgctt    60
tggtgaccac gtcgtgga                                                 78

<210> SEQ ID NO 65
<211> LENGTH: 78
<212> TYPE: DNA
<213> ORGANISM: Artificial Sequence
<220> FEATURE:
<223> OTHER INFORMATION: synthesized nucleotide sequence

<400> SEQUENCE: 65
tcctcataca caggagtcca agcgtcagaa gtaaactctg cggagccata accgcgcaag    60
gacgcatcgt ggccggat                                                 78

<210> SEQ ID NO 66
<211> LENGTH: 78
<212> TYPE: DNA
<213> ORGANISM: Artificial Sequence
<220> FEATURE:
<223> OTHER INFORMATION: synthesized nucleotide sequence

<400> SEQUENCE: 66
aacactcgta tcggcttcac ttgcgcggtt atggctccgc agagtttact tctgacgctt    60
tggtgaccac gtcgtgga                                                 78

<210> SEQ ID NO 67
<211> LENGTH: 20
<212> TYPE: DNA
<213> ORGANISM: Homo sapiens

<400> SEQUENCE: 67
ggaagaggag acacggaaca                                               20

<210> SEQ ID NO 68
<211> LENGTH: 20
<212> TYPE: DNA
<213> ORGANISM: Homo sapiens

<400> SEQUENCE: 68
gcagctccag tgactacagc                                               20

<210> SEQ ID NO 69
<211> LENGTH: 21
<212> TYPE: DNA
<213> ORGANISM: Homo sapiens

<400> SEQUENCE: 69
```

```
gaggagacac ggaacaccaa g                                              21

<210> SEQ ID NO 70
<211> LENGTH: 20
<212> TYPE: DNA
<213> ORGANISM: Homo sapiens

<400> SEQUENCE: 70
gtcgcagcca atcatccact                                                20
```

ACTIVATION AND EXPANSION OF NKG2C+ NK CELLS

FIELD OF THE INVENTION

The invention relates to an isolated peptide for use as a medicament, wherein said peptide has 9 to 30 amino acids and comprises or consists of an amino acid sequence according to SEQ ID NO 1 (VMAPRTLXL), wherein X is an amino acid with a hydrophobic side chain (A, I, L, F, V, P, G), preferably V, L, I or F. The invention further relates to the peptide of the invention for use as a medicament to expand and/or activate NKG2C+ natural killer (NK) cells. The invention further relates to the peptide of the invention for use in the treatment and/or prevention of a medical condition associated with pathogenic cells expressing HLA-E and a peptide comprising an amino acid sequence according to SEQ ID NO 1 or 2. Additionally, the invention relates to a genetically modified virus encoding a peptide comprising or consisting of a polypeptide of the invention for use as a medicament to expand and/or activate NKG2C+ natural killer (NK) cells.

REFERENCE TO SEQUENCE LISTING

A Sequence Listing submitted as an ASCII text file via EFS-Web is hereby incorporated by reference in accordance with 35 U.S.C. § 1.52(e). The name of the ASCII 15 text file for the Sequence Listing is 30825745_1.TXT, the date of creation of the ASCII text file is Jun. 28, 2019, and the size of the ASCII text file is 14.0 KB.

BACKGROUND OF THE INVENTION

Natural killer (NK) cells are cytotoxic innate immune cells, which contribute to early immune responses against viral infections (1). Their role in host protection is highlighted by patients with primary NK-cell deficiencies, who suffer from severe and disseminated viral infections caused by herpesviruses such as human cytomegalovirus (HCMV) (2); and further supported by studies of the murine CMV (MCMV) infection model (3). HCMV has a high prevalence in the adult human population and establishes lifelong latency in healthy individuals. The host innate and adaptive immune systems jointly play a crucial role in restraining viral replication and preventing disease but do not eliminate the virus, which in turn engages in a dynamic interaction with the host, resulting in drastically imprinted immune-cell repertoires (4).

In accordance with these findings, Ly49H+ NK cells from C57BL/6 mice were shown to undergo expansion and adaptation in response to MCMV (3). Similarly, HCMV-seropositivity is associated with a skewed repertoire of human NK cells, and expression of the activating receptor CD94/NKG2C (NKG2C) marks a well characterized NK-cell subset adapted to HCMV infection, consequently termed 'adaptive NK cells' (5, 6, 7). Apart from NKG2C expression, adaptive NKG2C+ NK cells can be characterized by altered receptor profiles and remodeled epigenetic landscapes compared to conventional NK cells (5, 6, 7, 8, 9, 10, 11). In contrast to the murine infection model, in which the MCMV protein m157 was established as the ligand for Ly49H (12, 13), a HCMV ligand driving the specific expansion and differentiation of human NKG2C+ NK cells has not been identified.

The non-classical MHC class I molecule HLA-E serves as cognate ligand for NKG2C as well as its inhibitory counterpart CD94/NKG2A (NKG2A) (14, 15, 16) and has been reported to elicit effector functions in adaptive NKG2C+ NK cells (6) as well as to contribute to their expansion in vitro (17, 18). Cell surface stabilization of HLA-E requires loading with peptides, which can be derived from the signal sequences of MHC class I molecules (19) or other proteins such as HSP60 (20) at steady state. In addition to host peptides, the UL40 gene of HCMV was found to encode HLA-E-stabilizing peptides, which partially mimic MHC class I signal sequences (21, 22, 23, 24). Despite HCMV-mediated down-regulation of HLA class I to evade recognition by CD8+ T cells, UL40-derived peptides permit maintenance of HLA-E surface expression on infected cells and thereby preserve inhibition of NK-cell activation via engagement of NKG2A. Indeed, it was demonstrated that co-transfection of UL40 and HLA-E confers protection against NKG2A+ NK− cell lines and infection of fibroblasts with UL40-competent HCMV inhibits cytotoxic activity of NKG2A+ NK cells (21, 22, 23, 24).

However, whether NKG2C can recognize UL40 peptides during HCMV infection and result in activation of NKG2C+ NK cells remains completely unclear. HLA-E-stabilizing nonameric peptides derived from both MHC class I or UL40 share conserved residues at amino acids 2 and 9, while mutations at positions 5 and 8 have been shown to alter binding of HLA-E/peptide complexes to CD94 heterodimers with NKG2A or NKG2C in structural and biochemical analyses (25, 26, 27, 28, 29, 30). Conversely, analysis of peptide impacting on functional recognition of HLA-E-expressing cells by NKG2A and NKG2C has been confined to NK-cell clones (28, 29, 30). It was shown that CD94/NKG2C can be activated on an experimental cell line (Jurkat-NKG2C+ reporter cells) by HLA-E displaying cells that were pre-incubated with peptides VMAPRTLIL (SEQ ID NO. 3) or VMAPRTLFL (SEQ ID NO. 2) (Pupuleku A et al: "Elusive Role of the CD94/NKG2C NK Cell Receptor in the Response to Cytomegalovirus: Novel Experimental Observations in a Reporter Cell System", FRONTIERS IN IMMUNOLOGY, vol. 8, 24 Oct. 2017, (30)). These results demonstrate the general peptide-dependency of the interaction of CD94/NKG2 receptors with HLA-E. However, these articles provide no information about NKG2C receptor specificity towards peptides with single amino acid differences and effects of the peptides on, for example, NKG2A activation. They also do not assess the functional consequences of this peptide specificity in terms of cytokine production and most importantly the differential induction of proliferation and specific expansion of NKG2C+ NK cells by the different peptides. Furthermore, a medical application of the material and in particular the peptides is not described and no conclusions about their potential use can be based on the data of this article. The article completely focuses on experimentally determining activation of NKG2C in an artificial reporter system.

To which extent peptide recognition can impact on NK cell-mediated immune responses and whether distinct peptides can drive differential activation, expansion, differentiation, and heterogeneity of adaptive NKG2C+ NK cells during HCMV infection remain outstanding questions.

Infection with human cytomegalovirus (HCMV) is widespread in the general population, with the age-adjusted prevalence in Germany being around 30%. HCMV is a major cause of morbidity and mortality in immunocompromised individuals, especially patients undergoing hematopoietic stem cell transplantation (HSCT), which are at large risk for reactivating the virus with potentially lethal consequences. Importantly, the immune system of these patients is concomitantly challenged by HCMV and relapsing leukemia. Therefore, a strategy aimed at controlling both viral infection and leukemia relapse would be of great use.

Moreover, HCMV congenital infection is associated with microcephaly, mental disabilities and hearing problems. About 1 in 100 to 500 babies is born with congenital HCMV, and of the 10-20% symptomatic infections 30% are lethal, making this a large scale global health problem. Accordingly, large efforts have been invested into developing a vaccine against HCMV, but so far none of these approaches has been of success.

While large scale efforts in prevention and significant improvements in treatment strategies are bearing fruit in the last years by reducing both cancer incidence and mortality rates, especially advanced tumors still remain a challenge in modern medicine. Increasing lifespans in industrialized and developing countries mean that absolute incidence and mortality numbers are on the rise, which opens opportunities for developing more specific therapeutic approaches to treat subtypes of cancer. One particularly successful concept, which quite recently has found its way into the clinics with impressive results is cancer immunotherapy, with checkpoint inhibition being named the breakthrough of the year 2013. However, a great share of patients remains unresponsive to checkpoint inhibition for various reasons, and the widespread occurrence of autoimmunity further limits its use. One way to circumvent this is to target more specific tumor-associated ligands, as done by the recently FDA-approved CAR T cell therapy for B cell leukemia. In sum, the identification of new and more specific cancer immunotherapy targets bears great potential to develop new and improve current treatment regimens.

The use of HSP60-derived, HLA-E-binding nonameric peptides for the treatment of tumors has been described in WO 03/011895 A2. The invention described therein relates to modulation of CD94/NKG2 receptor function by HLA-E-bound peptides, which involves parallel modulation of activation NKG2A and NKG2C. However, as also disclosed in the context of the present invention, modifications of single amino acids of a HLA-E-binding peptide can have a tremendous impact on the activation of NK-cell receptors such as NKG2A and NKG2C, so that effects of a specific peptide cannot be extrapolated to apparently similar peptides that differ in one or more amino acids from the peptides of WO 03/011895 A2.

The innate lymphocytes Natural killer (NK) cells expressing the activating receptor CD94/NKG2C display adaptive features and are stably expanded in a group of individuals who have been infected with HCMV (41). It has been proposed that these cells have beneficial effects against HCMV reactivation (46). Importantly, correlation of reduced relapse rates in patients reactivating HCMV and presenting with NKG2C+ NK cell expansions has been reported, pointing towards an anti-leukemic effect of these cells highlighting their potential as an anti-cancer treatment (Cichocki et al. Leukemia. 2016; 30(2):456-63). However, an ex vivo expansion method for such protective CD56dim CD57+ NKG2C+ NK cells has not been described by Cichocki et al. and it is to be noted that ex vivo manipulation and expansion of NKG2C+ NK cells isolated form a donor probably has an impact on the overall character of the cells, such a modification of the epigenetic landscape, gene and surface marker expression, morphology and/or other characteristics, so that ex vivo expanded NKG2C+ NK cells most likely differ significantly from naturally occurring circulating NKG2C+ NK cells.

However, the means by which NKG2C+ NK cells can be expanded and activated by HCMV or cancer cells remain unclear, thus limiting their potential therapeutic use. WO2014037422A1 describes the ex vivo expansion of NKG2C+ NK cells for adoptive transfer. However, this approach raises severe concerns with respect to safe use of the cells, standardization of treatment and logistics. Besides this method bearing these significant disadvantages, there are no means known in the art to induce expansion and activation of NKG2C+ cells, in particular not for in vivo expansion and activation.

In light of the prior art, there remains a significant need to provide means for harnessing the therapeutic use of NKG2C+ cells in the treatment of HCMV infection and/or treatment of cancer.

SUMMARY OF THE INVENTION

In light of the prior art, the technical problem underlying the present invention is to provide alternative and/or improved means for expanding and/or activating NKG2C+ natural killer (NK) cells. A further problem to be solved is the provision of means for the treatment and/or prevention of a medical condition associated with pathogenic cells expressing HLA-E and a peptide comprising an amino acid sequence according to SEQ ID NO 1 or 2, such as HCMV infection or cancer.

The technical problem underlying the present invention is solved by the features of the independent claims. Preferred embodiments of the present invention are provided by the dependent claims.

The invention relates to an isolated peptide comprising or consisting of an amino acid sequence according to SEQ ID NO 1 (VMAPRTLXL), wherein X is an amino acid with a hydrophobic side chain (A, I, L, F, V, P, G), preferably V, L, I or F.

The invention further relates to an isolated peptide for use as a medicament comprising or consisting of an amino acid sequence according to SEQ ID NO 1 (VMAPRTLXL), wherein X is an amino acid with a hydrophobic side chain (A, I, L, F, V, P, G), preferably V, L, I or F. The invention preferably relates to an isolated peptide for use as a medicament, wherein said peptide has 9 to 30 amino acids and comprises or consists of an amino acid sequence according to SEQ ID NO 1 (VMAPRTLXL), wherein X is an amino acid with a hydrophobic side chain (A, I, L, F, V, P, G), preferably V, L, I or F.

The present invention is based on the entirely surprising finding that peptides of the present invention specifically induce the activation and expansion of NKG2C+ NK cells. In particular, presentation of the peptides of the present invention or fragments thereof on a non-classical MHC class I molecule, such as preferably HLA-E, leads to the activation of NKG2C+ NK cells resulting in expansion and/or activation of various effector functions such as induction of cell death of the cell presenting the peptide of the present invention on the non-classical MHC class I molecule, preferably HLA-E, and secretion and/or expression of TNF-alpha, IFN-gamma, CCL3 and/or CD107a. This was very surprising, since it had been reported that presentation of such peptides on HLA-E mainly display universal inhibitory effects on NK cells based on their binding to the inhibitory receptor NKG2A. Contrastingly, some of these peptides could induce preferential activation of NKG2C+ NK cells.

Furthermore, as disclosed herein, it was found out that the peptides of the invention have a specific activating effect on the subset of NKG2C+ NK cells, but not for example on NKG2C− NK cells. Additionally, the activating effect of the peptides of the invention was receptor specific, since blockage of the NKG2C/CD94 heterodimers almost completely inhibited the activating effect of the peptides of the present invention. Accordingly, the peptides of the invention can be applied in the context of the treatment of diseases associated with pathogenic cells expressing HLA-E and a peptide of the present invention.

Furthermore, it was entirely unforeseen that, even though the HLA-E binding peptides of the present invention do not differ from other peptides by their binding efficiency to HLA-E, the activation of NKG2C is peptide sequence specific. Indeed, other peptides, which bind to and stabilize HLA-E with equal efficiency as peptides of the present invention, lead to reduced or no selective activation of NKG2C+ NK cells. As shown in the example disclosed herein, single amino acid exchanges within peptides presented on HLA-E can be differentially recognized by adaptive NKG2C+ NK cells, resulting in differential activation of the cells. This finding was very surprising because, in contrast, NKG2A inhibition is less dependent on peptide sequence recognition and NKG2A+ NK cells are equally inhibited by recognition of HLA-E complexed with the peptides according to SEQ ID NO 1.

It was completely unexpected that the complexes formed by HLA-E and the peptides of the present invention engage differentially with CD94/NKG2C and lead to specific activation of this receptor complex on NK cells, whereas other receptors or receptor complexes that can interact with HLA-E, such as NKG2A, do not differentiate between specific peptide/HLA-E complexes. Accordingly, the present invention unexpectedly enables efficient, specific and selective activation of NKG2C+ NK cells. Surprisingly, the peptides of the present invention are comprised by the UL-40 protein of different HCMV strains as well as MHC Class I molecules, in particular the signal sequence of HLA-G. HLA-G is a non-classical MHC class I molecule absent in most healthy tissues and is mainly expressed during pregnancy and in certain cancer cells and is upregulated during inflammatory processes. Accordingly, the peptide of the present invention can be used in the context of treating diseases, which are associated with pathogenic cells, which express HLA-E and peptides comprising an amino acid sequence of a peptide of the present invention, for example cells expressing HLA-G or UL-40 of HCMV.

In preferred embodiments, the peptide of the invention consists of an amino acid sequence according to SEQ ID NO 2 (VMAPRTLFL). The peptide consisting of an amino acid sequence according to SEQ ID NO2 shows a particularly efficient effect with respect to activation and/or expansion of NKG2C+ NK cells.

In further embodiments, the peptide of the invention consists of an amino acid sequence according to SEQ ID NO 3 (VMAPRTLIL), SEQ ID NO 4 (VMAPRTLLL) or SEQ ID NO 5 (VMAPRTLVL).

Furthermore, the peptide of the present invention can be used as a medicament to expand and/or activate NKG2C+ natural killer (NK) cells in the treatment and/or prevention of a medical condition associated with pathogenic cells expressing HLA-E and a peptide comprising an amino acid sequence of a peptide of the invention.

This aspect of the invention is based on the surprising finding that cells presenting the complex formed by HLA-E and the peptide of the present invention on their surface are recognized by NKG2C+ NK cells through engagement of the complex with the CD94/NKG2C heterodimer. This leads to activation of the NKG2C+ NK cells resulting in secretion of several effector proteins and induction of cytotoxicity towards the cells presenting the complex. Such cells are in most cases pathogenic cells, such as tumor/cancer cells expressing HLA-G, comprising a peptide of the present invention in its leader/signal sequence, and HLA-E, or HCMV infected cells comprising actively replicating HCMV expressing UL-40. The pathogenic cells can be more efficiently fought by the immune system after recognition by NKG2C+ NK cells. Accordingly, provision of an increased number of NKG2C+ NK cells is beneficial for the treatment of disease associated with pathogenic cells expressing peptides comprising the amino acid sequence of a peptide of the present invention an HLA-E. Such an increased number of NKG2C+ NK cells can be provided or achieved by administration of the peptide of the present invention leading to in vivo expansion of the NKG2C+ NK cells, or administration of NKG2C+ NK cells of the present invention, which have been generated by the in vitro method of the present invention.

In embodiments, the isolated peptide of the invention is used as a medicament to expand and/or activate NKG2C+ natural killer (NK) cells.

Furthermore, the isolated peptide can be used in the treatment and/or prevention of a medical condition treatable by the cytotoxic activity of said NKG2C+ NK cells. Also, in embodiments, the isolated peptide is used as a medicament to expand and/or activate NKG2C+ natural killer (NK) cells in the treatment and/or prevention of a medical condition treatable by the effector function of said NKG2C+ NK cells.

In embodiments of the present invention, the peptide is used as a medicament to inhibit reactivation of human cytomegalovirus (HCMV) infections and/or reduce viral titers in an individual infected with HCMV. This embodiment is particularly relevant for the treatment of subjects, which are at risk of reactivation of HCMV or in which HCMV replication has been reactivated in some cells already, and wherein a spreading of the active infection should be prevented or suppressed.

In preferred embodiments of the invention, the peptide of the invention is used to treat cancer, wherein said cancer expresses HLA-G and HLA-E, preferably wherein the expression of HLA-G and HLA-E is above levels in healthy control cells, and wherein the cancer is preferably selected from the group consisting of leukemia, melanoma, choriocarcinoma, breast cancer, endometrial cancer, ovarian cancer, cervical cancer, esophageal squamous cell carcinoma, colorectal cancer, gastric cancer, hepatocellular carcinoma, glioblastoma, lung cancer, nasopharyngeal carcinoma, pancreatic adenocarcinoma, thyroid carcinoma and renal carcinoma.

The present invention is effective in the treatment of diseases associated with pathogenic cells that present peptides of the present invention on HLA-E on their surface. The non-classical MHC class I molecule HLA-G comprises the peptide of the invention in its signal sequence. HLA-G is expressed or upregulated in particular cancer cells. Such cancer cells can be identified by expression analysis of HLA-G and HLA-E, by various methods known to the person skilled in the art, some of which are also disclosed in the examples of the present patent application. Expression of HLA-G has been reported for several cancers, which are preferably treated with the peptide of the present invention, which comprise, without limitation, leukemia, Melanoma, choriocarcinoma, breast cancer, endometrial cancer, ovarian cancer, cervical cancer, esophageal squamous cell carcinoma, colorectal cancer, gastric cancer, hepatocellular carcinoma, glioblastoma, lung cancer, nasopharyngeal carcinoma, pancreatic adenocarcinoma, thyroid carcinoma and renal carcinoma. Cancers expressing HLA-G are known to the skilled person and are disclosed in the art (see for example Curigliano G, Criscitiello C, Gelao L, Goldhirsch A. *Molecular pathways: human leukocyte antigen G* (HLA-G). Clin Cancer Res. 2013; 19(20):5564-71; Lin A, Yan W H. *HLA-G expression in cancers: roles in immune evasion, metastasis and target for therapy*. Mol Med. 2015; Seliger B, Schlaf G. *Structure, expression and function of HLA-G in renal cell carcinoma*. Semin Cancer Biol. 2007; 17(6):444-50).

In embodiments of the invention, the peptide is used as a medicament to treat a cancer associated with expression of HLA-G and HLA-E, wherein the cancer is identified by
  a. providing a sample comprising cancer cells from a patient and
  b. determining expression of HLA-G and HLA-E in said sample.

Expression of HLA-G and HLA-E in cancer cells may be determined on the protein or the nucleic acid level. For example, mRNA expression levels of HLA-G and HLA-E encoding mRNA may be determined by qRT-PCR or sequencing analysis, as known to the person skilled in the art (see for example Paul, P., et al. (2000). "HLA-G, -E, -F preworkshop: tools and protocols for analysis of non-classical class I genes transcription and protein expression." Human Immunology 61(11): 1177-1195). Furthermore, expression may be analyzed on the protein level for example by cytometric analysis of HLA-G and HLA-E expression on the cells surface.

In embodiments, the isolated peptide of the invention is used as a medicament to treat a cancer associated with elevated expression of HLA-G compared to non-cancerous cells, preferably with elevated expression of HLA-G and HLA-E compared to non-cancerous cells, or a cancer susceptible to NKG2C+ NK cell cytotoxic activity. In the context of the method of the invention, the expression level of HLA-E and/or HLA-G determined in a sample comprising cancer cells from a subject may be compared to the expression of HLA-E and/or HLA-G in a reference standard sample (as in the disclosed example) and/or in a corresponding sample isolated from a healthy individual, and/or in a corresponding sample that does not comprise cancer cells. A corresponding sample may be a sample that has been isolated form the same tissue or bodily fluid, but does not comprise any cancer cells, for example because it has been isolated from a healthy individual.

In embodiments, the peptide of the invention is used as a medicament to treat a cancer associated with elevated expression of HLA-G and HLA-E. In further embodiments, the peptide of the invention is used as a medicament to treat a cancer susceptible to NKG2C+ NK cell cytotoxic activity.

In a preferred embodiment of the invention, the peptide is used as a medicament to treat leukemia and inhibit reactivation of HCMV infections in subjects having received hematopoietic stem cell transplantation (HSCT). The activation and expansion of NKG2C+ NK cells by peptides of the present invention may be particular advantageous in the context of HSCT, because NK cells are among the first lymphocyte populations to recover after transplantation and therefore can be targeted by the using the approach of the present invention, thus potentially protecting against HCMV reactivation and tumor relapse in leukemia patients after HSCT.

In a further preferred embodiment of the invention the peptide is administered in combination with an adjuvant, preferably selected from an adjuvant enhancing production of or comprising IL-15, IL-12 and/or IL-18. In embodiments, the peptide of the invention is administered in combination with IL-15, IL-12 and/or IL-18. In preferred embodiments, the adjuvant is inducing or enhancing the production of pro-inflammatory cytokines.

In embodiments, the peptides of the present invention are administered in combination with one or more pro-inflammatory cytokines. It was surprising, that combined stimulation of NKG2C+ NK cells with the complex consisting of HLA-E and the peptide of the present invention and pro-inflammatory cytokines, such as for example IL-15, IL-12 and/or IL-18, induces accumulation of NKG2C+ NK cells, also of NK cells from or in HCMV-individuals.

In preferred embodiments of the invention, the peptide is administered in combination with a check point inhibitor, preferably an inhibitor of an inhibitory receptor selected from the group comprising LILRB1, inhibitory KIRs, NKG2A, PD-1, CTLA-4, TIM-3, TIGIT and LAG-3. Check point inhibitors have gained a lot of attention in the context of cancer treatment, since it turned out that the inhibition or blockage of inhibitory receptors expressed by immune cells and in particular immune effector cells, such as for example T cells, but also NK cells, enables robust activation of the effector cells to elicit an effective immune response against for example cancer cells. This is due to the fact that in many pathological conditions, especially cancer and viral infections, the pathogenic cells prevent an effective immune response by activating inhibitory receptors on immune cells, thereby preventing an effector response of the immune system against the pathogenic cells. However, check point inhibitors make it possible to overcome this pathological mechanism by preventing activation of the inhibitory receptors and therefore enabling and potentiating the activation of an effective immune response against the pathogenic cells.

In the context of the present invention, it turned out that combined administration of the peptides of the present invention together with inhibitors of check point molecules, in particular check point molecules that are expressed by NK cells, such as for example LILRB1, inhibitory KIRs, NKG2A, PD-1, CTLA-4, TIM-3, TIGIT and LAG-3, potentiates the activating effect of the peptides of the present invention on NKG2C+ NK cells. Preferably, such a combined administration may be carried out in the context of the treatment of cancer and HCMV infection.

In a preferred embodiment of the present invention, the peptide is administered in combination with an activator of the co-stimulatory receptor CD2. It can be advantageous to use the peptides of the present invention in combination with an activator or stimulator of CD2, which can act as a co-stimulatory receptor on NK cells and particularly on NKG2C+ NK cells, since surprisingly the combined activation leads to an enhanced poly-functional response of the NKG2C+ NK cells including activation of cytotoxic activity as well as secretion of inflammatory mediators such as CCL3, CD107a, IFN-gamma and TNF-alpha, which cannot be explained by the addition of the individual effects of the peptides and the CD2-activators, but instead argue for the presence of a synergistic effect. Accordingly, the engagement of the co-stimulatory receptor CD2 can lower the activation threshold of NKG2C+ NK cells by the peptides of the present invention and therefore enable the peptides of the present invention to optimally trigger multiple effector functions in adaptive NKG2C+ NK cells.

Further embodiments of the invention relate to administration of the peptide in combination with IFN-alpha. IFN-alpha is known to trigger antiviral NK-cell functions and in the context of the present invention it was found that the combined administration of the peptides of the invention and IFN-alpha leads to an enhanced differential activation of NKG2C+ NK cells.

In embodiments of the invention, the peptide for use as a medicament is administered by a vector comprising or encoding the peptide of the present invention.

This embodiment relates to the use of viral vectors or other vectors, such as mammalian or prokaryotic cells or DNA molecules, such as plasmids, which may be comprised in liposomes or other suitable formulation for administration. The vectors used herein may comprise the peptide of the invention. For example, a viral vector comprising the proteins or peptides with the amino acid sequence of the peptides of the invention may be administered. Furthermore, cells expressing such peptides may be used as a vector. Alternatively, the peptides are not present in the vector at the time of administration. However, the vector may enable expression of the peptide of the invention upon delivery to the host, such as a patient suffering from HCMV or cancer, wherein expression of the peptide is induced after administration. For example, a cell carrying an exogenous nucleic acid molecule comprising a sequence encoding the peptide of the present invention under the control of a constitutive or inducible promoter may be used as a vector to provide expression of the peptides of the invention in a subject after administration of the cells.

Similarly, a viral vector may be used to infect cells of a subject or patient in need of activation of NKG2C+ NK cells. The viral vector may comprise a nucleic acid molecule which enables expression of the peptide of the invention in by a cell of the subject upon infection with the viral vector. Alternatively, an exogenous nucleic acid molecule, such as a DNA plasmid, may be administered to a subject in need of activation of NKG2C+ NK cells, for example by means of a liposomal formulation, enabling delivery of the plasmid to a host cell of the subject, which subsequently expresses the peptide of the present invention. The person skilled in the art is aware of further suitable vectors and means of administering such vectors comprising or encoding the peptide of the present invention.

In embodiments of the invention, the peptide is encoded by a nucleic acid molecule operably linked to a promoter for expression in mammalian, preferably human subjects. In further embodiments, the nucleic acid molecule is a recombinant nucleic acid molecule. It is particularly advantageous to use nucleic acid molecules comprising promoters for expression of the peptide of the invention in cells of the subject in need NKG2C+ NK cell activation, since it is possible to provide a source of renewed production of the peptide of the present invention the subject with a single administration. Use of a recombinant nucleic acid is advantageous, since the peptide expression can be controlled by a suitable promoter or promoter/enhancer combination, which is specifically selected and suitable for the specific application. It is possible to use controllable promoters, to be able to control expression levels of the peptides of the invention.

According to embodiments of the invention, the vector is a genetically modified virus selected from the group comprising attenuated HCMV, vaccinia virus, adenovirus, adeno-associated virus, retrovirus, or lentivirus.

The present invention also relates to an in vitro method for cultivating and/or expanding NKG2C+ natural killer (NK) cells, said method comprising:
  providing leukocyte cells from a donor, wherein said leukocytes comprise NK cells;
  contacting said NK cells with a peptide of the present invention; and
  optionally isolating or enriching for NKG2C+ NK cells.

Preferably, the method of the present invention comprises contacting the NK cells with IL-15, IL-12 and/or IL18. Furthermore, the cells may be contacted with an activator of CD2, such as LFA-3. In the context of the method of the invention, contacting the cells with an agent may relate to stimulation of the cells in cell culture, for example by adding the respective agent to the cell culture medium.

In embodiments, the leukocytes are purified CD56dim NK cells, which may be characterized as CD56dim NKG2A− CD57+ NKG2C+ or NKG2A− CD57+ KIR+ NKG2C+ NK cells. The leukocyte cells may be contacted in cell culture with murine TAP-deficient RMA-S cells transfected with human β2-microglobulin and HLA-E (RMA-S/HLA-E). Furthermore, the RMA-S/HLA-E may be transfected with human LFA-3 (RMA-S/HLA-E/LFA-3). The leukocyte cells may also be contacted with human K562 cells transfected with HLA-E (K562/HLA-E). The RMA-S/HLA-E, RMA-S/HLA-E/LFA-3 and/or K562/HLA-E may be pulsed with a peptide of the present invention and/or the peptide of the invention may be added to the cell culture directly.

The provision of IL-12 and/or IL-18 is particularly advantageous in the context of the in vitro method of the present invention since the presence of these cytokines in the culture medium specifically accelerates proliferation of NKG2C+ NK cells, therefore leading to an expansion and competitive selection of the cells in comparison to other cells present in the cell culture. As shown in the example disclosed herein, the provision of pro-inflammatory cytokines during the initial phase of culture resulted in dramatically accelerated NKG2C+ NK-cell division induced by the peptide of the present invention.

The in vitro method of the invention may be used to generate large amounts of patient specific NKG2C+ NK cells ex vivo/in vitro. These cells may be used for various purposes, such as for example experimental use, screenings for example for the effectiveness of compounds, such as drug candidates, and therapeutic use. For example, the ex vivo expanded cells may be administered to a patient, either as an autologous or allogenic transplant, wherein the cells may be genetically modified or not.

Furthermore, the present invention also relates to an isolated population of NKG2C+ natural killer (NK) cells produced by the in vitro method of the present invention. The cells produced by the method of the present invention display specific characteristics, which make them suitable and preferable for certain applications, including therapeutic applications such as administration to patients in need of NKG2C+ NK cells. Such patients may suffer from a condition associated pathogenic cells expressing HLA-E and a peptide comprising a sequence of the peptide of the present invention, such as for example an HCMV infection or cancer, wherein said cancer expresses HLA-G and HLA-E.

The cells of the present invention may be characterized by a specific expression pattern and profile with respect to one or more of the markers selected from the group comprising SIGLEC7, CD7, SYK, CD2, LILRB1 (LIR-1/ILT2), NCR3 (NKp30), SH2DB1 (EAT2) and ZBTB32 (PLZP), ZBTB16 (PLZF), ZBTB20, ITGAL, CRTAM, HLA-DR, TNFRSF9 (4-1 BB), LAG3, CTLA4, and PDCD1 (PD1) as well as of effector functions including IFNG, TNF, CCL3, CCL4, IL8, CSF2, IL10, GZMB, and TNFSF10 (TRAIL).

In particular, the cells of the invention may be characterized by an up-regulation of one or more activation and exhaustion markers, such as HLA-DR, TNFRSF9 (4-1BB), LAG3, CTLA4, PDCD1 (PD1), and of effector functions, such as IFNG, TNF, CCL3, CCL4, IL8, CSF2, IL10, GZMB, and TNFSF10 (TRAIL) compared to NK cells expanded in the absence of peptides of SEQ ID NO 1 and of IL-12 and IL-18.

In particular, the cells of the invention may be characterized by the epigenetic DNA demethylation of effector cytokine genes, such as but not limited to IFNG, as in the disclosed example.

It is a particular advantage of the in vitro method of the present invention that the resulting expanded NK cells of the present invention adapt an NKG2C+ NK cells phenotype in comparison to NK cells expanded according to methods known in the art, since NKG2C+ NK cells and also the cells of the present invention are particularly beneficial for use in adoptive transfer and other therapeutic approaches in patients suffering from conditions associated with pathogenic cells expressing HLA-E and a peptide comprising an amino acid sequence according to the peptides of the present invention. The cells of the present invention can be identified by specific remodeling of the epigenetic landscape, for example the DNA methylation state of specific effector genes, and/or by specific gene expression patterns with respect to activation and exhaustion markers, effector functions and further markers of NK cells and NK cell subsets. In embodiments of the invention, the isolated population of NKG2C+ NK cells or the invention are for use as a medicament to treat and/or prevent a medical condition associated with pathogenic cells expressing HLA-E and a peptide of the present invention, preferably a cancer associated with expression of HLA-G and HLA-E.

Furthermore, the invention relates to a genetically modified virus encoding a peptide comprising or consisting of a polypeptide of the present invention for use as a medicament to expand and/or activate NKG2C+ NK cells in the treatment and/or prevention of a medical condition associated with pathogenic cells expressing HLA-E and a peptide of the present invention.

The preferred embodiments and associated advantages of the peptide of the present invention for use as a medicament also relate to the method and the cells of the present invention, and the other way around.

BRIEF DESCRIPTION OF THE DRAWINGS

The invention is further described by the following figures. These are not intended to limit the scope of the invention, but represent preferred embodiments of aspects of the invention provided for greater illustration of the invention described herein.

BRIEF DESCRIPTION OF THE FIGURES

Figure 1:
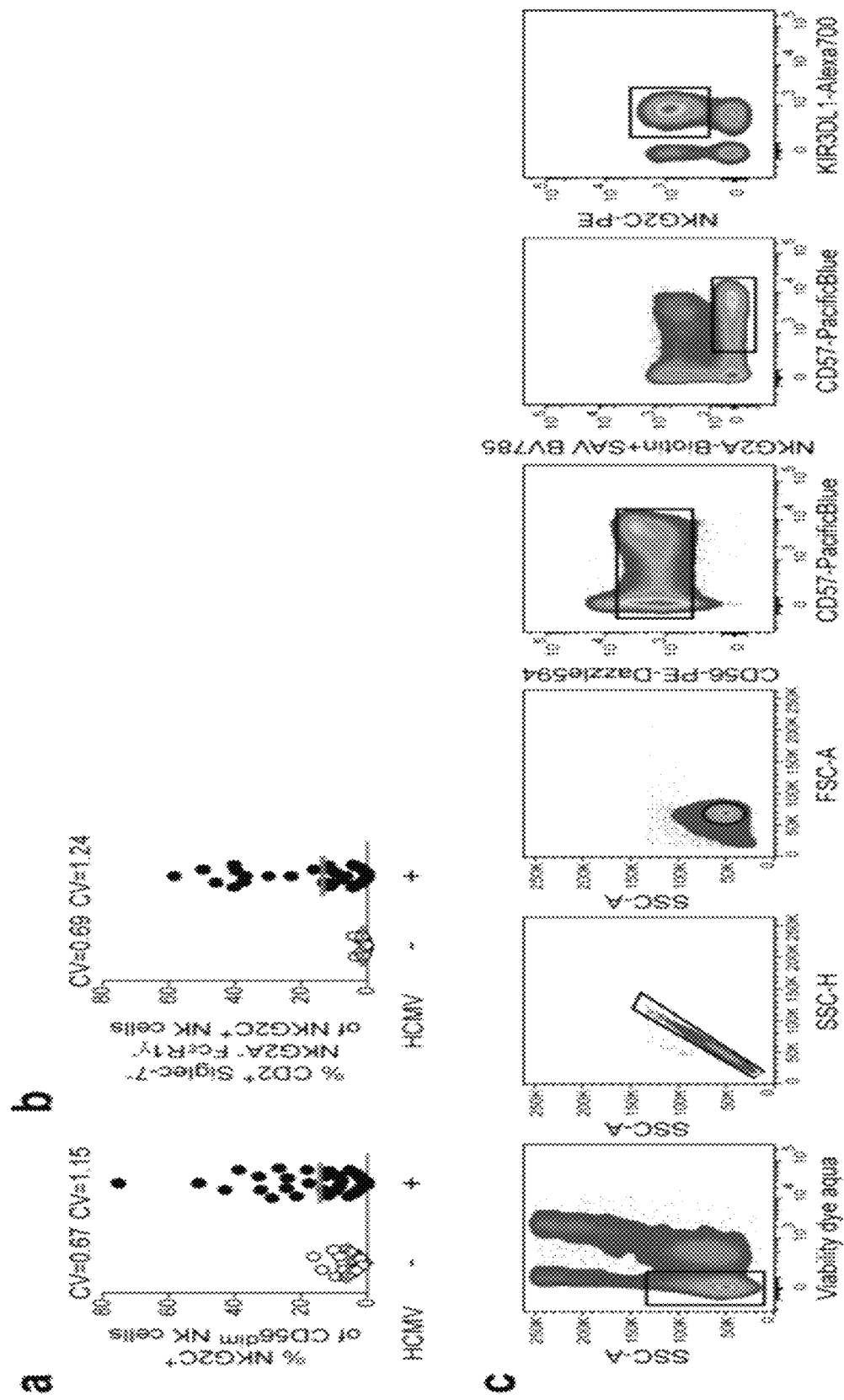
Figure 1:
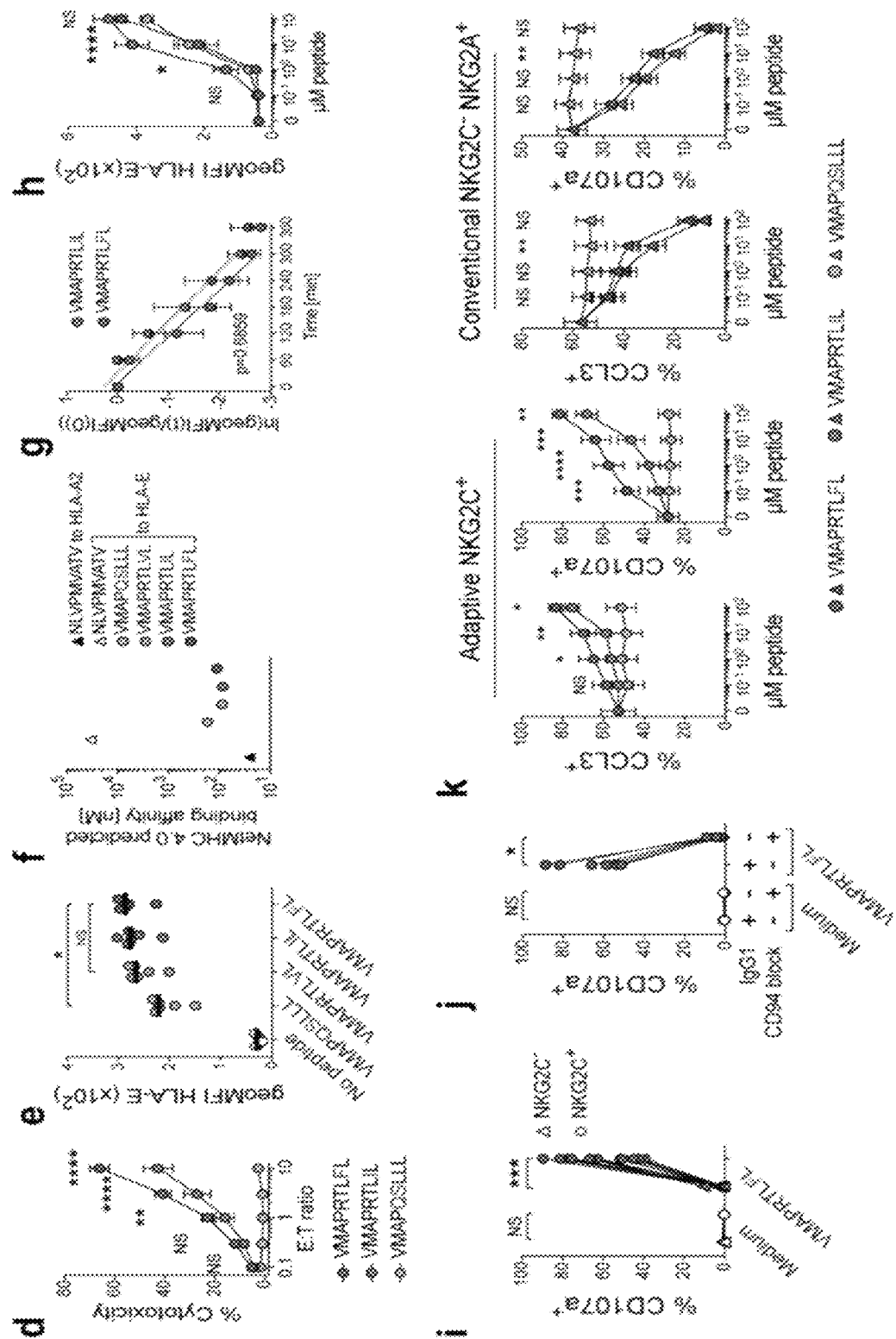

FIG. 1. Sequence Variations in HCMV UL40-Encoded Peptides Control the Activation of Adaptive NKG2C+ NK Cells but Do Not Differentially Affect Inhibition of NKG2C− NKG2A+ NK Cells. (a-b) PBMC of healthy HCMV− (n=20) and HCMV+ (n=40) individuals were screened by flow cytometry. (a) Frequency of NKG2C+ cells within the CD56dim population and (b) frequency of CD2+ Siglec-7− NKG2A− FcεR1g− cells within the CD56dim NKG2C+ population. CV, coefficient of variation. Symbols indicate individual donors and lines median. (c) Gating strategy for functional assays using HCMV+ donors with adaptive NKG2C+ NK cells. After culture of purified viable CD3− CD56+NK cells with peptide-pulsed target cells, adaptive NKG2C+ NK cells were gated as viable single CD56dim NKG2A− CD57+ KIR+ NKG2C+ cells. Depending on the phenotype of the individual donor, KIR were gated as KIR2DL1+, KIR2DL3+ or KIR3DL1+ (d) Purified NK cells from HCMV+ donors were used as effector cells in cytotoxicity assays against labelled peptide-pulsed RMA-S/HLA-E and % cytotoxicity was calculated as described in the Methods section. Symbols and error bars indicate mean±SEM (n=individual donors in 3 independent experiments). Two-way repeated-measure ANOVA with Bonferroni correction between VMAPRTLIL (SEQ ID NO. 3) and VMAPRTLFL (SEQ ID NO. 2). (e) RMA-S/HLA-E were pulsed with 300 μM of the indicated peptides and geometric mean fluorescence intensity (geoMFI) of HLA-E surface expression was detected (n=6 independent experiments). Horizontal lines depict median. Friedman test with Dunn's post test. (f) Binding affinities were predicted using the NetMHC4.0 algorithm. The HCMV pp65-derived HLA-A2-restricted NLVPMVATV peptide serves as a non-HLA-E-binding control. (g) RMA-S/HLA-E were pulsed with 300 μM VMAPRTLIL (SEQ ID NO. 3) or VMAPRTLFL (SEQ ID NO. 2) peptide followed by removal of peptide and chase for 6 h. Decay in HLA-E surface expression was calculated assuming first order kinetics (n=3 independent experiments) and slopes compared using ANCOVA. (h) RMA-S/HLA-E were pulsed with increasing concentrations of the indicated peptides and geoMFI of HLA-E surface expression upon pulsing is displayed. Symbols and error bars indicate mean±SEM (n=6 independent experiments). (i) Degranulation response of viable CD56dim NKG2C− (triangles) or viable CD56dim NKG2A− CD57+ KIR+ NKG2C+ NK cells (circles) upon culture without or with VMAPRTLFL (SEQ ID NO. 2)-pulsed RMA-S/HLA-E. Connected symbols represent individual donors (n=12 in 6 experiments). Two-tailed Wilcoxon test. (j) Sorted viable CD56dim NKG2A− NKG2C+ NK cells from HCMV+ donors were treated with IgG1 isotype control or anti-CD94 blocking antibody prior to culture without or with VMAPRTLFL (SEQ ID NO. 2)-pulsed RMA-S/HLA-E. Summary of degranulation of viable CD56dim NKG2A− CD57+ NKG2C+ NK cells is depicted. Connected symbols represent individual donors (n=6 in 3 independent experiments). Two-tailed Wilcoxon test. (k) Purified NK cells from HCMV+ donors were cultured with K562/HLA-E pulsed with indicated peptides at indicated concentrations. Summary of effector functions gated on viable CD56dim NKG2A− CD57+ KIR+ NKG2C+ NK cells (circles) or CD56dim NKG2C− NKG2A+ cells (triangles). Symbols and error bars indicate mean±SEM (n=6 individual donors in 3 independent experiments). Two-way repeated-measures ANOVA with Bonferroni correction between VMAPRTLIL (SEQ ID NO. 3) and VMAPRTLFL (SEQ ID NO. 2). NS not significant, *p<0.05, p<0.01, *p<0.005, ****p<0.0001.

Figure 2:
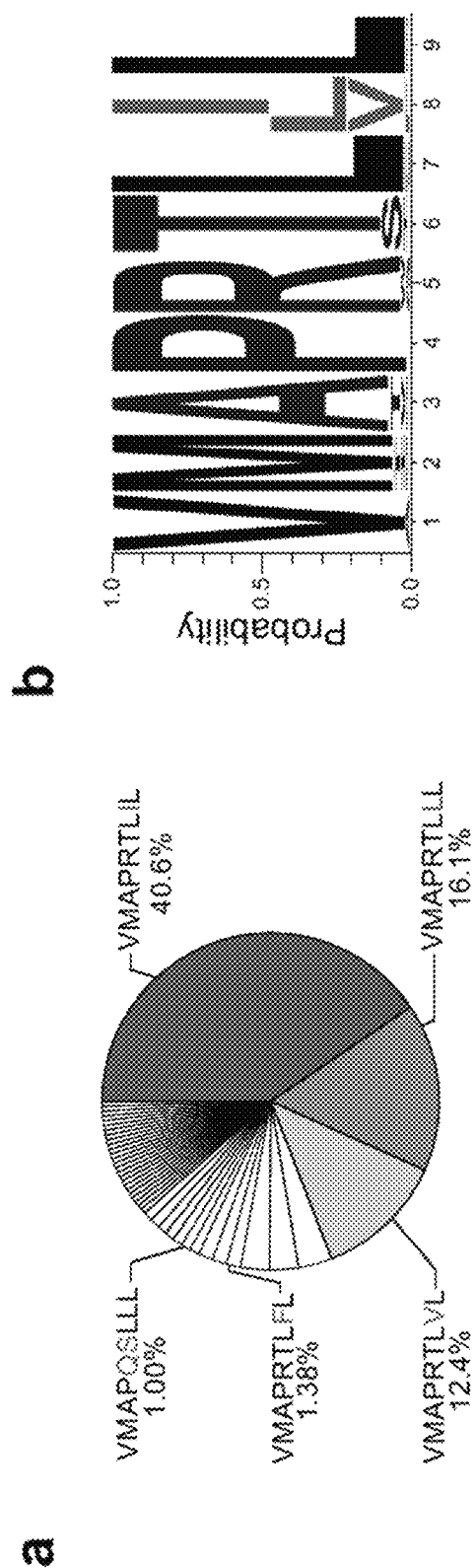
Figure 2:
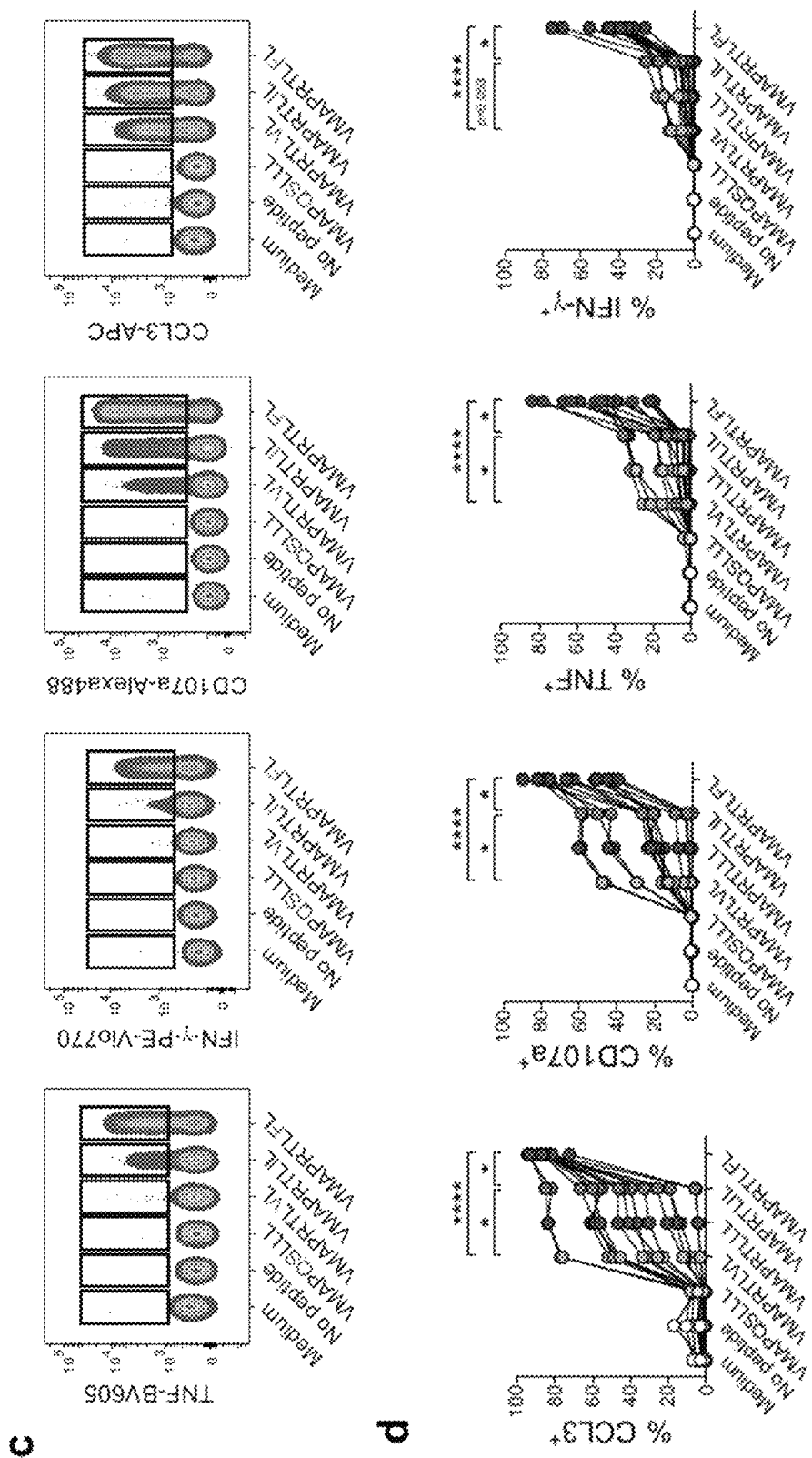
Figure 2:
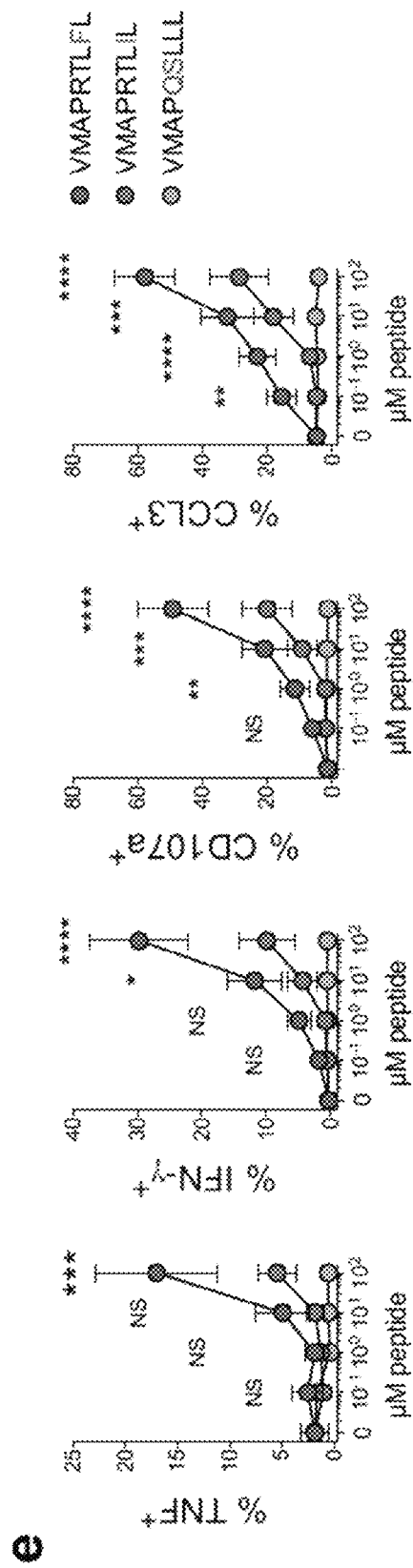

FIG. 2. Sequence Variations in HCMV UL40-Encoded Peptides Control the Activation of Adaptive NKG2C+ NK Cells. (a-b) Integrated analysis of 165 published and 52 newly determined HCMV UL40 sequences (VMAPRTLXL (SEQ ID NO: 1); VMAPRTLFL (SEQ ID NO: 2); VMAPRTLIL (SEQ ID NO: 3); VMAPRTLLL (SEQ ID NO: 4); VMAPRTLVL (SEQ ID NO: 5); and VMAPQSLLL (SEQ ID NO: 12). (a) Repertoire of peptide sequences and (b) sequence logo (n=217 sequences). (c-d) Purified NK cells from HCMV+ donors were cultured with RMA-S/HLA-E pulsed with indicated peptides. (c) Representative FACS stainings and (d) summary of effector functions gated on viable CD56dim NKG2A− CD57+ KIR+ NKG2C+ NK cells (FIG. 1c for gating strategy). Symbols represent individual donors (n=15 in 8 independent experiments) and lines median. Friedman test with Dunn's post test. (e) Purified NK cells from HCMV+ donors were cultured RMA-S/HLA-E pulsed with increasing concentrations of the indicated peptides. Summary of effector functions gated on viable CD56dim NKG2A− CD57+ NKG2C+ NK cells. Symbols and error bars indicate mean±SEM (n=6 individual donors in 3 independent experiments). Two-way repeated-measure ANOVA with Bonferroni correction between VMAPRTLIL (SEQ ID NO. 3) and VMAPRTLFL (SEQ ID NO. 2). NS not significant, *p<0.05, p<0.01, *p<0.001, ****p<0.0001.

Figure 3:
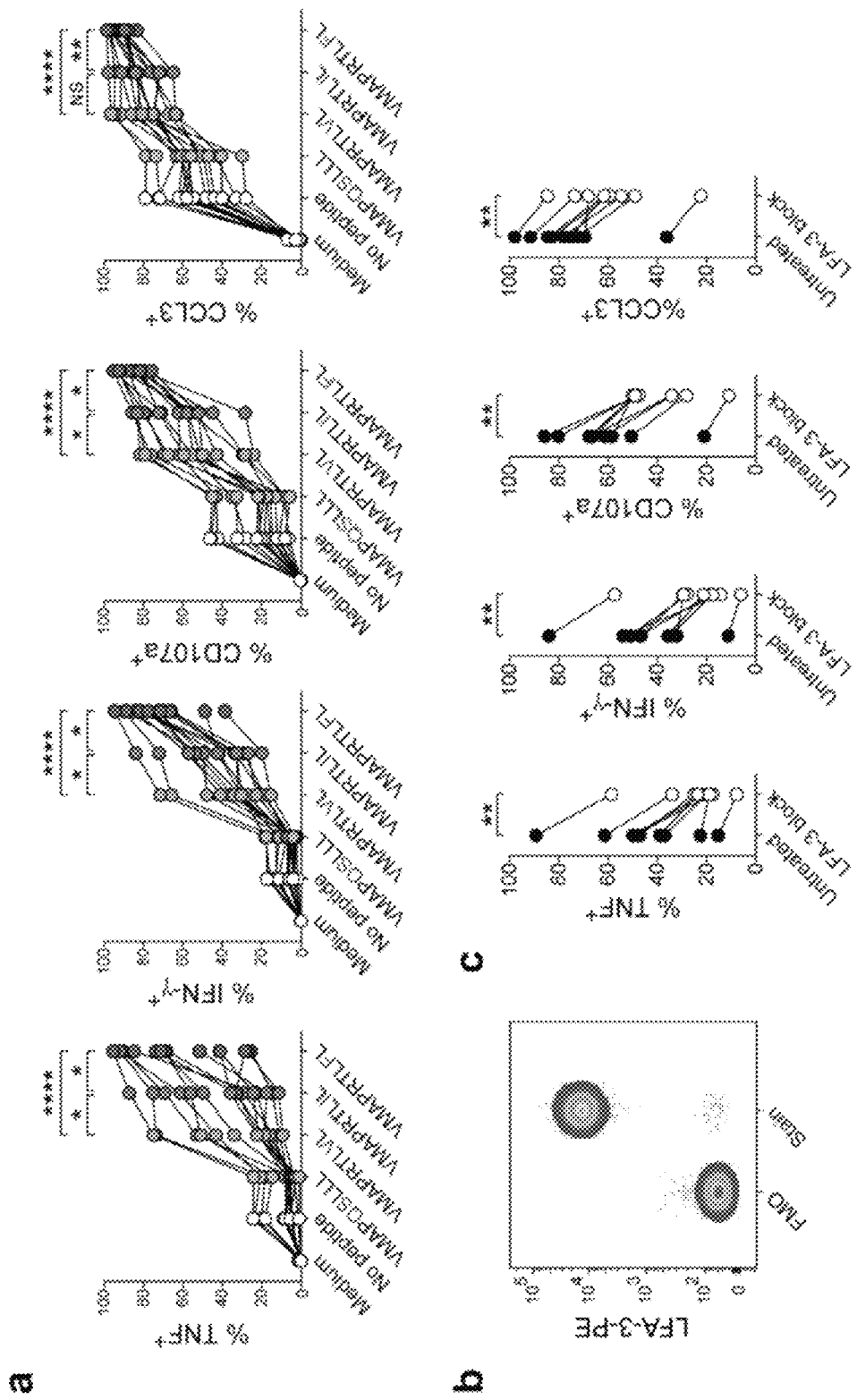

FIG. 3. Co-Stimulation via LFA-3 Enhances Functional Responses of Adaptive NKG2C+ NK Cells. HCMV UL40 sequences: VMAPRTLFL (SEQ ID NO: 2); VMAPRTLIL (SEQ ID NO: 3); VMAPRTLVL (SEQ ID NO: 5); and VMAPQSLLL (SEQ ID NO: 12). (a) Purified NK cells from HCMV+ donors were cultured with K562/HLA-E pulsed with indicated peptides. Summary of effector functions gated on viable CD56dim NKG2A− CD57+ KIR+ NKG2C+ NK cells. Symbols indicate individual donors (n=15 in 8 independent experiments) and lines median. Friedman test with Dunn's post test. (b) K562/HLA-E were examined for the expression of LFA-3 by flow cytometry. Fluorescence minus one (FMO) control and stained condition gated on viable cells. (c) Purified NK cells from HCMV+ donors were either left untreated or treated with blocking anti-LFA-3 followed by stimulation with VMAPRTLIL (SEQ ID NO. 3)-pulsed K562/HLA-E. Effector functions gated on viable CD56dim NKG2A− CD57+ KIR+ NKG2C+ NK cells. Connected symbols represent individual donors (n=9 in 5 independent experiments). Two-tailed Wilcoxon test. *p<0.05, p<0.01, **p<0.0001.

Figure 4:
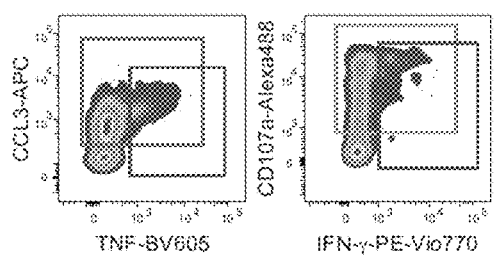
Figure 4:
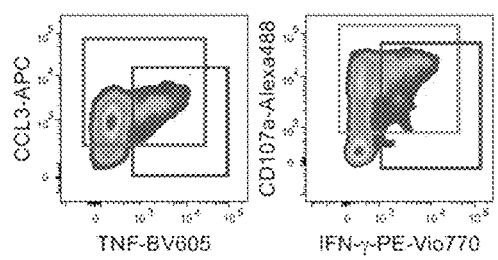
Figure 4:
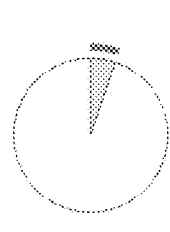
Figure 4:
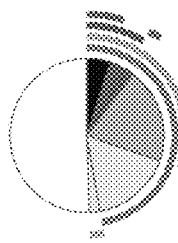
Figure 4:
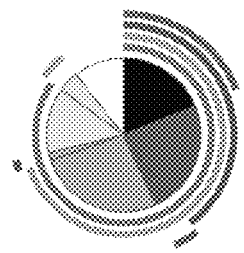
Figure 4:
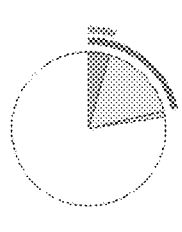
Figure 4:
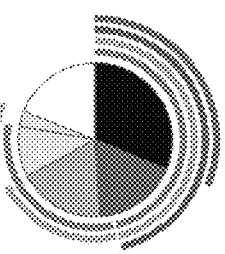
Figure 4:
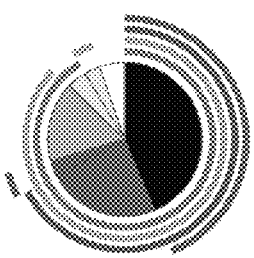
Figure 4:
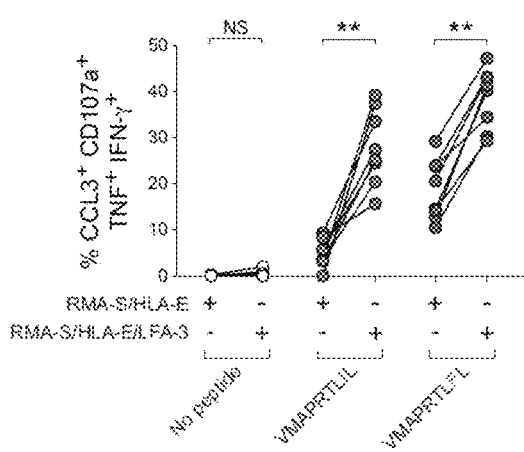
Figure 4:
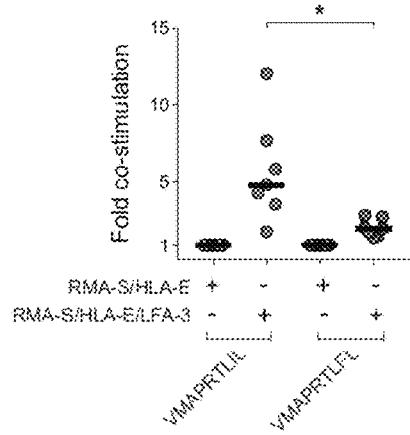

FIG. 4. Co-Stimulatory Signals Are Required to Elicit Polyfunctionality of Adaptive NKG2C+ NK Cells Upon Engagement with Sub-Optimal Peptides; HCMV UL40 sequences: VMAPRTLFL (SEQ ID NO: 2); and VMAPRTLIL (SEQ ID NO: 3). (a-d) Purified NK cells from HCMV+ donors were cultured with peptide-pulsed RMA-S/HLA-E or RMA-S/HLA-E/LFA-3. (a) Representative co-expression of CCL3 and TNF as well as CD107a and IFN-γ upon stimulation with VMAPRTLIL (SEQ ID NO. 3)-pulsed RMA-S/HLA-E (left) or RMA-S/HLA-E/LFA-3 (right). Gated on viable CD56dim NKG2A− CD57+ KIR+ NKG2C+ NK cells. (b) SPICE charts depict pattern of 0 to 4 functions consisting of combinatorial expression of CCL3, CD107a, IFN-γ, and TNF gated on viable CD56dim NKG2A− CD57+ KIR+ NKG2C+ NK cells. Pies and arcs.

Figure 5:
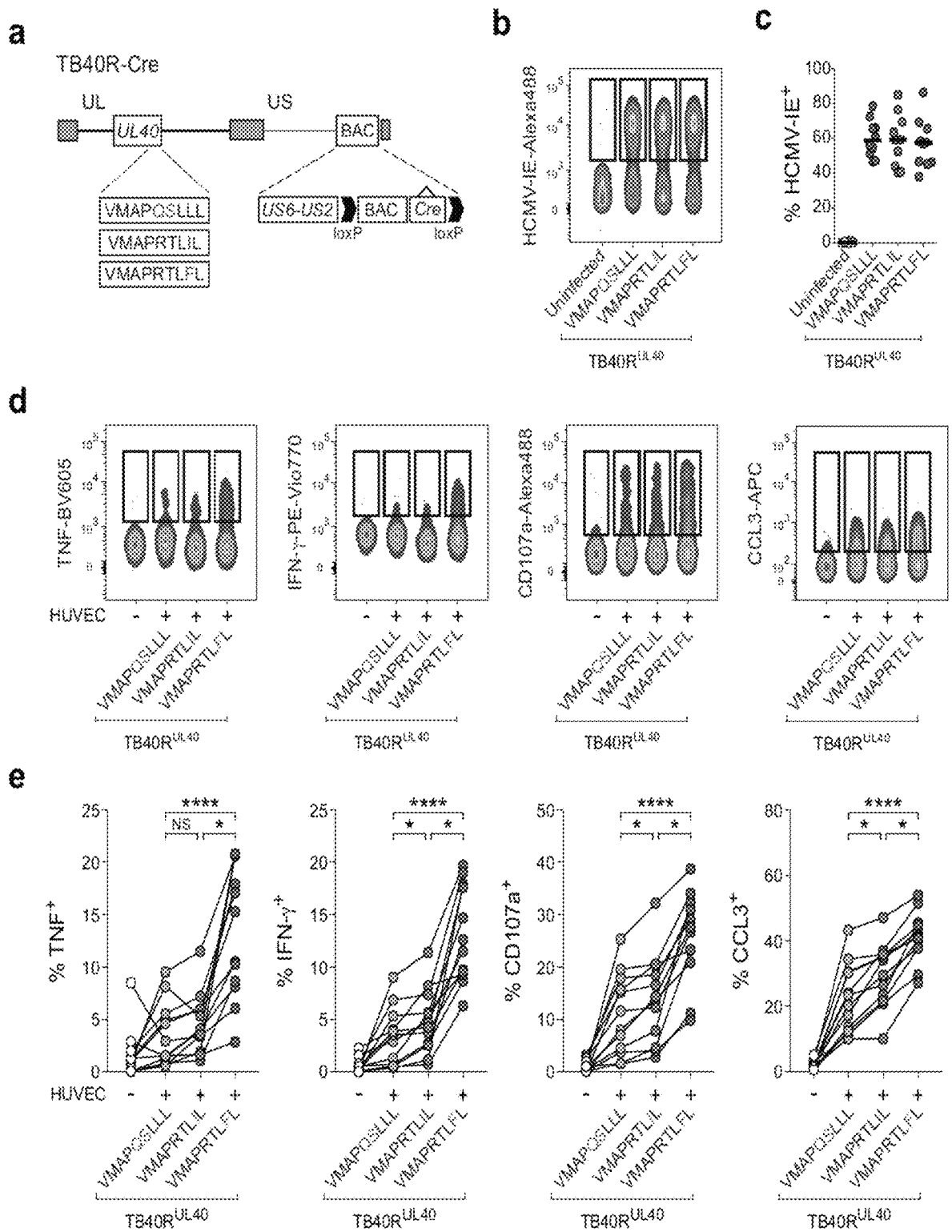

FIG. 5. Adaptive NKG2C+ NK Cells Differentially Recognize HCMV-Encoded Peptides during Infection. HCMV UL40 sequences: VMAPRTLFL (SEQ ID NO: 2); VMAPRTLIL (SEQ ID NO: 3); and VMAPQSLLL (SEQ ID NO: 12). (a) US2-6 genes were re-inserted into TB40 BAC4 to generate repaired TB40 (TB40R) and nucleotide variations were introduced within the UL40 sequence to encode the indicated peptides. (b-c) HUVEC were either left uninfected or infected with TB40R mutants. (b) Representative FACS staining of HCMV immediate early antigen (HCMV-IE) in viable HUVEC 48 hours post infection and (c) summary of infection rates. Symbols represent independent experiments (n=10) and lines median. (d-e) Purified NK cells from HCMV+ donors were overnight primed with IFN-α, followed by culture in medium or with virus-infected HUVEC. (d) Representative FACS staining and (e) summary of effector functions gated on viable CD56dim NKG2A− CD57+ KIR2DL1− KIR3DL1− KIR2DL3+ NKG2C+ NK cells. Connected symbols represent individual donors (n=12 in 3 independent experiments). Friedman test with Dunn's post test. NS not significant, *p<0.05, ****p<0.0001.

Figure 6:
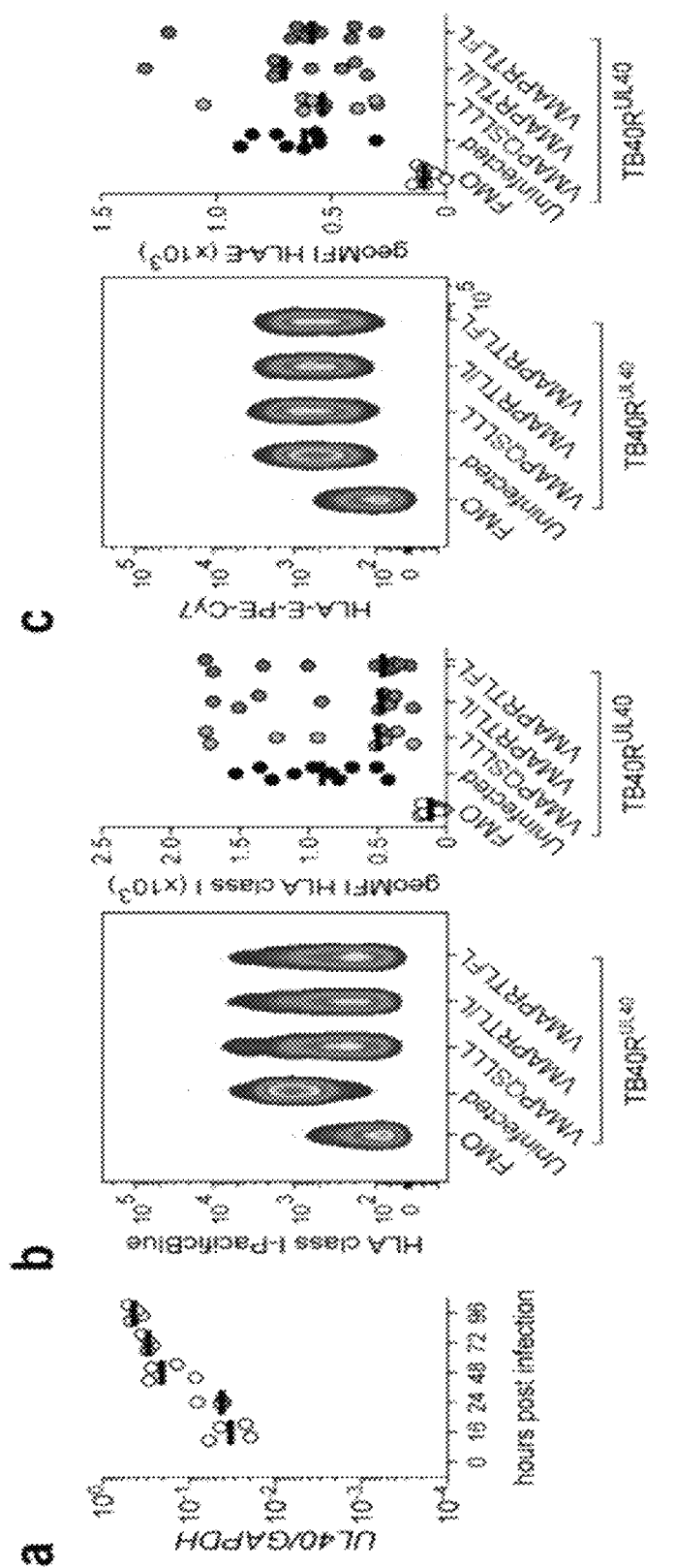
Figure 6:
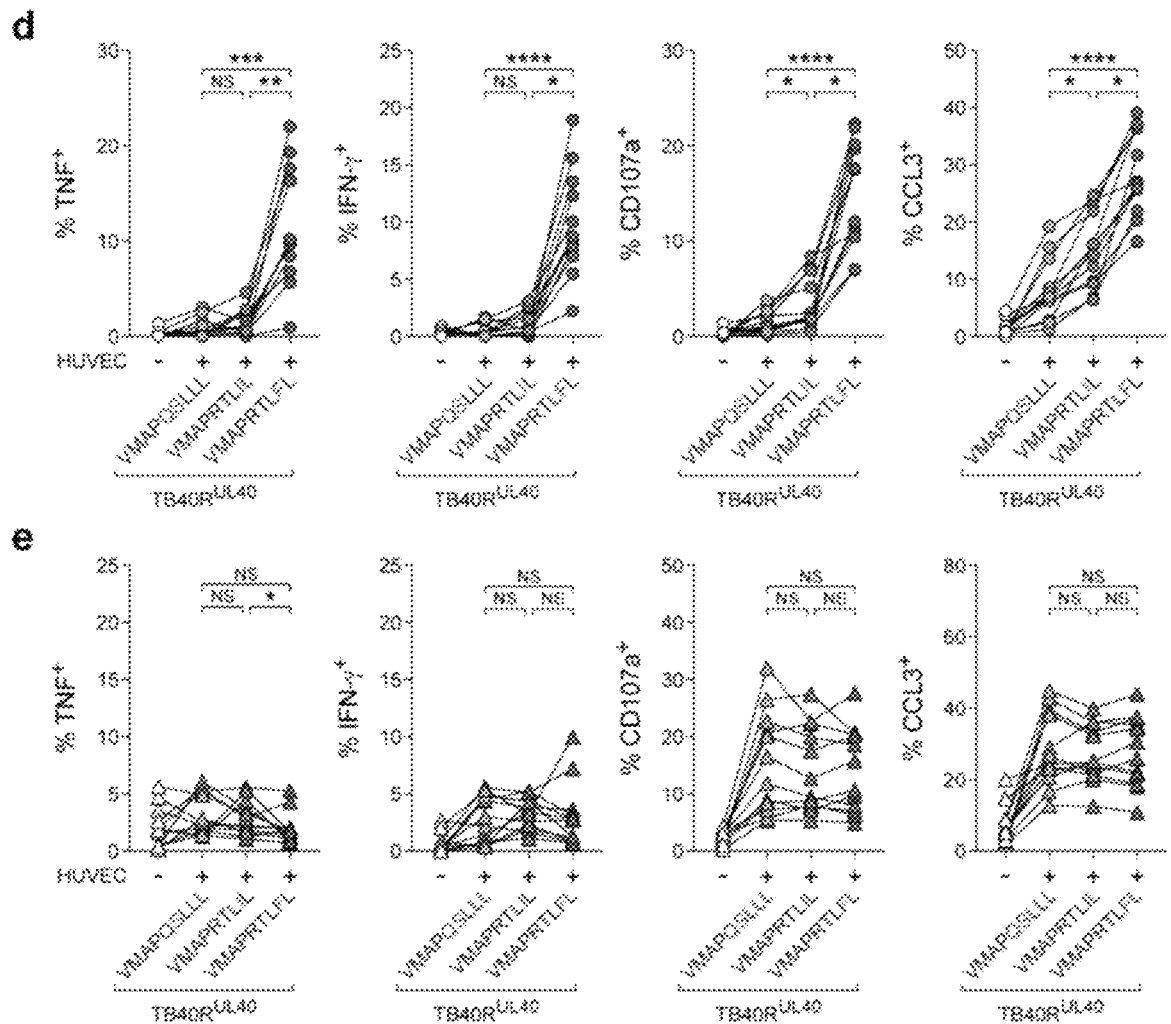

FIG. 6. NKG2C− NK Cells Do Not Differentially Recognize HCMV-Encoded Peptide Sequences During Infection. HCMV UL40 sequences: VMAPRTLFL (SEQ ID NO: 2); VMAPRTLIL (SEQ ID NO: 3); and VMAPQSLLL (SEQ ID NO: 12). (a) HUVEC were infected with TB40R and transcript levels of HCMV UL40 relative to human GAPDH were determined by qPCR at indicated time points. Symbols indicate independent experiments (n=4) and lines median. (b-c) HUVEC were infected with TB40R mutants and analyzed by flow cytometry 48 h post infection. (b) Representative FACS staining (left) of uninfected and infected (HCMV-IE+) HUVEC compared to fluorescence minus one (FMO) control and summary (right) of HLA class I expression. Symbols indicate independent experiments (n=10) and lines median. (c) Representative FACS staining (left) of uninfected and infected (HCMV-IE+) HUVEC compared to FMO control and summary (right) of HLA-E expression. Symbols indicate independent experiments (n=9) and lines median. (d) Purified rested NK cells from HCMV+ donors were cultured in medium or with virus-infected HLA-C1 homozygous HUVEC for 6 h. Summary of effector functions gated on viable CD56dim NKG2A− CD57+ KIR2DL1− KIR3DL1− KIR2DL3+ NKG2C+ adaptive NK cells. Connected symbols represent individual donors (n=12 in 3 independent experiments). (e) Purified NK cells from HCMV+ donors were primed with 25 ng/mL of IFN-α for 16 h and subsequently cultured in medium or with virus-infected HLA-C1 homozygous HUVEC for 6 h. Summary of effector functions gated on viable CD56dim KIR2DL1− KIR3DL1− KIR2DL3+ NKG2C− NK cells. Connected symbols represent individual donors (n=12 in 3 independent experiments). Friedman test with Dunn's post test. NS not significant, *p<0.05, p<0.01, *p<0.005, ****p<0.0001.

Figure 7:
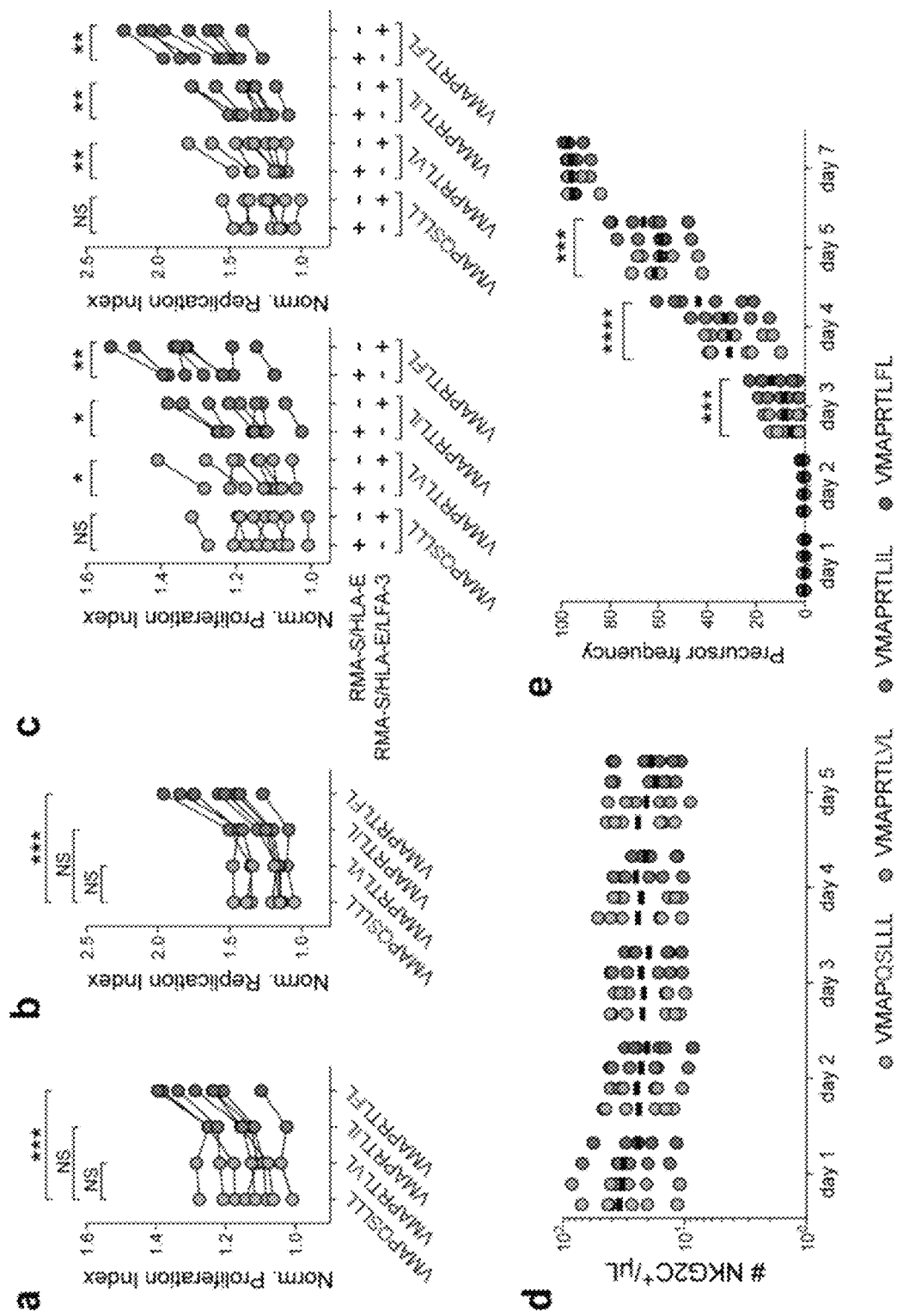
Figure 7:
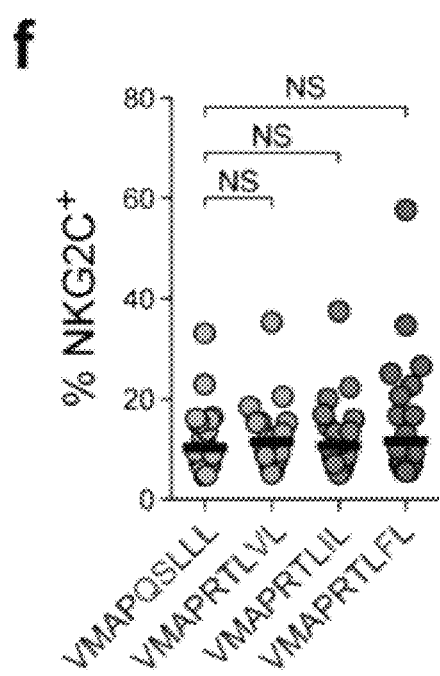

FIG. 7. Co-Stimulation via LFA-3 Enhances Proliferation of NKG2C+ NK Cells from HCMV− donors. HCMV UL40 sequences: VMAPRTLFL (SEQ ID NO: 2); VMAPRTLIL (SEQ ID NO: 3); VMAPRTLVL (SEQ ID NO: 5); and VMAPQSLLL (SEQ ID NO: 12). (a-b) Purified CD56dim NK cells from HCMV− donors were cultured for 7 days with peptide-pulsed RMA-Si/HLA-E in the presence of IL-15. (a) Proliferation indices and (b) replication indices of NKG2C+ NK cells were normalized to NKG2C− NK cells. Connected symbols represent individual donors (n=8 in 3 independent experiments). Friedman test with Dunn's post test. (c) Purified CD56dim NK cells from HCMV− donors were cultured for 7 days with either RMA-S/HLA-E or RMA-S/HLA-E/LFA-3 in the presence of IL-15. Proliferation and replication indices were normalized as in (a). Connected symbols represent individual donors (n=8 in 3 independent experiments). Two tailed Wilcoxon test. (d-f) Purified CD56dim NK cells from HCMV− donors were cultured with peptide-pulsed RMA-S/HLA-E/LFA-3 in the presence of IL-15. (d) Absolute numbers of NKG2C+ NK cells per μL. of culture medium and (e) precursor frequency of NKG2C+ NK cells over time. Symbols indicate individual donors (n=8) and lines median. Two-way repeated-measures ANOVA with Bonferroni correction. (f) Frequency of NKG2C+ NK cells after 14 days of culture. Symbols indicate individual donors (n=18) and lines median. Friedman test with Dunn's post test. NS not significant, *p<0.05, p<0.01, *p<0.005, ****p<0.0001.

Figure 8:
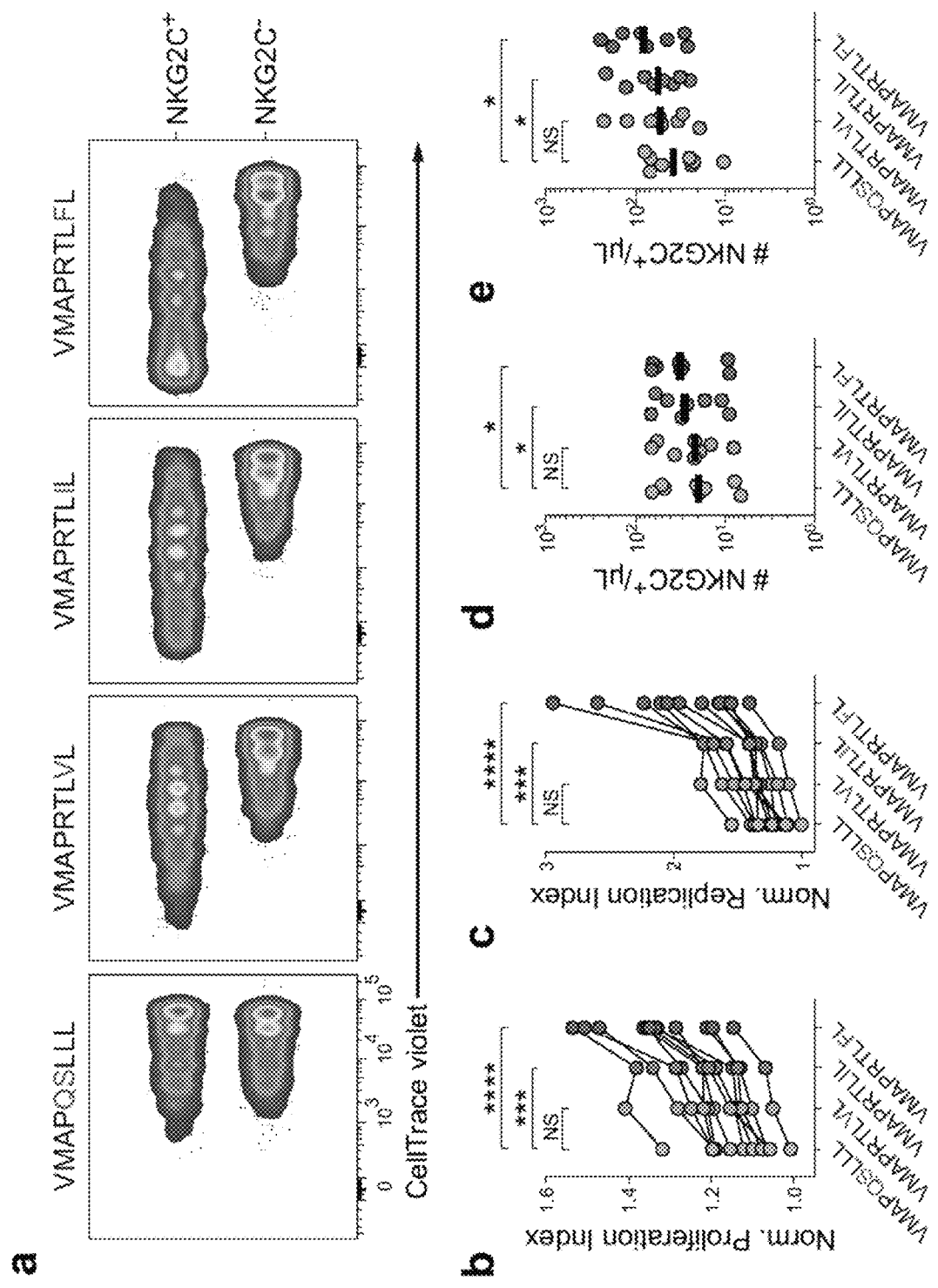

FIG. 8. Peptide Recognition Controls The Extent of NKG2C+ NK-Cell Proliferation in HCMV-Individuals. HCMV UL40 sequences: VMAPRTLFL (SEQ ID NO: 2); VMAPRTLIL (SEQ ID NO: 3); VMAPRTLVL (SEQ ID NO: 5); and VMAPQSLLL (SEQ ID NO: 12). (a-e) Purified CD56dim NK cells were cultured in the presence of IL-15 and peptide-pulsed RMA-S/HLA-E. (a) Representative CellTrace dilution of viable NKG2C+ and NKG2C− NK cells from a HCMV− donor after 7 days of culture. (b-c) CellTrace dilution patterns were analyzed using FlowJo to obtain (b) proliferation index as well as (c) replication index of NKG2C+ normalized to NKG2C− NK cells after 7 days of culture. Connected symbols represent individual donors (n=12 in 5 independent experiments). Friedman test with Dunn's post test. (d-e) Absolute NKG2C+ NK-cell numbers were determined at (d) day 7 and (e) day 14. Symbols represent individual donors (n=8 in 2 independent experiments) and lines median. Friedman test with Dunn's post test. NS not significant, *p<0.05, *p<0.001, **p<0.0001.

Figure 9:
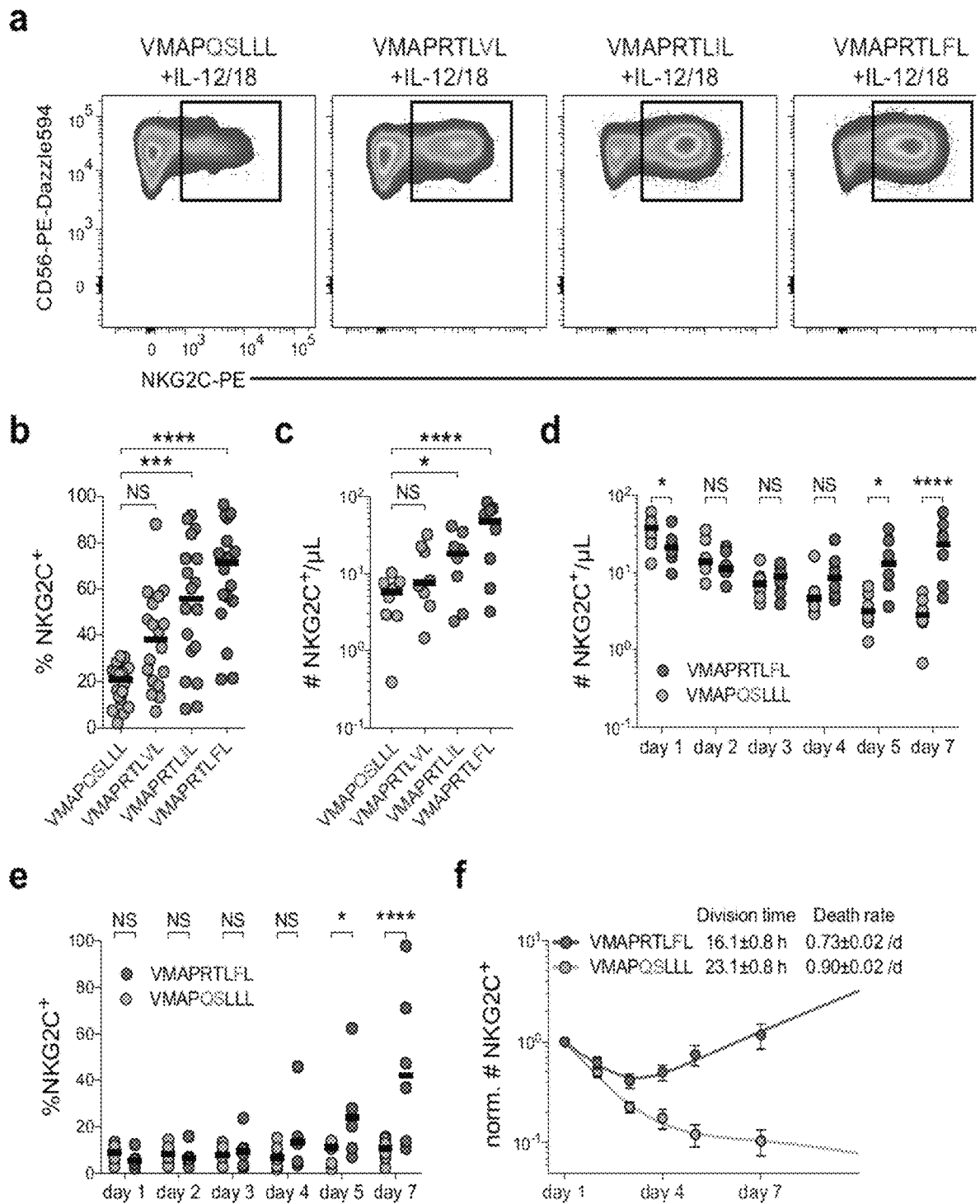

FIG. 9. Peptide Recognition Controls Accumulation of NKG2C+ NK Cells from HCMV-Individuals in the Presence of Pro-Inflammatory Signals. HCMV UL40 sequences: VMAPRTLFL (SEQ ID NO: 2); VMAPRTLIL (SEQ ID NO: 3); VMAPRTLVL (SEQ ID NO: 5); and VMAPQSLLL (SEQ ID NO: 12). (a-f) Purified CD56dim NK cells from HCMV− donors were cultured with peptide-pulsed RMA-S/HLA-E/LFA-3 in the presence of IL-15 combined with IL-12/IL-18 treatment during the initial 20 h of culture. (a) Representative FACS stainings of NKG2C on NK cells in the indicated conditions and (b) summary of the frequencies of NKG2C+ cells within viable NK cells after 14 days of culture. Symbols represent individual donors (n=18 in 7 independent experiments) and lines median. Friedman test with Dunn's post test. (c) Summary of absolute NKG2C+ NK-cell numbers determined at day 14. Symbols represent individual donors (n=8 in 2 independent experiments) and lines median. (d-e) Cultures were monitored at indicated time points for (d) absolute NKG2C+ NK-cell numbers as well as (e) frequencies of NKG2C+ NK cells. Symbols Represent individual donors (n=6 in 2 independent experiments) and lines median. Repeated two-way ANOVA with Bonferroni correction. (f) Modified Gett/Hodgkin model describing NKG2C+ NK-cell proliferation and accumulation dynamics. Symbols and error bars indicate mean±SEM of experimentally obtained absolute NKG2C+ NK-cell counts as in (d), after normalization to day 1 values (set as 1). Lines indicate best-fit curves of the model. Precursor frequencies were experimentally obtained (FIG. 10a) while division times and death rates (both mean±SEM) were inferred as best-fit parameters by non-linear optimization. NS not significant, *p<0.05, p<0.01, *p<0.001, ****p<0.0001.

Figure 10:
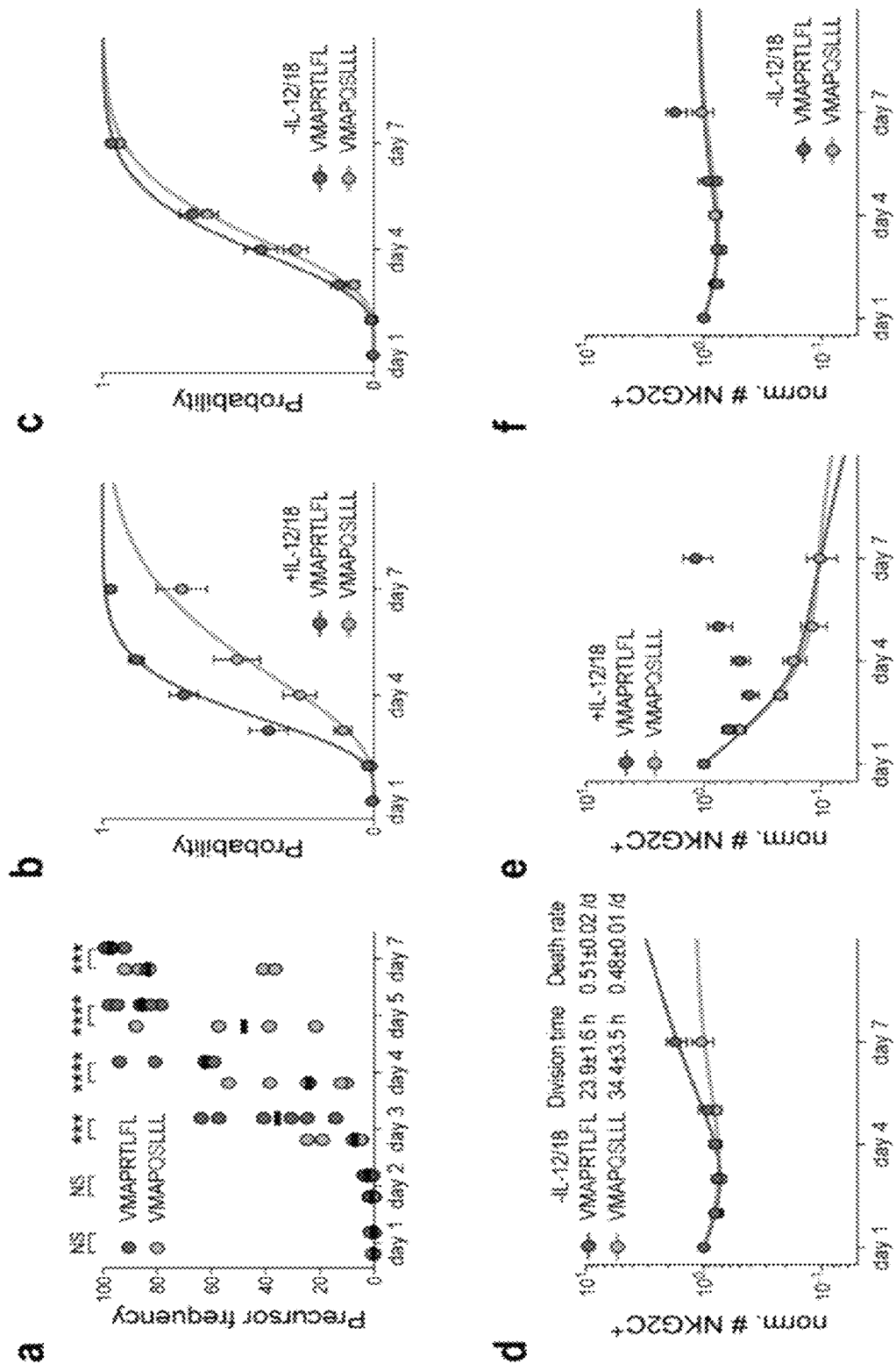

FIG. 10. Analysis of NKG2C+ NK-cell proliferation. HCMV UL40 sequences: VMAPRTLFL (SEQ ID NO: 2); and VMAPQSLLL (SEQ ID NO: 12). (a) Purified CD56dim NK cells from HCMV-donors were cultured with peptide-pulsed RMA-S/HLA-E/LFA-3 in the presence of IL-15 combined with IL-12/18 treatment during the initial 20 h of culture. Precursor frequency of NKG2C+ NK cells over time is displayed. Symbols indicate individual donors (n=6) and lines median Two-way repeated-measures ANOVA with Bonferroni correction. (b-f) Mathematical analysis of NKG2C+ NK-cell proliferation dynamics. (b-c) Symbols and error bars indicate mean±SEM of experimentally obtained precursor frequencies of NKG2C+ NK cells (b) with (data from FIG. 10a) or (c) without (data from FIG. 7e) IL-12/18 treatment during the initial 20 h of culture. Lines indicate best-fit gamma distributions, which are used as input for FIG. 9f and FIG. 10d. (d) Modified Gett/Hodgkin model describing NKG2C+ NK-cell proliferation and accumulation dynamics in the absence of IL-12/18 treatment. Symbols and error bars indicate mean±SEM of experimentally obtained absolute NKG2C+ NK-cell counts after normalization to day 1 values (set as 1); lines indicate best-fit curves of the model. Precursor frequencies were experimentally obtained (FIG. 7e, FIG. 10c), while division times and death rates (both mean±SEM) were inferred as best-fit parameters by non-linear optimization. (e-f) Modified Gett/Hodgkin models with fixed input parameters in the presence (e) or absence (f) of IL-12/18 treatment. Symbols and error bars indicate mean±SEM of experimentally obtained absolute counts after normalization to day 1 values (set as 1); lines indicate curves of the model. Precursor frequencies were experimentally obtained; division time and death rate values were inferred by non-linear optimization for the VMAPQSLLL (SEQ ID NO: 4) peptide (as in FIG. 9f and FIG. 10d, respectively) and set as fixed parameters for both peptides. NS not significant, *p<0.005, **p<0.0001.

Figure 11:
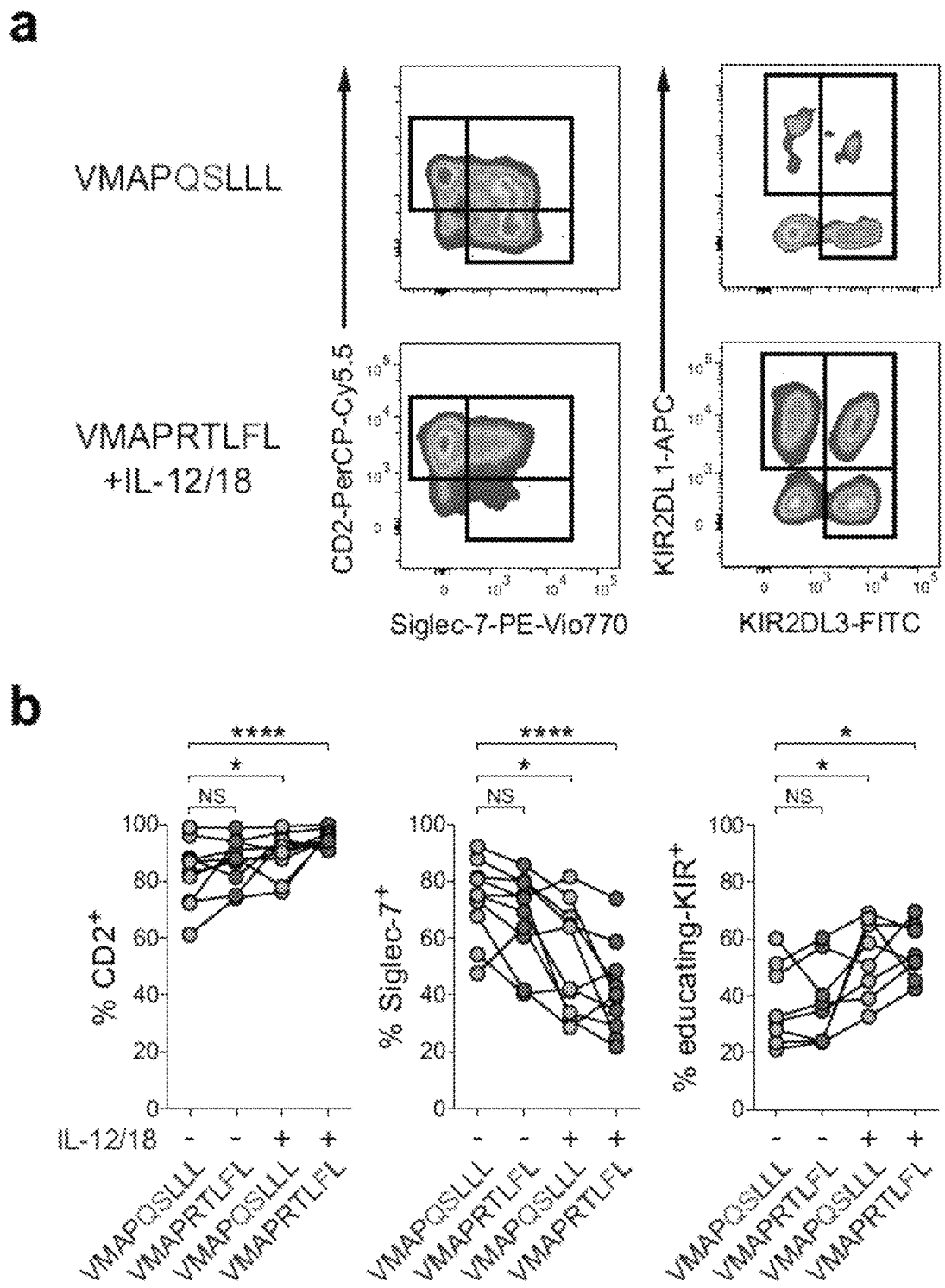
Figure 11:
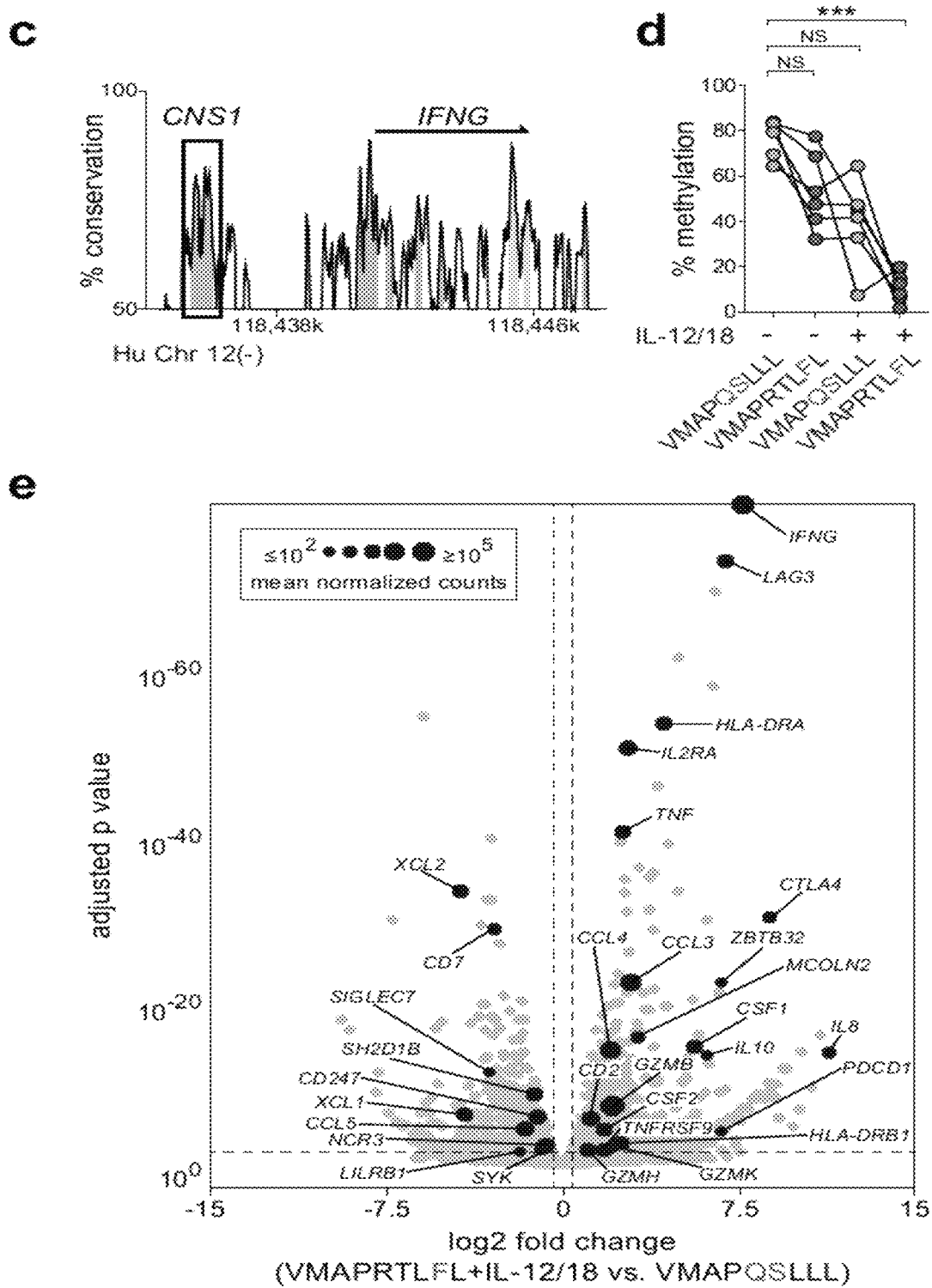

FIG. 11. FIG. 6: Peptide Recognition and Pro-Inflammatory Cytokines Co-Operate in Guiding the Differentiation of Adaptive NKG2C+ NK Cells in vitro. HCMV UL40 sequences: VMAPRTLFL (SEQ ID NO: 2); and VMAPQSLLL (SEQ ID NO: 12). (a-d) Purified CD56dim NK cells from HCMV− donors were cultured with peptide-pulsed RMA-S/HLA-E/LFA-3 in the presence of IL-15 alone or combined with IL-12/IL-18 treatment during the initial 20 h of culture. (a) Representative FACS stainings of CD2, Siglec-7, KIR2DL1, and KIR2DL3 gated on viable NKG2C+ NK cells cultured in the indicated conditions. (b) Summary of frequencies of CD2+, Siglec-7+, and educating KIR+ cells within viable NKG2C+ NK cells after 14 days of culture. Connected symbols represent individual donors (n=8 for educating KIR, n=10 for CD2 and Siglec-7 in 2-5 independent experiments). Friedman test with Dunn's post test. (c-d) After 7 days of culture in the indicated conditions, viable NKG2C+ NK cells were sorted and probed for DNA methylation levels of the IFNG conserved non-coding sequence (CNS) 1. (c) VISTA browser alignment of mouse Ifng and human IFNG indicating conserved regions with >70% sequence identity (light red) as well as UTR (light blue). Arrow indicates transcription direction of human IFNG. (d) Average percentage of methylation at 6 CpG within IFNG CNS1 were determined using NGS. Connected symbols represent individual donors (n=6 in 3 independent experiments). Friedman test with Dunn's post test. (e) Differential gene expression analysis of sorted viable CD56+ NKG2C+ NK cells cultured in the presence of VMAPQSLLL (SEQ ID NO. 4)-pulsed targets (n=3 donors) or VMAPRTLFL (SEQ ID NO. 2)+IL-12/18 (n=5 donors) for 7 days. Selected genes highlighted in black are differentially expressed with absolute fold changes >1.3 (dashed vertical lines) and adjusted p values <0.05 (dashed horizontal line). Dot sizes were adjusted to mean normalized counts. NS not significant, *p<0.05, *p<0.001, **p<0.0001.

Figure 12:
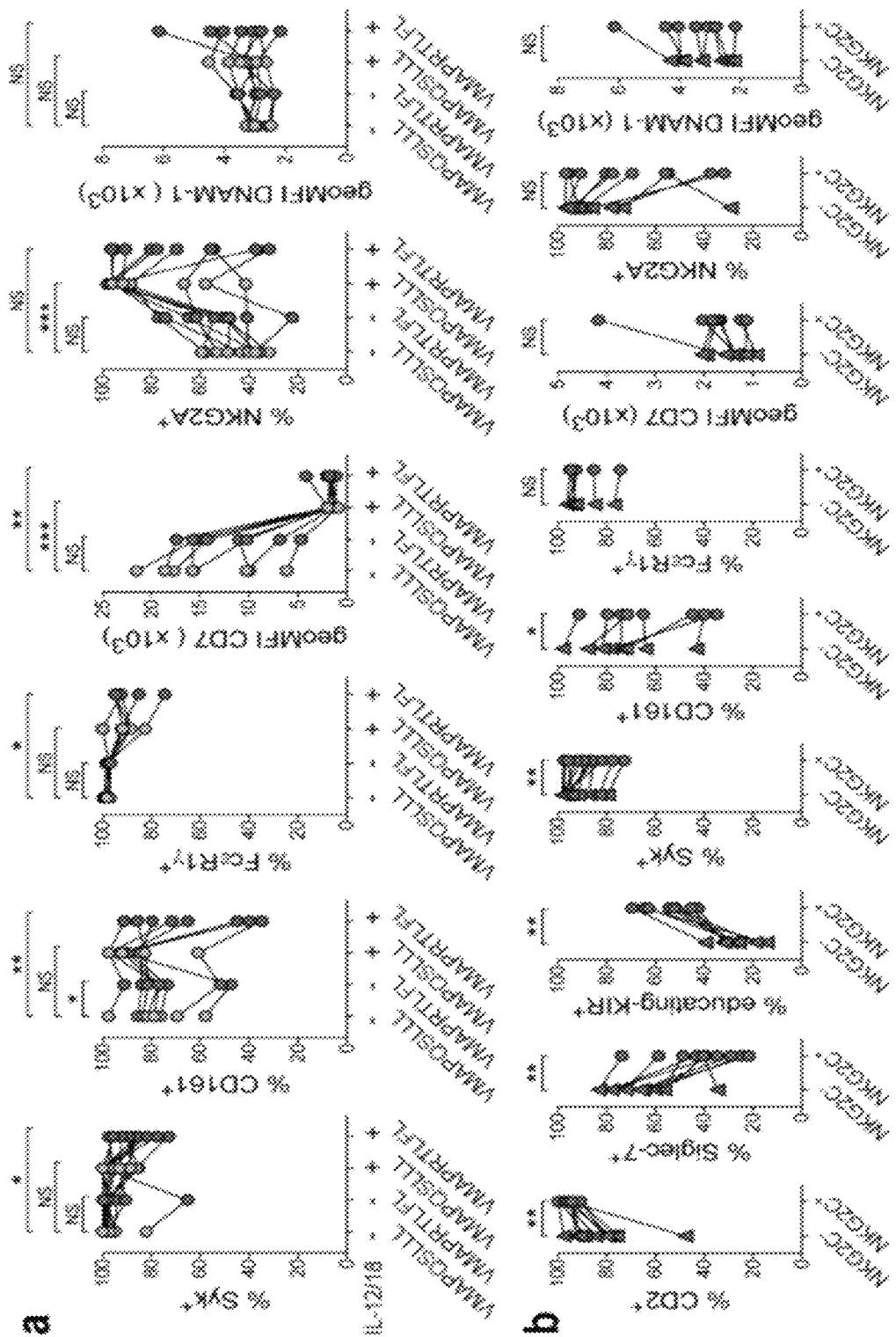
Figure 12:
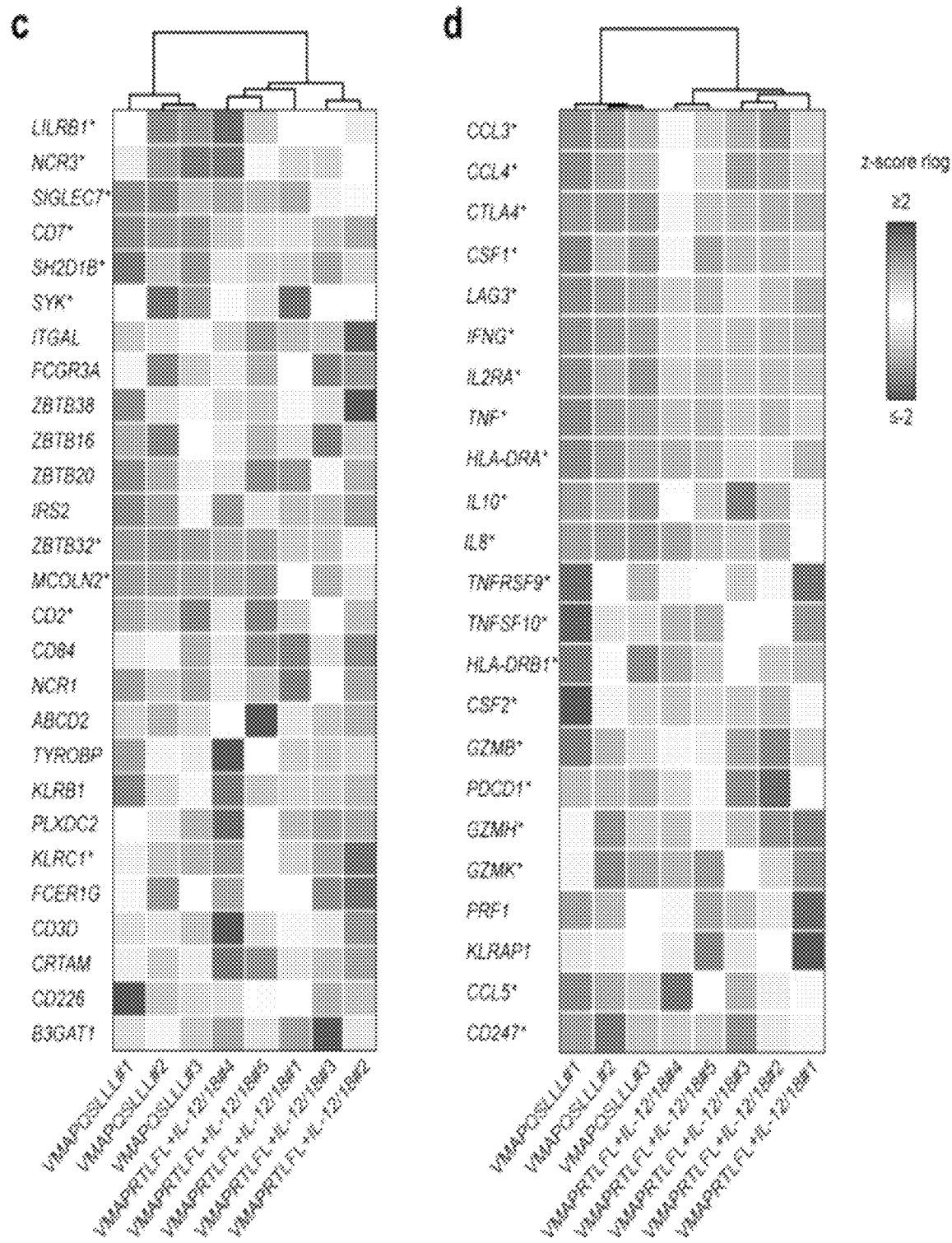

FIG. 12. Phenotypic Alterations of NKG2C+ NK Cells. HCMV UL40 sequences: VMAPRTLFL (SEQ ID NO: 2); and VMAPQSLLL (SEQ ID NO: 12). (a-b) Purified CD56dim NK cells from HCMV− donors were cultured for 14 days with peptide-pulsed RMA-S/HLA-E/LFA-3 in the presence of IL-15 alone or in combination with IL-12/18. (a) Summaries of Syk, CD161, FcεR1g, CD7, NKG2A, and DNAM-1 expression on viable NKG2C+ NK cells. Connected symbols represent individual donors (n=6 for FcεR1γ; n=8 for CD161, CD7, and DNAM-1; n=10 for NKG2A; n=12 for Syk in 2-5 independent experiments). Friedman test with Dunn's post test. (b) Comparison of NKG2C− and NKG2C+ NK cells after 14 days of culture with VMAPRTLFL (SEQ ID NO: 2)-pulsed RMA-S/HLA- E/LFA-3 in the presence of IL-15 and IL-12/18. Connected symbols represent individual donors (n=6 for FcεR1γ; n=8 for educating KIR, CD161, CD7, and DNAM-1; n=10 for CD2, Siglec-7, and NKG2A; n=12 for Syk in 2-5 independent experiments). Two-tailed Wilcoxon test. NS not significant, *p<0.05, p<0.01, *p<0.005. (c-d) Gene expression analysis of sorted viable CD56+ NKG2C+ NK cells cultured in the presence of VMAPQSLLL (SEQ ID NO. 4)-pulsed targets (n=3 donors) or VMAPRTLFL (SEQ ID NO. 2)+IL-12/18 (n=5 donors) for 7 days. Heatmaps of selected (c) adaptive NKcell signature genes and (d) activation and exhaustion markers based on zscores of rlog-transformed read counts clustered by Pearson correlation and Ward minimum variance. Asterisk-marked genes indicate adjusted p<0.05.

Figure 13:
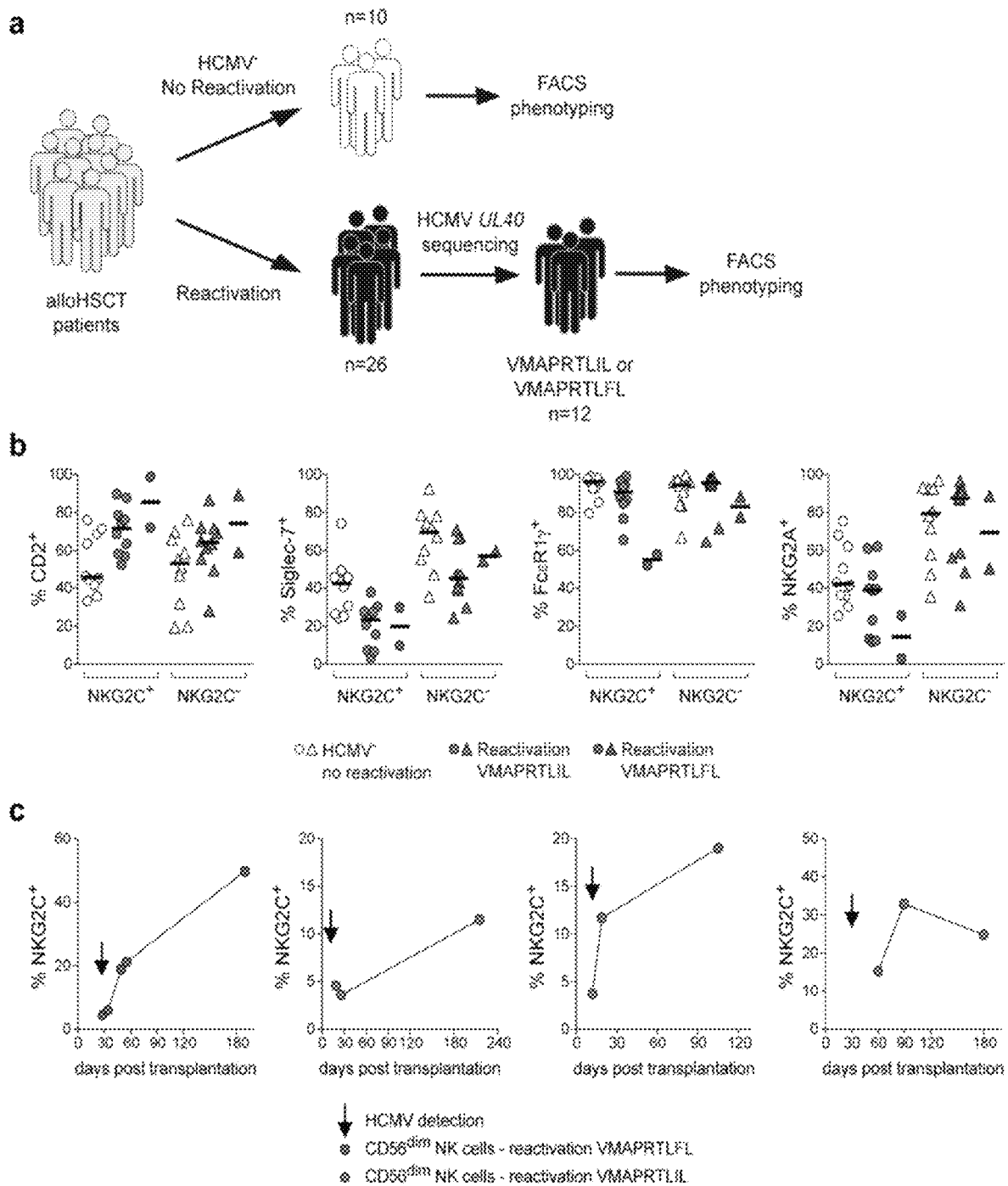

FIG. 13. Analysis of the Phenotype of Adaptive NKG2C+ NK cells Upon HCMV Infection in vivo. HCMV UL40 sequences: VMAPRTLFL (SEQ ID NO: 2); and VMAPRTLIL (SEQ ID NO: 3). (a) Study design. (b) Expression of CD2, Siglec-7, FcεR1g, and NKG2A by NKG2C+ and NKG2C− NK cells. Symbols represent individual patients (white circles, HCMV− without reactivation, n=10; blue circles, HCMV reactivation with VMAPRTLIL (SEQ ID NO. 3) peptide, n=10; red circles, HCMV reactivation with VMAPRTLFL (SEQ ID NO. 2) peptide, n=2) and lines depict median. (c) Frequency of NKG2C+ cells within the CD3− CD56dim compartment over time. Black arrow heads indicate time points of initial HCMV detection.

Figure 14:
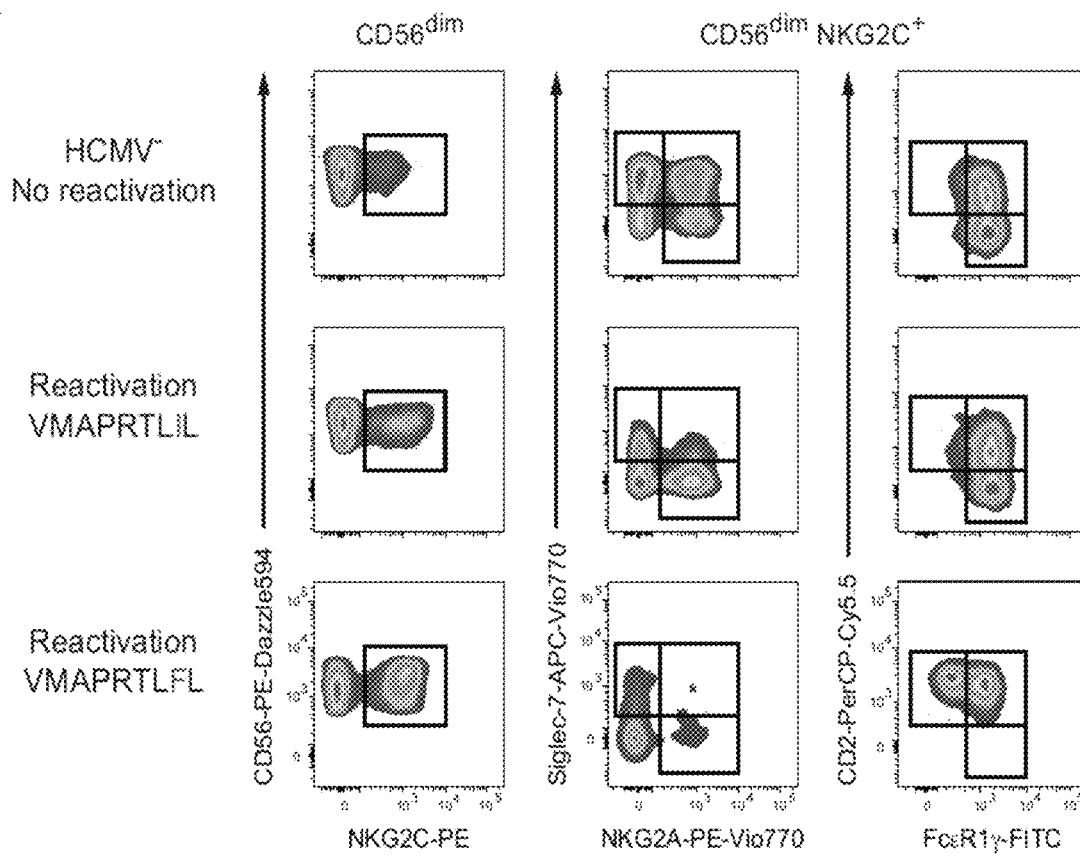
Figure 14:
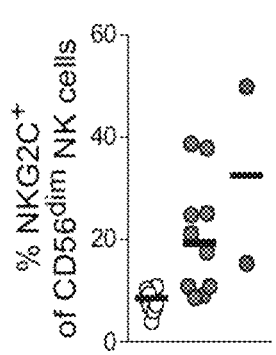
Figure 14:
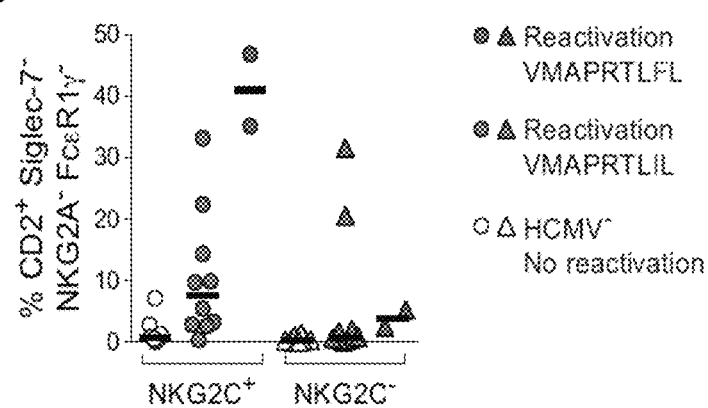
Figure 14:
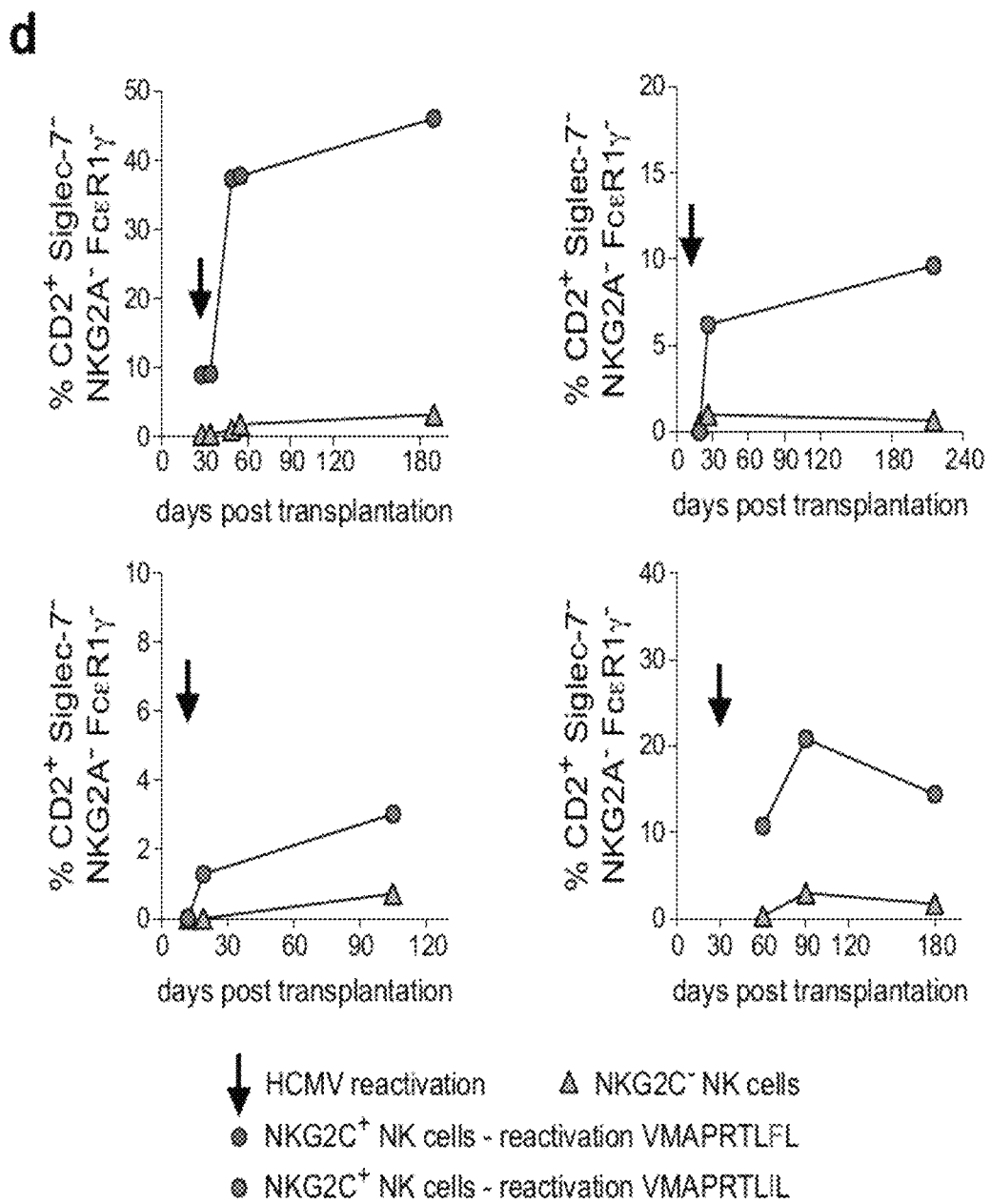

FIG. 14. Analysis of the Phenotype of Adaptive NKG2C+ NK cells Upon HCMV Infection in vivo. HCMV UL40 sequences: VMAPRTLFL (SEQ ID NO: 2); and VMAPRTLIL (SEQ ID NO: 3). (a-d) Patients undergoing alloHSCT were monitored for HCMV reactivation to sequence the HCMV UL40-encoded peptide and determine the NK-cell phenotype. (a) Representative FACS staining of (left) NKG2C gated on viable CD14− CD19− CD3− CD56dim NK cells and of (right) Siglec-7, NKG2A, CD2, and FcεR1γ gated on CD56dim NKG2C+ NK cells. (b) Summary of the frequencies of NKG2C+ cells within CD56dim NK cells as well as (c) summary of the frequencies of CD2+ Siglec-7− NKG2A− FcεR1γ− cells within NKG2C+ and NKG2C− NK cells. Symbols represent patients (white symbols, HCMV−, n=10; blue symbols, HCMV reactivation with VMAPRTLIL (SEQ ID NO. 3) peptide, n=10; red symbols, HCMV reactivation with VMAPRTLFL (SEQ ID NO. 2) peptide, n=2) and lines median. (d) Frequencies of CD2+ Siglec-7− NKG2A− FcεR1γ− cells within NKG2C+ (blue circles, HCMV reactivation with VMAPRTLIL (SEQ ID NO. 3) peptide; red circles, HCMV reactivation with VMAPRTLFL (SEQ ID NO. 2) peptide) and NKG2C−(grey triangles) NK cells were monitored over time. Black arrowheads indicate time point of initial HCMV detection.

Figure 15:
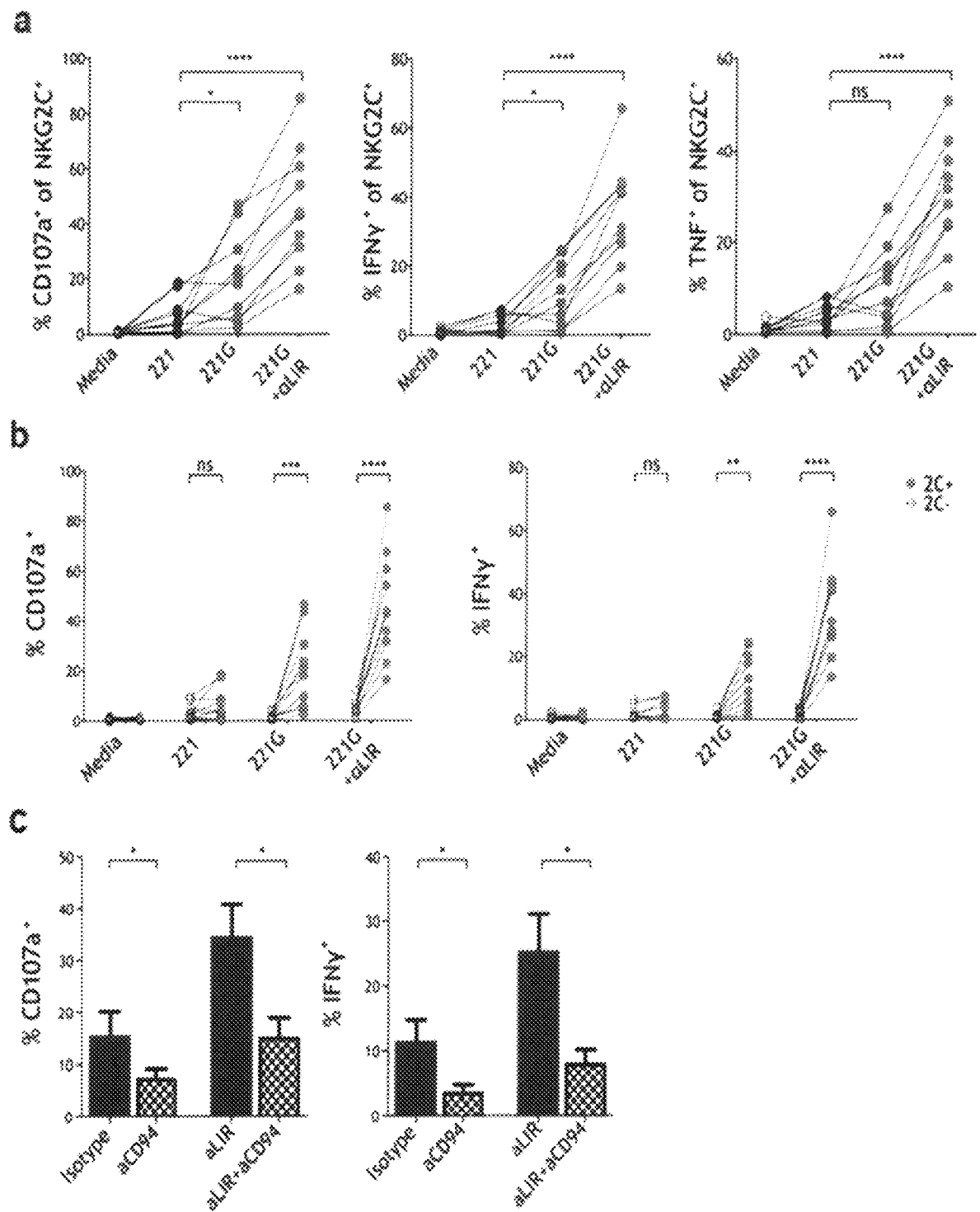

FIG. 15. NKG2C+ NK cells preferentially recognize HLA-G/HLA-E expressing tumor cells. CD56dim NK cells were co-cultured with 721.221 cells untransfected (221) or transfected with HLA-G (221G) in the presence or absence of a blocking antibody against LILRB1 (aLIR). (A) Quantification of degranulation as measured by CD107a and production of IFNγ and TNF by NKG2C+ NK cells (n=10). (B) Direct comparison of degranulation and IFNγ production NKG2C+ (2C+) and NKG2C− (2C−) NK cells, both pre-gated as LILRB1+ to account for differences in expression of this receptor between the two subsets. (C) Sorted NKG2C+ NK cells were co-cultured with 221G cells in the presence or absence of blocking antibodies against LILRB1 (aLIR) and CD94 (aCD94) and their activation analyzed in terms of degranulation and IFNg production (n=4). Multiple measures ANOVA with Bonferroni post test (A-B) or Wilcoxon test (C). NS not significant, *p<0.05, *p<0.001, **p<0.00011.

Figure 16:
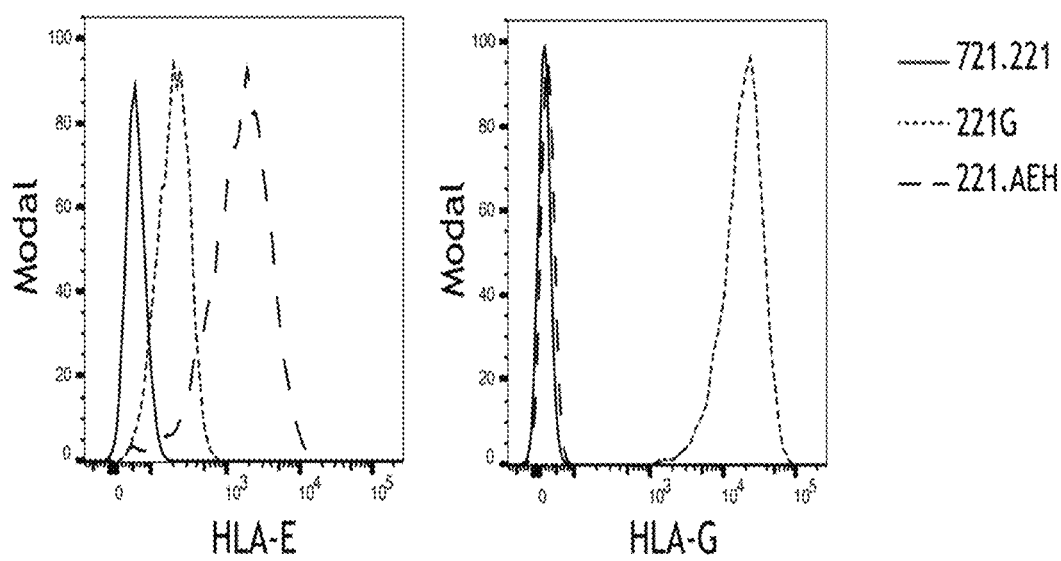

FIG. 16. NKG2C+ NK cells preferentially recognize HLA-G/HLA-E expressing tumor cells. 721.221 cells untransfected (221) or transfected with HLA-G (221G) or a fusion protein driving expression of HLA-E (221.AEH) were stained for HLA-E and HLA-G and analyzed by flow cytometry.

DETAILED DESCRIPTION OF THE INVENTION

All cited documents of the patent and non-patent literature are hereby incorporated by reference in their entirety.

The present invention relates to an isolated peptide for use as a medicament, wherein said peptide has 9 to 30 amino acids and comprises or consists of an amino acid sequence according to SEQ ID NO 1 (VMAPRTLXL), wherein X is an amino acid with a hydrophobic side chain (A, I, L, F, V, P, G), preferably V, L, I or F.

Amino acid sequences of preferred polypeptides of the present invention are listed under Table 1.

TABLE 1

Amino acid sequences of preferred peptides of the invention.

| | |
|---|---|
| SEQ ID NO 1<br>Therein, X may be an amino acid with a hydrophobic side chain (A, I, L, F, V, P, G), preferably V, L, I or F. | VMAPRTLXL |
| SEQ ID NO 2 | VMAPRTLFL |
| SEQ ID NO 3 | VMAPRTLIL |
| SEQ ID NO 4 | VMAPRTLLL |
| SEQ ID NO 5 | VMAPRTLVL |

In one embodiment the invention therefore encompasses a polypeptide as described herein comprising or consisting of an amino acid sequence selected from the group consisting of:

a) an amino acid sequence comprising or consisting of an amino acid sequence according to SEQ ID NO 1-5; wherein the polypeptide is preferably no longer than 100, 90, 80, 70, 60, 50 or 40, preferably 30, more preferably 20, most preferably no longer than 10 or 9 amino acids;

b) an amino acid sequence comprising or consisting of an amino acid sequence according to SEQ ID NO 1-5, wherein the length of the amino acid molecule is between 5 and 300 amino acids, 6 and 200 amino acids, 7 and 100, 8 and 50, preferably between 9 and 30 amino acids, wherein the surrounding sequences are preferably provided as UL-40 sequences flanking the amino acid sequences according to SEQ ID NO 1-5, or as sequences from MHC class I molecules, preferably non-classical MHC class I molecules, most preferably HLA-G, preferably flanking the signal peptide (also called leader sequence or leader peptide or signal sequence) of the respective MHC class I molecule.

c) an amino acid sequence having sufficient sequence identity to be functionally analogous/equivalent to an amino acid sequence according to a), comprising preferably a sequence identity to an amino acid sequence according to a) of at least 70%, 80%, preferably 90%, more preferably 95%; and d) an amino acid sequence of a), b) or c) which is modified by deletions, additions, substitutions, translocations, inversions and/or insertions and functionally analogous/equivalent to an amino acid sequence according to a), b) or c).

Functionally analogous sequences refer preferably to the ability to induce to induce expansion and/or activation of NKG2C+ natural killer (NK) cells.

Embodiments of the invention may comprise a polypeptide as described herein comprising or consisting of an amino acid sequence SEQ ID NO 1-5, or variants of these sequences, wherein the sequence variant may comprise a sequence identity to SEQ ID NO 1-5 of 50, 55, 60, 65, 70, 75, 80, 81, 82, 83, 84, 85, 86, 87, 88, 89, 90, 91, 92, 93, 94, 95, 96, 97, 98 or 99%. Sequence identity may be determined using methods known to one skilled in the art, such as BLAST or other sequence alignment tools.

In further preferred embodiments, the invention relates to a polypeptide comprising or consisting of an amino acid sequence derived from the UL-40 protein of HCMV. In further embodiments, the invention relates to a polypeptide comprising or consisting of an amino acid sequence derived from the signal sequence of a MHC class I molecule, preferably a non-classical MHC class I molecules, most preferably HLA-G.

Preferably, the amino acid sequence of the peptide has a length of at least 7 amino acids, more preferably 8 amino acids, most preferably 9 amino acids. Sequence homology refers to a sequence identity of more than 65%, preferably more than 70%.

Protein modifications to the polypeptides of the present invention, which may occur through substitutions in amino acid sequence, and nucleic acid sequences encoding such molecules, are also included within the scope of the invention. Substitutions as defined herein are modifications made to the amino acid sequence of the protein, whereby one or more amino acids are replaced with the same number of (different) amino acids, producing a protein which contains a different amino acid sequence than the primary protein. In some embodiments this amendment will not significantly alter the function of the protein. Like additions, substitutions may be natural or artificial. It is well known in the art that amino acid substitutions may be made without significantly altering the protein's function. This is particularly true when the modification relates to a "conservative" amino acid substitution, which is the substitution of one amino acid for another of similar properties. Such "conserved" amino acids can be natural or synthetic amino acids which because of size, charge, polarity and conformation can be substituted without significantly affecting the structure and function of the protein. Frequently, many amino acids may be substituted by conservative amino acids without deleteriously affecting the protein's function. In general, the non-polar amino acids Gly, Ala, Val, lie and Leu; the non-polar aromatic amino acids Phe, Trp and Tyr; the neutral polar amino acids Ser, Thr, Cys, Gin, Asn and Met; the positively charged amino acids Lys, Arg and His; the negatively charged amino acids Asp and Glu, represent groups of conservative amino acids. This list is not exhaustive. For example, it is well known that Ala, Gly, Ser and sometimes Cys can substitute for each other even though they belong to different groups.

In embodiments of the invention, the peptide is used as a medicament to expand and/or activate NKG2C+ natural killer (NK) cells in the treatment and/or prevention of a medical condition associated with pathogenic cells expressing HLA-E and a peptide comprising an amino acid sequence according to SEQ ID NO 1 or 2.

Natural killer cells (NK cells) are cytotoxic lymphocytes of the innate immune system. NK cells provide rapid responses to viral-infected cells, acting at around 3 days after infection, and respond to tumor formation. Typically, immune cells detect major histocompatibility complex (MHC) presented on infected cell surfaces, triggering cytokine release, causing lysis or apoptosis. NK cells are unique, however, as they have the ability to recognize stressed cells in the absence of antibodies and MHC, allowing for a much faster immune reaction. They were named "natural killers" because of the initial notion that they do not require activation to kill cells that are missing "self" markers of MHC class 1. This role is especially important because harmful cells that are missing MHC I markers cannot be detected and destroyed by other immune cells, such as T lymphocyte cells.

CD94/NKG2 is a family of C-type lectin receptors which are expressed predominantly on the surface of NK cells. These receptors stimulate or inhibit cytotoxic activity of NK cells, therefore they are divided into activating and inhibitory receptors according to their function. CD94/NKG2 recognize non-classical MHC glycoproteins class I. CD94/NKG2 family includes seven members: NKG2A, B, C, D, E, F and H. NKG2 receptors are transmembrane proteins type II which dimerize with CD94 molecule. CD94 contains a short cytoplasmic domain and it is responsible for signal transduction. Therefore NKG2 receptors form disulfide bonded heterodimers with CD94. NKG2D represent an exception, since it predominantly forms a homodimer.

NKG2A and NKG2B receptors transmit inhibitory signal. They contain two immuno-receptor tyrosine-based inhibitory motives (ITIM) in their cytoplasmic tail, which transduces the signal upon engagement of a ligand through Src family kinases, and the tyrosine phosphatase SHP-1, SHP-2 or SHIP. As a result, NK cell activation is suppressed.

NKG2C, NKG2E and NKG2H are activating receptors. Ligand binding enables interaction between receptor and the ITAM-bearing adaptor protein DAP12. Subsequent signaling through Src family kinases, the tyrosine kinases Syk and ZAP-70 can lead to release cytotolytic granules containing perforin and granzyme and production of many cytokines and chemokines. NKG2D is activating receptor as well but it couples with adaptor protein DAP10 and triggers actin reorganization (cell polarization) and degranulation upon ligand engagement. The function of NKG2F receptor is not clear.

Receptors of CD94/NKG2 family bind non-classical MHC glycoproteins class I. Non-classical MHC glycoproteins class I are structurally similar to classical MHC class I molecules, but they present mainly peptides derived from the signal peptides of MHC class I. Therefore NK cells can indirectly monitor the expression of classical MHC class I molecules through the interaction of CD94/NKG2 with HLA-E.

Non-classical MHC class I molecules comprise HLA-G, HLA-E and HLE-F. For HLA-G, 7 protein isoforms have been described. Four of these isoforms are membrane-bound (HLA-G 1-4) while 3 of them lack exons 5-7, hence and existing as secreted forms (HLA-G 5-7). Of all membrane-bound HLA-G variants, HLA-G1 represents the sole full-length version of the molecule. Conversely, HLA-G2 does not contain exon 3, HLA-G3 is missing exons 3 and 4, and HLA-G4 does not include exon 4. The soluble isoforms of HLA-G (namely, HLA-G5, HLA-G6, and HLA-G7) contain part of intron 4, harboring a stop codon. This results in the expression of truncated proteins lacking exon 5, which encodes the transmembrane domain. HLA-G5, -G6, and -G7 represent the soluble counterparts of HLA-G1, G2, and -G3, respectively. HLA-E consists of 8 exons, wherein the first encodes the leader peptide sequence, exons 2, 3 and 4 encode the MHC immunoglobulin-like a domains 1, 2, and 3, respectively, exon 5 encodes the transmembrane domain and exons 6 and 7 encode the cytoplasmic tail. Similar to HLA-G, HLA-E forms a complex with β2 microglobulin. HLA-E consists of 8 exons. Of these, the first encodes the leader peptide sequence, exons 2, 3 and 4 encode the MHC immunoglobulin-like a domains 1, 2, and 3, respectively, exon 5 encodes the transmembrane domain and exons 6 and 7 encode the cytoplasmic tail. Similar to HLA-G, HLA-E forms a complex with β2 microglobulin.

HLA-G, -E, and -F are important regulators of the immune system and the upregulation of HLA-G, -E, and -F following IFNγ stimulation suggests that non-classical MHC class I molecules may be involved in negative feedback responses to potentially harmful pro-inflammatory responses. While inflammatory responses are required to eliminate cancer cells, they also trigger strong immuno-regulatory mechanisms that limit the recognition of malignant cells by the immune system, hence favoring tumor progression. Non-classical MHC class I molecules constitute means whereby malignant cells escape immuno-surveillance. Indeed, these molecules inhibit the activity of the immune system by binding to inhibitory receptors expressed by effector cells, hence suppressing their functions or inducing their apoptotic demise (Kochan et al. Oncoimmunology. 2013 Nov. 1; 2(11): e26491; Smyth et al. Oncoimmunology. 2013 Mar. 1; 2(3): e23336).

HLA-E has a very specialized role in cell recognition by NK cells by binding a restricted subset of peptides derived from signal peptides of classical and non-classical MHC class I molecules, such as HLA-A, B, C, G. These peptides are released from the membrane of the endoplasmic reticulum (ER) by the signal peptide peptidase, trimmed by the cytosolic proteasome, transport into the ER lumen by the transporter associated with antigen processing (TAP) and subsequently bound to the groove on the HLA-E molecule. This allows HLA-E to assemble correctly and to be stabilized, leading to expression on the cell surface. NK cells recognize the complex formed by HLA-E+peptide using the heterodimeric inhibitory receptors CD94/NKG2A, B and/or C. When CD94/NKG2A or CD94/NKG2B is engaged, it produces an inhibitory effect on the cytotoxic activity of the NK cell to prevent cell lysis, whereas binding of HLA-E to CD94/NKG2C results in NK cell activation. This interaction has been shown to trigger expansion of NK cell subsets in antiviral responses.

HLA-G may play a role in immune tolerance in pregnancy, being expressed in the placenta by extravillous trophoblast cells (EVT), while the classical MHC class I genes (HLA-A and HLA-B) are not expressed. HLA-G is a ligand for NK cell inhibitory receptor KIR2DL4, and therefore expression of this HLA by the trophoblast defends it against NK cell-mediated death. Aberrant induction of HLA-G expression has been observed in various malignancies and strongly associated with tumor immune escape, metastasis and poor prognosis. HLA-G, membrane-bound or soluble, strongly binds its inhibitory receptors on immune cells (NK, T, B, monocytes/dendritic cells), inhibits the functions of these effectors, and so induces immune inhibition. HLA-G function may therefore be beneficial and protective when expressed by a fetus or a transplant, but deleterious when expressed by a tumor or cancer cells, because it also protects malignant cells from antitumor immunity. Accordingly, HLA-G can be classified as an checkpoint molecule.

The terms signal peptide, leader peptide, leader sequence and signal sequence are used interchangeably in the context of the present invention and refer to is a short peptide of up to around 30 amino acids length present at the N-terminus of the majority of newly synthesized proteins that are destined towards the secretory pathway. These proteins include those that reside either inside certain organelles (the endoplasmic reticulum, golgi or endosomes), secreted from the cell, or inserted into most cellular membranes. In particular, the terms may be used herein when referring to the signal peptides comprised by classical and non-classical MHC class I molecules.

As used herein, expansion and/or activation of NKG2C+ NK cells refers to the stimulation of NKG2C+ NK cells with an activating signal leading to the execution of effector functions, such as release of cytotoxic granules and production of pro-inflammatory cytokines and chemokines, and/or the induction of survival and/or proliferation of the cells.

The term "medical conditions associated with pathogenic cells expressing HLA-E and a peptide comprising an amino acid sequence according to SEQ ID NO 1 or 2" relates to several pathologies that share the common feature of the presence of pathological cells expressing HLA-E as well as a peptide of the present invention, wherein these cells are involved in the pathological mechanisms.

Such pathologies include, for example, the situation of active HCMV infection, which may be a new infection or a reactivation of a latent infection, wherein the UL-40 protein of HCMV is expressed in a host cell that expresses HLA-E. Furthermore, such pathologies include certain cancers, wherein the cancer cells express HLA-G. The signal sequence of HLA-G comprises an amino acid sequence corresponding to the peptide of the present invention, and the signal sequence gets processed inside the cancer as described above. Cancers expressing both, HLA-E and HLA-G, have been described in the art for melanoma, choriocarcinoma, breast cancer, endometrial cancer, ovarian cancer, cervical cancer, esophageal squamous cell carcinoma, colorectal cancer, gastric cancer, hepatocellular carcinoma, glioblastoma, lung cancer, nasopharyngeal carcinoma, pancreatic adenocarcinoma, thyroid carcinoma and renal carcinoma (Curigliano G, Criscitiello C, Gelao L, Goldhirsch A. *Molecular pathways: human leukocyte antigen G (HLA-G)*. Clin Cancer Res. 2013; 19(20):5564-71; Lin A, Yan W H. *HLA-G expression in cancers: roles in immune evasion, metastasis and target for therapy*. Mol Med. 2015; Seliger B, Schlaf G. *Structure, expression and function of HLA-G in renal cell carcinoma*. Semin Cancer Biol. 2007; 17(6):444-50), and methods and techniques for determining the expression of HLA-E and HLA-G in a pathological cell are known to the skilled person and have are described in the example below.

Medical conditions and cancers associated with pathogenic cells expressing HLA-E and a peptide comprising an amino acid sequence according to SEQ ID NO 1 or 2, that are treatable by the effector function of said NKG2C+ NK cells, and/or that are susceptible to NKG2C+ NK cell cytotoxic activity comprise, without limitation, melanoma, choriocarcinoma, breast cancer, endometrial cancer, ovarian cancer, cervical cancer, esophageal squamous cell carcinoma, colorectal cancer, gastric cancer, hepatocellular carcinoma, glioblastoma, lung cancer, nasopharyngeal carcinoma, pancreatic adenocarcinoma, thyroid carcinoma and renal carcinoma, and in particular cancer types previously described to be susceptible to immunotherapy, such as melanoma, renal cell carcinoma and hematological malignancies.

The invention is based on the surprising finding that the peptides of the present invention can induce expansion and activation of NKG2C+ NK cells in vivo an in vitro. Accordingly, the peptides can be used as a medicament in the treatment of medical condition treatable by the effector function of said NKG2C+ NK cells. The receptor complex of CD94/NKG2C is an activating receptor of NKG2C+ NK cells and accordingly, the cells are useful in the treatment of diseases that are associated with pathological cells expressing the ligand of this receptor on their surface, such as the complex of HLA-E with the bound peptide of the present invention.

In addition to cancer cells, pathogenic cells expressing HLA-E and peptides resembling SEQ ID NO 1, could plausibly represent immune effector cells exacerbating pathology during inflammatory disorders, such as but not limited to rheumatic diseases and other autoimmune conditions.

In embodiments of the present invention, the peptide is used as a medicament to inhibit reactivation of human cytomegalovirus (HCMV) infections and/or reduce viral titers in an individual infected with HCMV.

Human cytomegalovirus (HCMV) is a species of the Cytomegalovirus genus of viruses, which in turn is a member of the viral family known as Herpesviridae or herpesviruses. It is typically abbreviated as HCMV or, commonly but more ambiguously, as CMV. It is also known as human herpesvirus-5 (HHV-5). HCMV infection is typically unnoticed in healthy people, but can be life-threatening for the immune-compromised, such as HIV-infected persons, organ transplant recipients, or newborn infants. Congenital cytomegalovirus infection can lead to significant morbidity and even death. After infection, HCMV remains latent within the body throughout life and can be reactivated at any time. Eventually, it may cause mucoepidermoid carcinoma and possibly other malignancies such as prostate cancer.

UL-40 is protein of 221 amino acids of HCMV, which plays a role in viral immune evasion. Human CMV has evolved multiple strategies to interfere with immune recognition of the host. A variety of mechanisms target Ag presentation by MHC class I molecules resulting in a reduced class I cell-surface expression. This down-regulation of class I molecules can trigger NK cytotoxicity, which would have to be counteracted by the virus to establish long-term infection. The UL-40 protein of HCMV, which is encoded by the open reading frame UL-40, encodes a canonical ligand for HLA-E, and expression of UL-40 in HLA-E-positive target cells is thought to induce resistance to NK cell lysis via the CD94/NKG2A receptor. However, as disclosed herein, UL-40 can comprise the peptides of the present invention and therefore HCMV infected cells may express the complex of HLA-E and the peptide of the present invention on their surface. Accordingly, such cells can be recognized by CD94/NKG2C, which leads to activation of NKG2C+ NK cells.

Accordingly, the present invention can be used to inhibit reactivation of human cytomegalovirus (HCMV) infections and/or reduce viral titers in an individual infected with HCMV. By means of the present invention, the number of NKG2C+ NK cells in a host can be increased, either by administration of the peptide of the present invention or by administering in vitro expanded NKG2C+ NK cells of the present invention. The invention can be applied to patients that are newly infected with HCMV and suffer from an active infection to reduce the viral load and to stop or accelerated the containment of the active infection. Furthermore, the invention can be applied in the context of a reactivation of HCMV infection in a latently infected individual. Additionally, the invention can be applied to prevent clinical reactivation in individuals at risk, for example because they are latently infected or receive a transplant from a latently infected donor.

In further embodiments, the invention relates to the treatment of cancer associated with elevated expression of HLA-G compared to non-cancerous cells, preferably with elevated expression of HLA-G and HLA-E compared to non-cancerous cells. The expression of HLA-G and HLA-E can be determined by well-known techniques, such as the nucleic acid and protein detection techniques based on qPCR and flow cytometry, as described in the examples below. Accordingly, it is possible to determine the expression level of HLA-G and/or HLA-E in a sample comprising pathological cells from a patient to a corresponding sample from a healthy individual or to reference values generated from corresponding samples. Such a comparison represents a routine analysis for a person skilled in the art. By means of such a comparison, it is possible to identify cancers that are susceptible to NKG2C+ NK cell cytotoxic activity.

Medical conditions associated with pathogenic cells expressing HLA-E and a peptide comprising an amino acid sequence according to SEQ ID NO 1 or 2 can be identified by a skilled person by standard laboratory methods. For example, HLA-E expression on the pathogenic cells can by analyzed by flow cytometry using HLA-E specific antibodies. The additional presence of peptides according to SEQ ID NO1 or 2 can be determined for example by mass spectrometry or antibody mediated techniques. Furthermore, the presence of proteins that lead to the generation of these peptides, such as HLA-G or UL-40 of HCMV, can be determined by antibody based techniques such as ELISA or flow cytometry or even by RT-PCR detection expression of proteins encoding such leader peptides.

In the context of the present invention, the term "treatment of a tumor" relates to the treatment of all kinds of cancer, independent of whether the cancer is associated with the formation of a solid tumor or whether the cancer cells do not form a solid tumor, as it is the case for certain leukemias.

Cancer comprises a group of diseases that can affect any part of the body and is caused by abnormal cell growth and proliferation. These proliferating cells have the potential to invade the surrounding tissue and/or to spread to other parts of the body where they form metastasis. Worldwide, there were 14 million new cases of cancer and 8.2 million cancer related deaths in 2012 (World Cancer Report 2014). The majority of cancers is caused by environmental signals involving tobacco use, obesity and infections among others, while around 5-10% are genetic cases. Cancers can be classified into subcategories based on the cell of origin. The most common subcategories are carcinomas from epithelial cells, sarcomas from connective tissue and lymphomas and leukemias from hematopoietic cells. Cancer is associated with a high variety of local and systemic symptoms and cannot be cured in many cases. In light of the high number of new cancer patients and cancer related deaths novel treatment strategies are required. Cancer according to the present invention refers to all types of cancer or neoplasm or malignant tumors found in mammals, including leukemias, sarcomas, melanomas and carcinomas. Either solid tumors and/or liquid tumors (such as leukemia or lymphoma) may be treated. Leukemias include, but are not limited to acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

Sarcomas include, but are not limited to a chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

Melanomas include, but are not limited to include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma. Carcinomas include, but are not limited to acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma exulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticurn, carcinoma telangiectodes, transitional cell carcinoma, carcinoma tuberosum, tuberous carcinoma, verrucous carcinoma, and carcinoma villosum.

Additional cancers include, but are not limited to Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, esophageal cancer, genitourinary tract cancer, malignant hypercalcemia, cervical cancer, endometrial cancer, adrenal cortical cancer, and prostate cancer.

In some embodiments, "tumor" shall include, without limitation, a prostate tumor, a pancreatic tumor, a squamous cell carcinoma, a breast tumor, a melanoma, a basal cell carcinoma, a hepatocellular carcinoma, a choloangiocellular carcinoma, testicular cancer, a neuroblastoma, a glioma or a malignant astrocytic tumor such as glioblastma multiforme, a colorectal tumor, an endometrial carcinoma, a lung carcinoma, an ovarian tumor, a cervical tumor, an osteosarcoma, a rhabdo/leiomyosarcoma, a synovial sarcoma, an angiosarcoma, an Ewing sarcoma/PNET and a malignant lymphoma. These include primary tumors as well as metastatic tumors (both vascularized and non-vascularized).

In embodiment of the invention the peptide is administered in combination with an adjuvant. Preferably, the adjuvant enhances the production of pro-inflammatory cytokines. In embodiments, the peptide of the invention is administered in combination with the peptide is administered in combination with pro-inflammatory cytokines.

As used herein, the term "adjuvant" relates to a compound or composition that is administered in combination with the peptide of the present invention, to enhance the effectiveness of the peptide. In general, an adjuvant is an agent that is given in addition to the primary or initial therapy to maximize its effectiveness. In the context of the present invention, the adjuvant is to be understood as an immunologic adjuvant. Adjuvants in immunology are often used to modify or augment the effects of a compound that modifies the immune system, such as the peptide of the present invention or a vaccine. In embodiments, the peptide of the invention may be regarded as a peptide vaccine. An immunological adjuvant stimulates the immune system to respond more vigorously to an immunological treatment. As a consequence, the combined treatment with an adjuvant provides increased immunity to a particular disease. It is believed that adjuvants accomplish this task by mimicking specific sets of evolutionarily conserved molecules, so called PAMPs, which include liposomes, lipopolysaccharide (LPS), molecular cages for antigen, components of bacterial cell walls, and endocytosed nucleic acids such as doublestranded RNA (dsRNA), single-stranded DNA (ssDNA), and unmethylated CpG dinucleotide-containing DNA. Because immune systems have evolved to recognize these specific antigenic moieties, the presence of an adjuvant can greatly increase the innate immune response to the antigen by augmenting the activities of dendritic cells (DCs), lymphocytes, and macrophages by mimicking a natural infection. Furthermore, the use of such adjuvants that are mimicking PAMPs leads to the production of pro-inflammatory cytokines.

Immunological adjuvants for use in the context of the present invention comprise, without limitation, inorganic adjuvants, such as aluminium salts (aluminium phosphate and aluminium hydroxide), squalene, AS02, AS03, AS04, oil-based adjuvants (emulsions), MF59, QS21, cytokines, virosomes, pathogen components, such as monophosphryl lipid A, Poly(IC:C) and CpG DNA adjuvants.

As known in the art, a pro-inflammatory cytokine or an immune response-stimulating cytokine is to be understood as a cytokine that leads to or produces either directly or indirectly the induction, activation and/or enhancement of an immune response, preferably directed against an antigen, for example a tumor antigen.

Cytokines are a diverse group of non-antibody proteins that act as mediators between cells. Cytokines are currently being clinically used as biological response modifiers for the treatment of various disorders. The term cytokine is a general term used to describe a large group of proteins. Particular kinds of cytokines may include Monokines, namely cytokines produced by mononuclear phagocytic cells, Lymphokines, namely cytokines produced by activated lymphocytes, especially Th cells, Interleukins, namely cytokines that act as mediators between leukocytes and Chemokines, namely small cytokines primarily responsible for leucocyte migration. Cytokine signaling is flexible and can induce both protective and damaging responses. They can produce cascades, or enhance or suppress production of other cytokines. Despite the various roles of cytokines, a skilled person is aware of which cytokines may be considered as immune response stimulating and therefore applied in the treatment of a tumor disease as described herein. Cytokines have the ability to modulate immune responses and are often utilized by a tumor to allow it to grow and manipulate the immune response. These immune-modulating effects allow them to be used as drugs to provoke an immune response against the tumor. Chemokines refer to a sub-group of cytokines (signaling proteins) secreted by cells. Chemokines have the ability to induce directed chemotaxis in nearby responsive cells; they are chemotactic cytokines. Immune-response stimulatory or immune response-modulatory cytokines and chemokines comprise, without limitation, type 1 interferons (IFN alpha and IFN beta), type 2 (IFN gamma), type III interferons (IFN lambda), IFN gamma, TNF-alpha, IL-1, IL-2, IL-12, IL-18, IL-23, IL-15 and IL-21, CXCL-8, CCL2, CCL3, CCL4, CCL5, CCL11 and CXCL10, CXCL1, CXCL2, CCL2, CCL1, CCL22, CCL17, CXCL13, CX3CL1, SDF-1, CXCL12, CCL23, MIP-3, MPIF-1, CCL19, MIP-3-beta and MIP-1β.

The terms "stimulation" and "activation" of the "immune system" or of an "immune response" may be used interchangeably.

In preferred embodiments of the invention, the peptide is administered in combination with a check point inhibitor, preferably an inhibitor of a receptor selected from the group comprising LILRB1, inhibitory KIRs, NKG2A, PD-1, CTLA-4, TIM-3, TIGIT and LAG-3.

Immune checkpoint molecules are molecules in the immune system that either turn up a signal (co-stimulatory molecules) or turn down a signal provided to immune effector cells. Thus, immune checkpoint molecules can be subdivided into co-stimulatory checkpoint molecules or co-inhibitory checkpoint molecules. Co-stimulatory checkpoint molecules include co-stimulatory lymphocyte receptors, which are lymphocyte surface-receptors that can lead to an activation or stimulation of lymphocyte effector functions. Co-inhibitory checkpoint molecules include co-inhibitory lymphocyte receptors, which are lymphocyte surface-receptors that can lead to an inhibition of lymphocyte effector functions.

An inhibitor of a receptor prevents the generation of a signal by the respective receptor. Accordingly, an inhibitor of a co-inhibitory lymphocyte receptor is a molecule that prevents the activation of the respective receptor and thereby prevents the generation of an inhibitory signal. Conversely, an activator of a receptor induces the generation of a signal by the respective receptor and an activator of a co-stimulatory lymphocyte receptor leads to the generation of a stimulatory signal. Checkpoint modulators are molecules that interfere with the activity of immune checkpoint molecules, either by stimulating or inhibiting the activity of immune checkpoint molecules.

Lymphocyte-stimulating checkpoint modulators are molecules that lead to an activation of lymphocytes, preferably effector T cells, either through activation of a co-stimulatory checkpoint molecule, or through inhibition of a co-inhibitory checkpoint molecules. Checkpoint modulators can be naturally occurring molecules or engineered molecules with the respective function interfering with or modulating the activity of an immune checkpoint molecule. Checkpoint modulators include, for example, antibodies or antibody-fragments activity directed against immune checkpoint molecule with agonistic or antagonistic, and ligands or modified ligands of immune checkpoint molecules.

Co-inhibitory checkpoint molecules comprise, without limitation, LILRB1, A2AR, B7-H3, B7-H4, BTLA, CTLA-4, IDO, KIR, LAG3, PD-1, TIM-3, TIGIT and VISTA.

Leukocyte immunoglobulin-like receptor subfamily B member 1 (LILRB1) is a protein that in humans is encoded by the LILRB1 gene. The protein belongs to the subfamily B class of LIR receptors which contain two or four extracellular immunoglobulin domains, a transmembrane domain, and two to four cytoplasmic immunoreceptor tyrosine-based inhibitory motifs (ITIMs). The receptor is expressed on immune cells where it binds to MHC class I molecules on antigen-presenting cells and transduces a negative signal that inhibits stimulation of an immune response. It is involved in the control of inflammatory responses and cytotoxicity to help focus the immune response and limit autoreactivity.

A2AR (Adenosine A2A receptor) is regarded as an important checkpoint in cancer therapy because adenosine in the immune microenvironment, leading to the activation of the A2a receptor, is negative immune feedback loop and the tumor microenvironment has relatively high concentrations of adenosine.

B7-H3, also called CD276, was originally understood to be a co-stimulatory molecule but is now regarded as co-inhibitory. MacroGenics is working on MGA271 (Enoblituzumab), which is an Fc-optimized monoclonal antibody that targets B7-H3.

B7-H4 (or VTCN1) is expressed by tumor cells and tumor-associated macrophages and plays a role in tumor evasion.

BTLA (B and T Lymphocyte Attenuator, also called CD272) is a co-inhibitory receptor, which has HVEM (Herpesvirus Entry Mediator) as its ligand. Surface expression of BTLA is gradually downregulated during differentiation of human CD8+ T cells from the naive to effector cell phenotype, however tumor-specific human CD8+ T cells express high levels of BTLA. CTLA-4 (Cytotoxic T-Lymphocyte-Associated protein 4, also called CD152) is expressed on Treg cells and serves to control T cell proliferation. CTLA-4 (CD152) is a protein receptor functioning as an immune checkpoint and is expressed by activated T cells and transmits an inhibitory signal to T cells. CTLA4 is homologous to the T-cell co-stimulatory protein CD28, and both molecules bind to CD80 and CD86 (B7-1 and B7-2 respectively), on antigen-presenting cells. CTLA-4 has a greater affinity and avidity to CD80 and CD86 with than CD28. CTLA4 transmits an inhibitory signal to T cells. Antagonistic antibodies directed against CTLA4 include ipilimumab and tremelimumab.

IDO (Indoleamine 2,3-dioxygenase) is a tryptophan catabolic enzyme with immune-inhibitory properties. Another important molecule is TDO, tryptophan 2,3-dioxygenase. IDO is known to suppress T and NK cells, generate and activate Tregs and myeloid-derived suppressor cells, and promote tumor angiogenesis.

KIR (Killer-cell Immunoglobulin-like Receptor) is a receptor for MHC Class I molecules on Natural Killer cells. Lirilumab is a monoclonal antibody to KIR.

LAG-3 (Lymphocyte Activation Gene-3) works to suppress an immune response by action to Tregs as well as direct effects on CD8+ T cells.

PD-1 (Programmed Death 1, or CD279) is a cell surface receptor that plays an important role in down-regulating the immune system and promoting self-tolerance by suppressing T cell inflammatory activity. PD-1 has two ligands, PD-L1 and PD-L2. An advantage of targeting PD-1 is that it can restore immune function in the tumor microenvironment. PD-L1, the ligand for PD1, is highly expressed in several cancers and can lead to the inhibition of anti-cancer immune response by T cells. A number of cancer immunotherapy agents that target the PD-1 receptor have been developed, including the antagonistic antibodies nivolumab, (Opdivo—Bristol Myers Squibb), Pembrolizumab (Keytruda, MK-3475, Merck), Pidilizumab (CT-011, Cure Tech) and BMS-936559 (Bristol Myers Squibb). Both Atezolizumab (MPDL3280A, Roche) and Avelumab (Merck KGaA, Darmstadt, Germany & Pfizer) are monoclonal antibodies directed against PD-L1, the ligand of PD-1.

TIM-3 (T-cell Immunoglobulin domain and Mucin domain 3) expresses on activated human CD4+ T cells and regulates Th1 and Th17 cytokines. TIM-3 acts as a negative regulator of Th1/Th17 function by triggering cell death upon interaction with its ligand, galectin-9.

VISTA (V-domain Ig suppressor of T cell activation) is a protein that is primarily expressed on hematopoietic cells so that consistent expression of VISTA on leukocytes within tumors may allow VISTA blockade to be effective across a broad range of solid tumors.

TIGIT (T cell immunoreceptor with Ig and ITIM domains, also called WUCAM and Vstm3) is an immune receptor present on some T cells and Natural Killer Cells and regulates T cell mediated immunity. TIGIT could bind to CD155 on DCs and macrophages with high affinity and to CD112 with lower affinity.

Co-stimulatory checkpoint molecules comprise, without limitation, HVEM, CD27, CD40, OX40, GITR, CD137, CD28 and ICOS.

In preferred embodiments of the invention, the peptide is administered in combination with an anti-cancer or an anti-viral therapy.

Anti-cancer therapies of the present invention comprise, without limitation, surgery, chemotherapy, radiotherapy, irradiation therapy, hormonal therapy, targeted therapy, immunotherapy, cell therapy and immune cell therapy.

In the context of the present invention, chemotherapy refers to a category of cancer treatment that uses one or more anti-cancer drugs (chemotherapeutic agents) as part of a chemotherapy regimen. Irradiation or radiation therapy or radiotherapy in the context of the present invention relates to a therapeutic approach using ionizing or ultraviolet-visible (UVNis) radiation, generally as part of cancer treatment to control or kill malignant cells such as cancer cells or tumor cells. As used herein, "immunotherapy" comprises any kind of therapeutic approach or treatment directed against a tumor employing means of the immune system to negate or destroy tumor material. This includes, without limitation, immune checkpoint modulators, immune cell therapy, adoptive transfer of immune cells or other cells that modulate the immune response, modulation of the immune cells by small molecules or biopharmaceuticals such as monoclonal antibodies, cytokines, chemokines, and cancer treatment vaccines. Immunotherapies of the present invention further comprise administration of an antibody that binds specifically to a tumor-associated antigen, the administration of a cytokine or chemokine, the administration of a small molecule with anti-tumor immune-stimulating properties, the administration of tumor antigens and/or the administration of patient-derived tumor material.

In embodiments of the invention, the peptide for use as a medicament is administered by a vector comprising or encoding the peptide of the present invention. Therefore, the present invention encompasses gene therapy comprising the administration of a therapeutic gene encoding the polypeptide described herein.

The term gene therapy preferably refers to the transfer of DNA into a subject in order to treat a disease. The person skilled in the art knows strategies to perform gene therapy using gene therapy vectors. Such gene therapy vectors are optimized to deliver foreign DNA into the host cells of the subject. In a preferred embodiment the gene therapy vectors may be a viral vector. Viruses have naturally developed strategies to incorporate DNA in to the genome of host cells and may therefore be advantageously used. Preferred viral gene therapy vectors may include but are not limited to retroviral vectors such as moloney murine leukemia virus (MMLV), adenoviral vectors, lentiviral, adenovirus-associated viral (AAV) vectors, pox virus vectors, vaccinia virus, herpes simplex virus vectors or human immunodeficiency virus vectors (HIV-1). Furthermore, the vector of the present invention may be an attenuated HCMV virus or vector, which has been genetically modified to be less harmful to the infected host than the unmodified wild-type version of the virus. The viral vectors of the invention are preferably genetically modified.

However also non-viral vectors may be preferably used for the gene therapy such as plasmid DNA expression vectors driven by eukaryotic promoters or liposomes encapsulating the transfer DNA. Furthermore preferred gene therapy vectors may also refer to methods to transfer of the DNA such as electroporation or direct injection of nucleic acids into the subject. Moreover it may be preferred that the gene therapy vectors for example a viral gene therapy vector is adapted to target suitable cells of the body, such as for example bone marrow cells, hematopoietic cells, or immune cells or progenitor cells of immune cells, preferably NK cells, NK cell progenitors or NK cell subsets, such as NKG2C+ NK cells. To this end the viral capsid may be conjugated with ligands binding to the specific target cells, such as bone marrow cells, such as hematopoietic cells, or immune cells or progenitor cells of immune cells, preferably NK cells, NK cell progenitors or NK cell subsets, such as NKG2C+ NK cells, such as monoclonal antibodies. It may also be preferred that the viral gene therapy vectors are genetically modified using inducible promoters or promoters that are specific for the target cells of interest, such as bone marrow cells, such as hematopoietic cells, or immune cells or progenitor cells of immune cells, preferably NK cells, NK cell progenitors or NK cell subsets, such as NKG2C+ NK cells, to enhance the expression of the nucleic acid specifically in the target cells. Preferred gene therapy vectors may therefore comprise vectors for an inducible or conditional expression of the polypeptides. The person skilled in the art knows how to choose preferred gene therapy vectors according the need of application as well as the methods on how to implement the nucleic acid into the gene therapy vector. (P. Seth et al., 2005, N. Koostra et, al. 2009, W. Walther et al. 2000, Waehler et al. 2007).

The present invention may relate to a nucleic acid molecule encoding a peptide of the invention. The nucleic acid according to the invention and preferred embodiments thereof, in particular a nucleic acid encoding a polypeptide of the present invention, is particularly efficient for gene therapy due to a high therapeutic potential at a small size. This ensures a stable integration at high expression levels over extended periods of times.

In a further preferred embodiment the invention relates to a cell for use as a medicament to expand and/or activate NKG2C+ natural killer (NK) cells in the treatment and/or prevention of a medical condition treatable by the effector function of said NKG2C+ NK cells. Therein the cell may be a NKG2C+ NK cell generated by the method of the present invention for cultivating and/or expanding NKG2C+ natural killer (NK) cells, or a cell, which is genetically modified and comprises an exogenous nucleic acid region encoding for a polypeptide according to the invention or preferred embodiments thereof and wherein the exogenous nucleic acid region is operably linked to a promoter.

The person skilled in the art knows how to genetically modify cells in order to express the polypeptides according to the inventions. Advantageously by expressing the therapeutically effective polypeptides the cells may act as bio pump or drug factory that continuously expresses and provides the polypeptides to the subject. Thereby the amount of the polypeptides can be held at a therapeutic level over long periods. The person skilled in the art knows which cells may be preferably used to this end. In a preferred embodiment the cells are stem cells, characterized by a stable expression of the polypeptides. Stem cells may include but are not limited to, embryonic stem cells such as early embryonic stem cells and blastocyst embryonic stem cells; fetal stem cells; umbilical cord stem cells; and adult stem cells such as mesenchymal stem cells, hematopoietic stem cells, endothelial stem cells, peripheral blood stem cells, and multipotent somatic stem cells.

The cells may migrate to the site of NK cells, NK progenitor cells or NKG2C+ NK cells in order to locally express the polypeptides in vicinity of the cells to be activated and/or expanded. Advantageously the cells may however also be transplanted at a different location as the polypeptides can also be transported by the vascular system throughout the body of the subject. Local administration of the cells e.g. by a subcutaneous injection may therefore contribute in a systemic manner largely irrespective of the location of the cells within the body of the subject. In a further preferred embodiment the peptides for use as a medicament as described herein are characterized by introducing a therapeutically effective number of said peptide either directly or comprised by a suitable vector as described herein, such as a viral vector or a cell carrying a nucleic acid encoding the peptide of the invention, to a subject within a biocompatible matrix. Preferred materials for the biocompatible matrix are agarose, carrageenan, alginate, chitosan, gellan gum, hyaluronic acid, collagen, cellulose and its derivatives, gelatin, elastin, epoxy resin, photo cross-linkable resins, polyacrylamide, polyester, polystyrene and polyurethane or polyethylene glycol (PEG). It is further preferred that the biocompatible matrix is a semi-permeable hydrogel matrix and the peptides or vectors carrying the peptide and/or a nucleic acid encoding the peptide are entrapped by said matrix. Advantageously the biocompatible matrix allows for an efficient diffusion of nutrients, oxygens and other biomolecules to ensure a long lasting persistence of the peptides or vectors carrying the peptide and/or a nucleic acid encoding the peptide, while immobilizing the peptides or vectors carrying the peptide and/or a nucleic acid encoding the peptide. Thereby the cells can be concentrated at preferred locations within the subject. For instance the peptides or vectors carrying the peptide and/or a nucleic acid encoding the peptide cells can be transplanted subcutaneously and/or in proximity of diseased regions of the subject.

In a preferred embodiment the invention further relate to pharmaceutical composition for use as a medicament, preferably to expand and/or activate NKG2C+ natural killer (NK) cells in the treatment and/or prevention of a medical condition associated with pathogenic cells expressing HLA-E and a peptide comprising an amino acid sequence according to SEQ ID NO 1 or 2 as described herein, wherein the pharmaceutical composition comprises the polypeptide, the nucleic acid, the gene therapy vector and/or the cell, and optionally a pharmaceutically accepted carrier. Preferably the pharmaceutical composition is administered to the subject at a therapeutically effective amount at any administration route as described herein. In the context of the present invention, a cell comprising or encoding a peptide of the present invention may be considered a vector.

In a preferred embodiment the pharmaceutical composition for use as a medicament as described herein is administered by introducing a therapeutically effective amount of the composition into the blood stream of a subject. In a further preferred embodiment the pharmaceutical composition for use as a medicament as described herein is administered locally, for example by administration to a site of the subject's body in proximity to a site where pathogenic cells expressing HLA-E and a peptide comprising an amino acid sequence according to SEQ ID NO 1 or 2 are localized. As used herein, in "proximity with" a tissue/site includes, for example, within 50 mm, 20 mm, 10 mm, 5 mm, within 1 mm of the tissue, within 0.5 mm of the tissue and within 0.25 mm of the tissue/site.

As used herein, "nucleic acid" shall mean any nucleic acid molecule, including, without limitation, DNA, RNA and hybrids or modified variants thereof. An "exogenous nucleic acid" or "exogenous genetic element" relates to any nucleic acid introduced into the cell, which is not a component of the cells "original" or "natural" genome. Exogenous nucleic acids may be integrated or non-integrated, or relate to stably transfected nucleic acids.

As used herein, "polypeptide" shall mean both peptides and proteins. In this invention, the polypeptides may be naturally occurring or recombinant (i.e., produced via recombinant DNA technology), and may contain mutations (e.g., point, insertion and deletion mutations) as well as other covalent modifications (e.g., glycosylation and labelling (via biotin, streptavidin, fluorescein, and radioisotopes)) or other molecular bonds to additional components. For example, PEGylate proteins are encompassed by the scope of the present invention. PEGylation has been widely used as a post-production modification methodology for improving biomedical efficacy and physicochemical properties of therapeutic proteins. Applicability and safety of this technology have been proven by use of various PEGylated pharmaceuticals for many years (refer Jevsevar et al, Biotechnol J. 2010 January; 5(1):113-28). In some embodiments the polypeptides described herein are modified to exhibit longer in vivo half-lives and resist degradation when compared to unmodified polypeptides. Such modifications are known to a skilled person, such as cyclized polypeptides, polypeptides fused to Vitamin B12, stapled peptides, protein lipidization and the substitution of natural L-amino acids with D-amino acids (refer Bruno et al, Ther Deliv. 2013 November; 4(11): 1443-1467).

In some embodiments of the invention the peptide, preferably according to sequences disclosed herein, may comprise a 0 to 10 amino acid addition or deletion at the N and/or C terminus of a sequence.

As used herein the term "a 0 to 10 amino acid addition or deletion at the N and/or C terminus of a sequence" means that the polypeptide may have a) 0, 1, 2, 3, 4, 5, 6, 7, 8, 9 or 10 additional amino acids at its N terminus and 0, 1, 2, 3, 4, 5, 6, 7, 8, 9 or 10 amino acids deleted at its C terminus or b) 0, 1, 2, 3, 4, 5, 6, 7, 8, 9 or 10 additional amino acids at its C terminus and 0, 1, 2, 3, 4, 5, 6, 7, 8, 9 or 10 nucleotides deleted at its N terminus, c) 0, 1, 2, 3, 4, 5, 6, 7, 8, 9 or 10 additional amino acids at its N terminus and 0, 1, 2, 3, 4, 5, 6, 7, 8, 9 or 10 additional amino acids at its N terminus or d) 0, 1, 2, 3, 4, 5, 6, 7, 8, 9 or 10 amino acids deleted at its N terminus and 0, 1, 2, 3, 4, 5, 6, 7, 8, 9 or 10 amino acids deleted at its C terminus.

Furthermore, in addition to the polypeptides described herein, peptidomimetics are also contemplated. Peptide analogs are commonly used in the pharmaceutical industry as non-peptide drugs with properties analogous to those of the template peptide. These types of non-peptide compound are termed "peptide mimetics" or "peptidomimetics" (Fauchere (1986) Adv. Drug Res. 15: 29; Veber and Freidinger (1985) TINS p. 392; and Evans et al. (1987) J. Med. Chem. 30: 1229) and are usually developed with the aid of computerized molecular modelling. Peptide mimetics that are structurally similar to therapeutically useful peptides may be used to produce an equivalent therapeutic or prophylactic effect. It may be preferred in some embodiments to use peptide mimetics in order to prolong the stability of the polypeptides, when administered to a subject. To this end peptide mimetics for the polypeptides may be preferred that are not cleaved by human proteasomes.

The polypeptides, nucleic acid molecules, gene therapy vectors or cells described herein may comprise different types of carriers depending on whether they are to be administered in solid, liquid or aerosol form, and whether they need to be sterile for such routes of administration as injection.

The active agent of present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, directly, via a catheter, via a lavage, in cremes, in lipid compositions (e.g., liposomes), locally applied by sponges or by other method or any combination of the forgoing as would be known to one of ordinary skill in the art (see, for example, Remington's Pharmaceutical Sciences, 18th Ed. Mack Printing Company, 1990, incorporated herein by reference).

Such administering can also be performed, for example, once, a plurality of times, and/or over one or more extended periods. A single injection is preferred, but repeated injections over time (e.g., quarterly, half-yearly or yearly) may be necessary in some instances. Such administering is also preferably performed using an admixture of polypeptides, nucleic acids, gene therapy vectors or cells and a pharmaceutically acceptable carrier. Pharmaceutically acceptable carriers are well known to those skilled in the art and include, but are not limited to, 0.01-0.1 M and preferably 0.05 M phosphate buffer or 0.8% saline.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

Additionally, such pharmaceutically acceptable carriers can be aqueous or non-aqueous solutions, suspensions, and emulsions, most preferably aqueous solutions. Aqueous carriers include water, alcoholic/aqueous solutions, emulsions and suspensions, including saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as Ringer's dextrose, those based on Ringer's dextrose, and the like. Fluids used commonly for i.v. administration are found, for example, in Remington: The Science and Practice of Pharmacy, 20th Ed., p. 808, Lippincott Williams S-Wilkins (2000). Preservatives and other additives may also be present, such as, for example, antimicrobials, antioxidants, chelating agents, inert gases, and the like.

The phrase "pharmaceutically acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

The composition can be formulated in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like. As used herein, a "therapeutically effective amount" for the pharmaceutical composition includes, without limitation, the following amounts and ranges of amounts:

For a composition comprising a polypeptide according to the invention or preferred embodiment thereof: (i) from about $1\times10^{-3}$ to about $1\times10^{6}$ µg/kg body weight; (ii) from about $1\times10^{-2}$ to about $1\times10^{5}$ µg/kg body weight; (iii) from about $1\times10^{-1}$ to about $1\times10^{4}$ µg/kg body weight; (iv) from about $1\times10^{-1}$ to about $1\times10^{3}$ µg/kg body weight; (v) from about $1\times10^{-1}$ to about $1\times10^{2}$ µg/kg body weight; (vi) from about $1\times10^{-1}$ to about $0.5\times10^{2}$ µg/kg body weight; (vii) about $1\times10^{-2}$ µg/kg body weight; (viii) about $1\times10^{1}$ µg/kg body weight; (ix) about 10 µg/kg body weight (x) about $1\times10^{2}$ µg/kg body weight; (xi) about $5\times10^{3}$ µg/kg body weight.

For a composition comprising cells according to the invention or preferred embodiment thereof: (i) from about $1\times10^{2}$ to about $1\times10^{8}$ cells/kg body weight; (ii) from about $1\times10^{3}$ to about $1\times10^{7}$ cells/kg body weight; (iii) from about $1\times10^{4}$ to about $1\times10^{6}$ cells/kg body weight; (iv) from about $1\times10^{4}$ to about $1\times10^{5}$ cells/kg body weight; (v) from about $1\times10^{5}$ to about $1\times10^{6}$ cells/kg body weight; (vi) from about $5\times10^{4}$ to about $0.5\times10^{5}$ cells/kg body weight; (vii) about $1\times10^{3}$ cells/kg body weight; (viii) about $1\times10^{4}$ cells/kg body weight; (ix) about $5\times10^{4}$ cells/kg body weight; (x) about $1\times10^{5}$ cells/kg body weight; (xi) about $5\times10^{5}$ cells/kg body weight; (xii) about $1\times10^{6}$ cells/kg body weight; and (xiii) about $1\times10^{7}$ cells/kg body weight.

Human body weights envisioned include, without limitation, about 5 kg, 10 kg, 15 kg, 30 kg, 50 kg, about 60 kg; about 70 kg; about 80 kg, about 90 kg; about 100 kg, about 120 kg and about 150 kg.

Dosages of the viral gene therapy vector will depend primarily on factors such as the condition being treated, the selected gene, the age, weight and health of the patient, and may thus vary among patients. For example, a therapeutically effective human dosage of the viral vectors may be preferably in the range of from about 1 to about 1000 ml, preferably 10 to 100 ml, preferably 20 to 50 ml of saline solution containing concentrations of from about $1\times10^{5}$ to $1\times10^{12}$ preferably $1\times10^{6}$ to $1\times10^{11}$ more preferably $1\times10^{7}$ to $1\times10^{10}$ plaque forming units (pfu)/ml viruses. The dosage will be adjusted to balance the therapeutic benefit against any side effects. The levels of expression of the selected gene can be monitored to determine the selection, adjustment or frequency of dosage administration.

As used herein "inducible expression" or "conditional expression" relates to a state, multiple states or system of an expression of the polypeptide, wherein the polypeptide is preferably not expressed, or in some embodiments expressed at negligible or relatively low levels, unless there is the presence of one or more molecules (an inducer) or other set of conditions in the cell that allows for polypeptide expression. Inducible promoters may relate to either naturally occurring promoters that are expressed at a relatively higher level under particular biological conditions, or to other synthetic promoters comprising any given inducible element. Inducible promoters may refer to those induced by particular tissue- or micro-environments or combinations of biological signals present in particular tissue- or micro-environments, or to promoters induced by external factors, for example by administration of a small drug molecule or other externally applied signal. As used herein, "treatment" of a disease or "treating" a subject afflicted with a disorder shall mean slowing, stopping or reversing the disorder's progression. In the preferred embodiment, treating a subject afflicted with a disorder means reversing the disorder's progression, ideally to the point of eliminating the disorder itself. As used herein, ameliorating a disorder and treating a disorder are equivalent. The treatment of the present invention may also, or alternatively, relate to a prophylactic administration of the active agents described herein. Such a prophylactic administration may relate to the prevention of any given medical disorder, or the prevention of development of said disorder, whereby prevention or prophylaxis is not to be construed narrowly under all conditions as absolute prevention. Prevention or prophylaxis may also relate to a reduction of the risk of a subject developing any given medical condition, preferably in a subject at risk of said condition.

"Combined administration" may relate to concurrent and/or sequential administration of said polypeptide prior to, during and/or subsequent to said adjuvant, check point inhibitor and/or further treatment. Combined treatment shall also include a combination treatment regimens comprising multiple administrations of either therapeutic component of the treatment. Further embodiments of combined administration are provided herein.

Combined administration encompasses simultaneous treatment, co-treatment or joint treatment, and includes the administration of separate formulations of the polypeptide of the present invention with said adjuvant, check point inhibitor and/or further treatment, whereby treatment may occur within minutes of each other, in the same hour, on the same day, in the same week or in the same month or within 3 months as one another. Sequential administration of any given combination of combined agents is also encompassed by the term "combined administration". A combination medicament, comprising one or more of said polypeptide, said adjuvant, check point inhibitor and/or further treatment, may also be used in order to co-administer the various components in a single administration or dosage.

The term "vaccine" in the context of the present invention relates to a biological preparation that provides active acquired immunity to a particular disease, such as cancer, a pathogen or an infectious agent, such as bacteria or viruses. In the context of the present invention, NKG2C+ NK cells may be considered to provide adapted or acquired immunity. A vaccine can contain an agent or antigen that resembles or is derived from a disease-causing microorganism. Vaccines can be made from weakened, attenuated, mutated or killed forms of the pathogen, its toxins or one of its surface proteins. The agent stimulates the body's immune system to recognize the agent as a threat, destroy it, and recognize and destroy any pathogens or structures comprising the agent or antigen of the vaccine that it later encounters. Vaccines can be prophylactic (example: to prevent or ameliorate the effects of a future infection by a natural or "wild" pathogen), or therapeutic, such as specific cancer vaccines.

As used herein, the term "sample" is a biological sample that is obtained or isolated from the patient or subject. "Sample" as used herein may, e.g., refer to a sample of bodily fluid or tissue obtained for the purpose of diagnosis, prognosis, or evaluation of a subject of interest, such as a patient. Preferably herein, the sample is a sample of a bodily fluid, such as blood, serum, plasma, cerebrospinal fluid, urine, saliva, sputum, pleural effusions, cells, a cellular extract, a tissue sample, a tissue biopsy, a stool sample and the like. In the context of the present invention, any kind of sample comprising pathogenic cells potentially expressing HLA-E and a peptide comprising an amino acid sequence according to SEQ ID NO 1 or 2, such as cancer cells or cells that may comprise reactivated HCMV.

EXAMPLES

The invention is further described by the following examples. These are not intended to limit the scope of the invention, but represent preferred embodiments of aspects of the invention provided for greater illustration of the invention described herein.

Methods Employed in the Examples

Human Subjects

All analyses of human data were carried out in compliance with the relevant ethical regulations. Healthy blood donors gave informed consent at DRK Dresden, Germany and buffy coats from donors with defined HCMV-serostatus were obtained as approved by Charité ethics committee (EA1/149/12). PBMCs were isolated by density gradient centrifugation (Ficoll Paque Plus, GE Healthcare) and PBMCs of HCMV+ donors were screened for the presence of adaptive NKG2C+ NK cells as previously described[56]. In brief, co-expression analysis was employed to detect adaptive CD2+CD57+ILT2+Siglec-7−NKp30−NKG2A− NK cells within the CD56$^{dim}$ NKG2C+ population. CD56+ cells were MACS-enriched (CD56 MicroBeads, Miltenyi Biotec) and either used directly or cryopreserved in fetal bovine serum (FBS; Biowest) containing 10% DMSO (Sigma).

Patients undergoing allogeneic hematopoietic stem cell transplantation either at the Department of Hematology, Oncology and Tumor Immunology, Charité—Universitätsmedizin Berlin or at the Department of Hematology, Hemostasis, Oncology and Stem Cell Transplantation, Hannover Medical School gave informed consent (Charité ethics committee approval EA1/1/169/14; Hannover Medical School institutional review board approval #1303-2012, #2032-2013, #2604-2014, and #2604-2015; the latter cohort has been described previously[57]). PBMCs were isolated by density gradient centrifugation on the day of blood donation and cryopreserved in FBS containing 10% DMSO. Serum samples from the Charité cohort were handled and stored at Labor Berlin—Charité Vivantes GmbH.

Cells and Cell Lines

K562/HLA-E[21] (kindly provided by E. Weiss, Ludwig Maximilian University) and RMA-S/HLA-E[58] (kindly provided by J. Coligan, National Institutes of Health) cells were maintained in complete medium (RPMI-1640 containing glutamine and supplemented with 10% [v/v] FBS, 20 µM β-mercaptoethanol, and 100 U/ml Penicillin-Streptomycin; all Thermo Fisher) in the presence of 400 µg/ml Hygromycin B and 1 mg/ml G418 (both InvivoGen), respectively. RMA-S/HLA-E were transfected by electroporation (Cell Line Nucleofector Kit T, Lonza) with pUNO1-hLFA3a plasmid (InvivoGen). RMA-S/HLA-E/LFA-3 were FACS-sorted for high LFA-3 expression and selected and maintained in complete medium containing both 400 µg/ml Hygromycin B and 25 µg/ml Blasticidin (InvivoGen). Primary human umbilical vein endothelial cells (HUVECs) were purchased from Lonza and maintained in EGM-2 (Lonza) according to the manufacturer's instructions.

Amplification, Sequencing, and Analysis of UL40-Encoded Peptide Sequences

DNA was extracted from serum or plasma samples using QIAmp DNA Micro Kit (Qiagen) according to the manufacturer's instructions. A partial HCMV UL40 sequence was amplified with a nested PCR approach (Table 5 for primer sets) using the AccuPrime high fidelity DNA Polymerase (ThermoFisher) and PCR products were sequenced at Eurofins Genomics. At least 2 independent DNA extractions, PCRs, and sequencing reactions were performed for each sample. 165 published UL40 sequences were obtained from GenBank (NCBI) and combined with 52 newly determined sequences from patient samples. The integrated data set was analyzed using BioEdit (Ibis Biosciences), SerialCloner (SerialBasics), and WebLogo[59] (University of California).

HLA E Surface Stabilization

HLA-E surface stabilization was induced as described previously[30]. In brief, 300 µM synthetic peptides (Peptides&Elephants) were added to target cells cultured at a density of 2×10$^6$ cells/ml in serum-free Opti-MEM (ThermoFisher) and incubated for 16 h at 37° C. Peptide-pulsed cells were either stained for FACS analysis of HLA-E surface expression or washed with complete media and used in co-cultures. For pulse-chase experiments, cells were pulsed as above, washed twice, and resuspended in Opti-MEM without peptide. HLA-E surface expression was monitored by FACS analysis at indicated time points.

In Vitro Stimulation of NK Cells

CD56+ MACS-enriched cells were stained with viability dye, CD3, and CD56, FACS-sorted for viable CD3−CD56+ NK cells, and rested overnight in complete medium. Purified NK cells were stimulated by co-culture with peptide-pulsed (300 µM) irradiated (30 Gy) target cells at a 2:1 NK:target ratio for 6 h in the presence of 300 µM synthetic peptides. Anti-CD107a (Table 4) antibody was added at the start of the assay and GolgiStop and GolgiPlug (both BD Biosciences) were added 1 h after start of the stimulation.

For blocking experiments, rested FACS-sorted viable CD3− CD56$^{dim}$ NKG2A− NKG2C+ NK cells were treated with 20 µg/ml IgG1 isotype control or anti-CD94 antibody (both RnD Systems) for 15 min prior to start of the co-culture.

For infection experiments, 2.5×10$^4$ HUVEC homozygous for both HLA-C1 and HLA-Bw4 seeded in 48-well plates were infected with HCMV TB40R variants in serum-free media at a multiplicity of infection of 3-5. After 24 h, HUVECs were washed and further incubated in EGM-2. At 48 h post infection, HUVECs were washed and co-cultured with 5×10$^4$ rested or overnight IFN-α-primed (25 ng/ml; Miltenyi) FACS-sorted viable CD3− CD56+ NK cells for 6 h. Anti-CD107a antibody (Table 4) was added at the start of the assay and GolgiStop and GolgiPlug (both BD Biosciences) were added 1 h after start of the stimulation.

Cytotoxicity Assays

CD56+ MACS-enriched cells were stained with viability dye, CD3, and CD56, FACS-sorted for viable CD3− CD56+ NK cells, and rested overnight in complete medium. Varying numbers of purified NK cells were co-cultured with 2×10$^4$ CellTrace violet (ThermoFisher)-labeled peptide-pulsed (3000) target cells resulting in NK:target ratios ranging from 0.1 to 10. To control for spontaneous cell death, target cells were cultured in the absence of NK cells. After 6 h, cell suspensions were stained for viability of target cells using Fixable Viability Dye eFluor780 (ThermoFisher) and analyzed by flow cytometry. Cytotoxicity (%) was calculated as follows: (% dead target cells in experimental condition−% dead target cells in spontaneous control)/(100%−% dead target cells in spontaneous control)×100.

In Vitro Culture of NK Cells

CD56+ MACS-enriched cells from HCMV− donors were stained with viability dye, CD3, and CD56, FACS-sorted for viable CD3− CD56$^{dim}$ NK cells, and rested overnight in complete medium. Purified CD56$^{dim}$ NK cells were labeled with 2 µM CellTrace violet (Thermo Fisher) according to the manufacturer's instructions. 5×10$^5$ labeled NK cells were cultured with 1×10$^5$ peptide-pulsed (3000) irradiated (30 Gy) target cells in complete medium containing 10 ng/ml IL-15 (Miltenyi Biotec) in U-bottom 96-well plates (Greiner Bio-One) for the indicated times. Complete medium containing IL-15 was replaced every third to fourth day. On days 4, 7, and 11 of culture, 1×10$^5$ fresh peptide-pulsed irradiated target cells were added to the cultures.

Where indicated, 10 ng/ml IL-12 (Miltenyi Biotec) and 100 ng/ml IL-18 (MBL) were added at the start of co-cultures. After 20 h of culture, the cells were washed 3 times and resuspended in complete medium containing 10 ng/ml IL-15. Control wells without IL-12/18 were treated equally. To determine NKG2C+ NK cell numbers per µl of culture medium, CountBright Absolute Counting Beads (ThermoFisher) were used according to the manufacturer's instructions.

Proliferation and replication indices[60] of NKG2C+ cells were calculated using the proliferation analysis platform included in FlowJo v9.9 (FlowJo LLC) and normalized to those of NKG2C− cells in the same condition.

For assessment of KIR ligands present in individual donors to determine educating KIR, DNA extracted from PBMCs was HLA-B and HLA-C typed at low and high resolution, respectively, by the Center for Transfusion Medicine and Cell Therapy, Charité—Universitätsmedizin Berlin.

Flow Cytometry

Cell suspensions were stained in different combinations of fluorochrome-conjugated antibodies (Table 4), following established guidelines[61]. Dead cells were excluded using LIVE/DEAD Fixable Violet Dead Cell Stain Kit, Fixable Viability Dye eFluor780 (both ThermoFisher), or Zombie Aqua Fixable Viability Kit (BioLegend). For intracellular staining, cells were fixed with 2% PFA (EMS Sciences) and permeabilized with Permeabilizing Solution 2 (BD Biosciences) according to the manufacturer's instructions. Staining of HCMV-IE in HUVEC was performed using the Foxp3/Transcription Factor Staining Buffer Set (eBioscience) according to the manufacturer's instructions. Data were acquired on a LSR Fortessa or FACSymphony (both BD Biosciences). FlowJo v9.9 and vX (FlowJo LLC) as well as SPICE[62] (NIAID) software were used for analysis. ARIA, ARIA II, or Influx instruments (all BD Biosciences) were used for cell sorting experiments.

Expression Analysis of HCMV UL40

RNA of HUVECs was extracted at indicated time points post infection using the Nucleospin RNA kit (Macherey Nagel) according to the manufacturer's instructions. Viral genomic DNA was eliminated by in-solution rDNase digestion for 10 min at 37° C. RNA was re-purified by addition of 2.5 volumes ethanol (Sigma) and 0.1 volume 3 M sodium acetate (Thermo Fisher) and incubation at −20° C. overnight. Precipitated RNA was washed with 70% ethanol, dried, and resuspended in RNase-free H$_2$O. 50 ng RNA were reverse transcribed with TaqMan Reverse Transcription Reagents (Applied Biosciences). Quantitative real-time PCR was performed using Maxima SYBR Green/ROX qPCR Master Mix (Thermo Fisher) in a StepOnePlus system (Applied Biosciences) using UL40_nested and hGAPDH primer pairs (Table 5). Specificity of amplification was assessed by melting curve analysis, gel electrophoresis, and controls without reverse transcription to confirm complete digestion of genomic DNA.

Generation of HCMV Mutant Viral Strains

HCMV mutants encoding different UL40 peptides were constructed using the bacterial artificial chromosome (BAC) TB40 BAC4[63] containing the genome of the HCMV strain TB40/E. For reinsertion of viral genes US2-US6 deleted in TB40 BAC4, two-step replacement mutagenesis based on homologous recombination in E. coli[64] was performed utilizing the shuttle plasmid pUH15[65]. The resulting BAC TB40R was further modified by addition of the Cre gene and loxP sites flanking the BAC vector sequences to allow self-excision upon introduction into HCMV-permissive cells. A gpt gene in BAC TB40R was replaced with a tetracycline resistance marker by en passant mutagenesis in E. coli strain GS1783[66] and utilizing a PCR fragment amplified with primers US2-lox-tet.for (see Table 6 for primer sequences using during mutagenesis) and G-lox-tet.rev and template plasmid pori6K-Tet (M. Messerle, unpublished). The PCR product was recombined with TB40R, giving rise to TB40R-lox-Tet, into which the Cre recombinase sequences were inserted. To this end, a template plasmid was generated containing sequences for a polyomavirus promoter, an intron-containing Cre gene with internal insertion of a kanamycin-resistance marker (kan$^R$) and a loxP site. The kan$^R$ marker (with an adjacent I-SceI restriction site) was amplified with primers pIC1.for and MC-Cre.rev with plasmid pori6K-RIT (M. Messerle unpublished) as template, and the PCR fragment for the Cre gene was amplified with primers kan$^R$-ISce.for and pIC.rev and template plasmid pMC-Cre-Intron (E. M. Borst, unpublished; pMC-Cre-Intron contains the Cre gene of plasmid pGS403[67], the latter kindly provided by G. Smith, Northwestern University). The resulting PCR products were added to vector pIC1[68] next to a loxP site by Gibson assembly[69] using the Gibson Assembly Master Mix according to the manufacturer's instructions (NEB). Integrity of the plasmid pIC-kan$^R$-Cre-Intron was verified by restriction analysis and sequencing. A PCR fragment was produced from pIC-kan$^R$-Cre-Intron with primer pair loxPUS2.for and KanRITyellow.rev, and recombined with TB40R-lox-Tet, followed by seamless excision of the kan$^R$ cassette as described[66]. The final HCMV BAC, TB40R-Cre, served for mutagenesis of the UL40 sequences. To mutate the UL40 region, the following primer pairs were used with pori6K-RIT as template: UL40_VMAPRTLIL.for and UL40_VMAPRTLIL.rev, UL40_VMAPRTLFL.for and UL40_VMAPRTLFL.rev, and UL40_VMAPQSLLL.for and UL40_VMAPQSLLL.rev. En passant mutagenesis using the resulting PCR products and BAC TB40R-Cre, followed by excision of the kan$^R$ marker as reported[66], gave rise to recombinant HCMV BAC genomes containing UL40 genes encoding for VMAPRTLFL (SEQ ID NO. 2), VMAPRTLIL (SEQ ID NO. 3), or VMAPQSLLL (SEQ ID NO. 4) peptides, respectively. Successful mutagenesis was confirmed by restriction analysis and sequencing of the relevant parts within the BAC genomes. Virus mutants were reconstituted by transfection of human foreskin fibroblasts (HFF; Merck Millipore; cultured as outlined elsewhere[64]) by adenofection as described[70]. Virus stock was produced by seeding 1×10$^7$ HFF into four T75 flasks, followed by infection the next day in serum-free medium at a multiplicity of infection of 1, followed by centrifugal enhancement at 950 g for 30 min. Five days post infection, supernatants were harvested, cleared from cellular debris by centrifugation at 3,500 g for 45 min, virus was pelleted by ultracentrifugation in an SW32 rotor at 143,000 g for 60 min, and stored in 50 mM Tris-HCl pH 7.8 containing 12 mM KCl, 5 mM Na$_2$EDTA, and 20% FBS at −80° C. Viral titers were determined by plaque assay on HFF[64].

Mathematical Model of NK Cell Proliferation

For mathematical analysis of the kinetic NK cell proliferation data, the following mathematical model was used:

$$N_0(t) = (1 - \varphi(t)) + \chi e^{-k_d t} \quad (1)$$

$$\frac{dN_1}{dt} = 2\psi(t) - \psi(t - t_{div})e^{-k_d t_{div}} - k_d N_1(t), N_1(0) = 0$$

$$N_i(t) = (2e^{-k_d t_{div}})^{i-1} N_1(t - [i-1]t_{div}), N_i(t) = 0 \text{ for } t \leq 0,$$

$$i = 2, \ldots, \infty$$

Here, $N_i(t)$ is the number of cells in the i-th generation at time t, given as fold-change with respect to the cell number at time 0. $\chi$ is the fraction of non-dividing cells, $\psi(t)$ is a normalized probability density determining the time until the first division of each cell (also known as precursor frequency), and $\varphi(t)$ is the cumulative probability distribution to $\psi(t)$. Further, $k_d$ is the death rate, and $t_{div}$ is the division time, that means the time required for completion of each cell division after the first division, which is assumed to be constant and deterministic. From Equation (1), we may compute the total cell number at each time point as $C(t) = \Sigma N_{i=0}^{\infty} N_i(t)$. Equation (1) is a variant of the well-established Gett/Hodgkin model[38], for which a convenient analytical formulation was described[71]. That analytical description considers the dynamics of dividing cells after their first division (generations $N_1$, $N_2$, ... ). Since the cell number data in our study show substantial initial cell death before the onset of clonal expansion, we additionally consider generation $N_0$. That generation consists of dividing cells that have not yet divided (first term), and non-dividing cells, which we take as decaying with the same death rate as dividing cells (second term). To be consistent with our observation that almost all cells present at day 7 have divided at least once across conditions (FIG. 7 and FIG. 10a), in Equation (1), we set the fraction of non-dividing cells to $\chi = 0.05/e^{-k_d t_p}$, $t_p = 6$ days. Thus, in the model, the non-dividing cells have dropped to 5% of their initial population on the 6$^{th}$ day after stimulation. For precursor frequencies, we have experimental measurements at days 1 through 7 from the CellTrace data analysis (FIG. 7e and FIG. 10a). The means of measured values obtained from n=6 individual donors are well described by the cumulative distribution function to the gamma distribution $$\psi(t) = \frac{t^{\alpha-1} e^{-\beta t}}{\Gamma(\alpha)\beta^{-\alpha}}$$

(FIG. 10b, c), which were therefore used in simulations of Equation (1). Here, $\Gamma(x)$ is the Euler gamma function, and we determined the parameters $\alpha,\beta$ by nonlinear optimization. Thus, the only free parameters were division time $t_{div}$ and death rate $k_d$. These values were obtained by non-linear optimization with respect to experimentally measured cell numbers. For all curve fitting procedures, the function fitnlm in Matlab, (Mathworks, version R2017b) was used. Specifically, the distribution $\varphi(t)$ of first division times from the measured precursor frequencies, and the division time $t_{div}$ as well as death rate $k_d$ were determined by fitting Equation (1) to kinetic cell number data. In both cases, experimentally obtained kinetic data was averaged across donors and the variability between donors at each time-point was considered by weighting the averaged data by the weights $w_l = 1/\sigma_l^2$, where $\sigma_l$ is the standard deviation across donors at the l-th measurement time-point.

Validation of Methylation Profiles Using Next Generation Sequencing

For PCR amplicon design, locus-specific primers were designed using an in-house bisulfite primer design tool (see Table 5 for primer sequences). To validate methylation profiles of IFNG regulatory region CNS1 after in vitro culture of NK cells from HCMV$^-$ donors, samples were sorted for viable CD56$^+$ NKG2C+ cells at day 7 and DNA was isolated using QIAmp DNA Micro kit (Qiagen) according to the manufacturer's instructions. Genomic DNA was bisulfite converted using the EZ DNA Methylation Gold Kit (Zymo Research) following the manufacturer's protocol and PCR was performed with Hot FirePol DNA Polymerase and Buffer (both Solis BioDyne) using the following program: 15 min 95° C.; 40 cycles 1 min 95° C., 2.5 min 56° C., and 40 s 72° C.; followed by 7 min 72° C. PCR products were purified using Agencourt AMPure XP Beads (Beckman Coulter). Amplicon NGS tags were finalized with HotStart-Taq polymerase and buffer (both Qiagen) using the following program: 15 min 97° C.; 5 cycles 30 s 97° C., 30 s 60° C., and 30 s 72° C. Purified samples were quantified by Qubit High Sensitivity Assay (Life Technologies) and diluted to 10 nM. Finally, all samples were pooled and amplicons were pair-end sequenced (2×300 nt) with two index reads using a MiSeq reagent kit V2 chemistry on Illumina MiSeq (both Illumina). Raw sequencing data was quality controlled using FastQC (v0.10.3; on the World-Wide-Web at: bioinformatics.babraham.ac.uk/projects/fastqc/) and trimmed for adaptors and low quality bases using cutadapt (v1.3; on the internet at: code.google.com/p/cutadapt/) and Trim Galore! (v0.3.3; on the World-Wide-Web at: bioinformatics.babraham.ac.uk/projects/trim_galore/). Paired reads were joined using FLASh (on the internet at: ccb.jhu.edu/software/FLASH/). Reads were sorted by (i) the NGS barcode adaptors to assign Sample ID and (ii) the initial 15 bp to assign amplicon ID. Sorted data was loaded into BiQAnalyzer HiMod software (on the internet at: biq-analyzer-himod.bioinf.mpi-inf.mpg.de/) using the following settings: analyzed methylation context set to "C", minimal sequence identity set to 0.9 and minimal conversion rate set to 0.95. Filtered high quality reads were used for methylation calls of the respective CpG and analyzed using in-house R-scripts.

Gene Expression Analyses Using Next Generation Sequencing

To assess transcriptome profiles after in vitro culture of NK cells from HCMV$^-$ donors, samples were sorted for viable CD56$^+$ NKG2C+ cells at day 7 and total RNA was isolated using RNeasy Plus Micro kit (Qiagen) according to the manufacturer's instructions. Illumina libraries were prepared using Smart-Seq v4 mRNA Ultra Low Input RNA Kit (Clontech) and Nextera® XT DNA Sample Preparation Kit (Illumina), with up to 10 ng of purified cDNA, according to the manufacturer's instructions. Libraries were paired-end sequenced (2×75 bp) on an Illumina NextSeq500 device. Raw sequences were mapped to human GRCh37/hg19 genome with TopHat2[72] in very-sensitive settings for Bowtie2[73] and GENCODE annotation release 19 (GRCh37.p13). Per gene counts were calculated using featureCounts[74] and gene expression analyses were performed using DESeq2 1.18[75]. Heat maps for selected genes were generated using z-scores of rlog-transformed read counts, clustered by Pearson correlation and Ward minimum variance method.

Statistical Analysis

Statistical parameters including sample size, employed statistical tests, and statistical significance are reported in the Figure Legends. Two groups of paired samples were compared with two-tailed Wilcoxon test, while three or more groups of paired samples were analyzed using Friedman test with Dunn's post test to control for multiple comparisons. Datasets of paired samples containing two variables (e.g. different peptide sequences and different concentrations) were compared with repeated-measures two-way ANOVA with Bonferroni correction. First order kinetics of decay in HLA-E surface expression obtained from pulse-chase experiments were analyzed by linear regression and ANCOVA. Statistical analyses were performed with Graph Pad PRISM 7 (Graph Pad Software) using a confidence level of 0.95 and P-values above 0.05 were considered not significant.

Method for Determining the Surface Expression of HLA-E

Tumor cells from patients are tested for the expression of HLA-E by staining with the commercially available antibody clone 3D12 and analysis by flow cytometry.

Methods for Determining the Expression of HLA-G

Transcripts of HLA-G are detected by an isoform specific RT-PCR. RNA from tumor cells is reversely transcribed to dDNA and HLA-G transcripts amplified using the primers G.257F and G.936R (Paul, P., et al. (2000). "HLA-G, -E, -F pre workshop: tools and protocols for analysis of non-classical class I genes transcription and protein expression." Human Immunology 61(11): 1177-1195).

Cycling Conditions:

| Initial denaturation | 94° C. 120 seconds | |
|---|---|---|
| Denaturation | 94° C. 60 seconds | 35 cycles |
| Primer annealing | 60° C. 60 seconds | |
| Primer elongation | 72° C. 90 seconds | |
| Final elongation | 72° C. 300 seconds | |
| Pause | 4° C. | |

Specific bands are detected at 848 bp (isoform G6), 726 bp (G1, G4, G5), 450 bp (G3), 174 bp (G2). As a positive control, cDNA produced from the HLA-G expressing cell line JEG-3 is used as a standard for the specific bands.

For a quantitative assessment of the isoforms HLA-G1, -G4, -G5 and G6, a quantitative RT-PCR is performed using the primers GqF and GqR. Expected amplicon size: 123 bp Cycling conditions:

| Initial denaturation | 95° C. 600 seconds | |
|---|---|---|
| Denaturation | 94° C. 15 seconds | 40 cycles |
| Primer annealing | 60° C. 30 seconds | |
| Primer elongation | 72° C. 30 seconds | |

Primers:

| G.257F | 5'-GGAAGAGGAGACACGGAACA-3' | (SEQ ID NO. 67) |
|---|---|---|
| G.936R | 5'-GCAGCTCCAGTGACTACAGC-3' | (SEQ ID NO. 68) |
| GqF | 5'-GAGGAGACACGGAACACCAAG-3' | (SEQ ID NO. 69) |
| GqR | 5'-GTCGCAGCCAATCATCCACT-3' | (SEQ ID NO. 70) |

To assess expression of HLA-G on the protein level, cells are stained with the commercially available antibody clones MEM-G9 and 87G and analyzed by flow cytometry.

Patients

The characteristics of the patients used in the present examples are summarized in Table 3. Abbreviations use in Table 3: Abbreviations: AML, acute myeloid leukemia; ALL, acute lymphoid leukemia; ATG, anti-thymocyte globulin; BCNU: 1,3-bis(2-chloroethyl)-1-nitrosourea [carmustine]; Bu, busulfan; CML, chronic myeloid leukemia; CsA, cyclosporine A; Cy, cyclophosphamide; FLAMSA, fludarabine-cytarabine-amsacrine; Flu, fludarabine; GvHD, graft-versus-host disease; HCMV, human cytomegalovirus; MDS, myelodysplastic syndrome; Mel, melphalan; MMF: mycophenolate mofetil; MTX, methotrexate; TBI, total body irradiation; Thio, thiopeta; Tx, transplantation.

Results of the Examples

Summary of the Results

Natural Killer (NK) cells are innate lymphocytes lacking antigen-specific rearranged receptors, a hallmark of adaptive lymphocytes. In some individuals infected by human cytomegalovirus (HCMV), an NK-cell subset expressing the activating receptor NKG2C undergoes clonal-like expansion, partially resembling anti-viral adaptive responses. However, the viral ligand driving the activation and differentiation of adaptive NKG2C+ NK cells remains unclear. Here, we demonstrate that adaptive NKG2C+ NK cells differentially recognize distinct HCMV strains encoding variable UL40 peptides, which—in combination with pro-inflammatory signals—control the expansion and differentiation of adaptive NKG2C+ NK cells. Thus, we propose that polymorphic HCMV peptides contribute to shape the heterogeneity of adaptive NKG2C+ NK-cell populations among HCMV-seropositive individuals.

Example 1: Sequence Variations in HCMV UL40-Encoded Peptides Control the Activation of Adaptive NKG2C+ NK Cells Elevated frequency of NKG2C+ NK cells as well as an altered receptor repertoire, including preferential expression of CD2 combined with low levels of Siglec-7, NKG2A, and FcεR1γ, is a central feature of the NK-cell repertoire in healthy HCMV+ individuals (5, 6, 7, 8, 10). However, both the percentage of NKG2C+ NK cells and their CD2+ Siglec-7− NKG2A− FcεR17− adaptive phenotype are prominently heterogeneous, as indicated by the respective coefficients of variation (CV) (FIG. 1a, b). This heterogeneity suggests the involvement of variable host or HCMV factors in driving the expansion and differentiation of adaptive NKG2C+ NK cells among different individuals. In quest of virus factors driving this phenomenon, we performed an integrated analysis of 217 clinical isolates obtained by combining sequencing of viral UL40 DNA with a meta-analysis of reported HCMV isolates. The analysis corroborated considerable heterogeneity within the UL40-encoded peptide repertoire (30, 31) and the sequences VMAPRTLIL (SEQ ID NO. 3), VMAPRTLLL (SEQ ID NO. 4), and VMAPRTLVL (SEQ ID NO. 5), were most commonly represented (FIG. 2a, b), while 31.2% of the strains encoded alternative and not yet described HCMV UL40 sequences, such as VMAPRTLLM (SEQ ID NO. 27), VMGPRTLLL (SEQ ID NO. 35), VMAPWTLLL (SEQ ID NO. 17), or VMAPRTLFL (SEQ ID NO. 2) (FIG. 2a, Table 2). We next asked whether high sequence variability within the HCMV UL40 region could impact on the capacity to stabilize HLA-E and to activate NKG2C+ NK cells. To address this question, murine TAP-deficient RMA-S cells transfected with human β2-microglobulin and HLA-E (RMA-S/HLA-E) were pulsed with a selection of peptides from the sequence analysis, namely VMAPRTLIL (SEQ ID NO. 3), VMAPRTLVL (SEQ ID NO. 5), VMAPRTLFL (SEQ ID NO. 2), and VMAPQSLLL (SEQ ID NO. 12), the latter serving as control due to its poor interaction with NKG2 receptors (30). Stimulation of purified NK cells with peptide-pulsed RMA-S/HLA-E revealed that VMAPRTLVL (SEQ ID NO. 5), VMAPRTLIL (SEQ ID NO. 3), and VMAPRTLFL (SEQ ID NO. 2) differentially triggered TNF, IFN-γ, CD107a, and CCL3 expression by adaptive NKG2C+ NK cells from healthy HCMV+ individuals, while no activation was detected when using VMAPQSLLL (SEQ ID NO. 12)-pulsed targets. Notably, a gradient in the ability of peptides to induce NKG2C+ NK-cell effector functions could be consistently observed (VMAPRTLFL (SEQ ID NO. 2)>VMAPRTLIL (SEQ ID NO. 3)>VMAPRTLVL) (SEQ ID NO. 5) (FIG. 2c, d). Differential activation was also detected in cytotoxicity assays (FIG. 1d). Importantly, the ability of peptides to activate NKG2C+ NK cells with different efficiency did not depend on their intrinsic ability to bind HLA-E: with the exception of VMAPQSLLL (SEQ ID NO. 12), the analyzed UL40-encoded peptides equally stabilized HLA-E at saturating concentrations (FIG. 1e), which is in line with comparable binding affinities predicted by the NetMHC 4.0 algorithm 32 (FIG. 1f). Moreover, pulse-chase experiments demonstrated that the decay in surface HLA-E of VMAPRTLIL (SEQ ID NO. 3)- and VMAPRTLFL (SEQ ID NO. 2)-pulsed cells followed identical kinetics (FIG. 1g). Along this line, elevated activation of adaptive NKG2C+ NK cells by VMAPRTLFL (SEQ ID NO. 2) was consistent upon pulsing with sub-optimal peptide concentrations, at which VMAPRTLIL (SEQ ID NO. 3) was more efficiently stabilizing HLA-E (FIG. 2e; FIG. 1h). Further corroborating specific receptor-mediated recognition, activation was restricted to NKG2C+ NK cells and entirely inhibited in the presence of an anti-CD94 blocking antibody (FIG. 1i, j). Since both NKG2A and NKG2C can recognize HLA-E/peptide complexes, we co-cultured purified NK cells with K562 cells transfected with HLA-E (K562/HLA-E) pulsed with varying peptide concentrations. As opposed to murine RMA-S, human K562 represent susceptible targets for all human NK cells, rendering this experimental platform optimally tailored for side by side analysis of adaptive NKG2C+ cell activation and conventional NKG2C− NKG2A+ cell inhibition. In contrast to adaptive NKG2C+ NK-cell activation, NKG2A+ NKG2C− NK cells did not preferentially respond to VMAPRTLFL (SEQ ID NO. 2)-pulsed targets (FIG. 1k), suggesting different functional abilities of NKG2C and NKG2A upon interaction with HLA-E/peptide complexes. Together, these data demonstrate that HCMV isolates encode for a broad range of HLA-E-stabilizing peptides and that recognition of distinct HLA-E/peptide complexes controls the activation of adaptive NKG2C+ NK cells.

Example 2: Co-Stimulatory Signals are Required to Elicit Polyfunctionality of Adaptive NKG2C+ NK Cells Upon Engagement with Sub-Optimal Peptides Since NK cells generally rely on cross-linking of multiple receptors for proficient activation, we next examined whether differences in peptide recognition could be overcome by co-engagement of additional NK-cell receptors. Stimulation with peptide-pulsed K562/HLA-E, which express a broad range of ligands for NK-cell receptors, resulted in overall amplified NKG2C+ cell activation, while the hierarchy among peptides was maintained (FIG. 3a). Since effector functions were strongly decreased by blocking the LFA-3-CD2 axis (11) (FIG. 3b, c), we next examined whether peptides recognized with low or intermediate functional avidity could preferentially benefit from CD2 co-stimulation by using RMA-S/HLA-E transfected with human LFA-3. While stimulation with VMAPRTLFL (SEQ ID NO. 2)-pulsed RMA-S/HLA-E was sufficient to induce consistent co-expression of multiple effector functions (CCL3+ CD107a+ IFN-γ+ TNF+) even in the absence of co-stimulation, engagement of CD2 was required to elicit polyfunctional responses upon stimulation with the VMAPRTLIL (SEQ ID NO. 3) variant (FIG. 4a-d). These findings highlight that recognition of the VMAPRTLFL (SEQ ID NO. 2) peptide is sufficient to induce maximal functionality of adaptive NKG2C+ NK cells, but that engagement of the co-stimulatory receptor CD2 can lower the activation threshold, enabling peptides such as VMAPRTLIL (SEQ ID NO. 3) to optimally trigger multiple effector functions in adaptive NKG2C+ NK cells.

Example 3: Adaptive NKG2C+ NK Cells Differentially Recognize HCMV-Encoded Peptides During Infection To ascertain whether distinct UL40-encoded peptides could be differentially recognized by adaptive NKG2C+ NK cells during infection, we re-inserted the immunomodulatory US2-6 genes into the TB40 BAC4 and genetically modified the UL40 locus of the resulting repaired TB40 (TB40R) HCMV strain to encode either VMAPQSLLL (SEQ ID NO. 12), VMAPRTLIL (SEQ ID NO. 3), or VMAPRTLFL (SEQ ID NO. 2) peptides (FIG. 5a). Upon infection of primary human umbilical vein endothelial cells (HUVEC), UL40 transcripts were abundantly present as early as 16 hours post infection (FIG. 6a) and the genetically modified viruses were equally efficient in infecting HUVEC (FIG. 5b, c) as well as in modulating HLA class I levels (FIG. 6b). In line with previous reports, HCMV infection of HUVEC did not result in HLA-E up-regulation (33) (FIG. 6c). Importantly, adaptive NKG2C+ NK cells displayed significantly elevated TNF, IFN-γ, CD107 and CCL3 expression in response to HUVEC infected with TB40R$^{UL40\_VMAPRTLFL}$ compared to the other strains, while TB40R$^{UL40\_VMAPRTLIL}$ elicited slightly increased activation of selected effector functions (FIG. 6d). Differential activation by HUVEC infected with distinct HCMV strains was further enhanced by IFN-γ treatment, which can prime anti-viral NK-cell functions (34) (FIG. 5d, e). In contrast, NKG2C− NK cells were not affected by virus variants even after IFN-α priming (FIG. 6e). These findings suggest that single amino acid exchanges within the UL40 protein can be differentially recognized by adaptive NKG2C+ NK cells during infection and imply that selected mutations in UL40 modulate adaptive NKG2C+ NK-cell responses.

Example 4: Peptide Recognition Controls Relative Accumulation of NKG2C+ NK Cells from HCMV− Individuals in the Presence of Pro-Inflammatory Signals To examine whether peptide recognition not only affects the differential activation of adaptive NKG2C+ NK cells from HCMV+ individuals, but could also influence the extent of NKG2C+ NK-cell proliferation from HCMV− individuals, purified CD56dim NK cells from HCMV− donors were co-cultured with peptide-pulsed target cells in the presence of IL-15. In the absence of co-stimulation, only the VMAPRTLFL (SEQ ID NO. 2) peptide significantly induced preferential cell division of NKG2C+ NK cells (FIG. 7a-b). However, co-engagement of CD2 synergized with peptide recognition and enabled both the VMAPRTLIL (SEQ ID NO. 3) and the VMAPRTLFL (SEQ ID NO. 2) peptides to drive consistently higher proliferation of NKG2C+ NK cells compared to VMAPQSLLL (SEQ ID NO. 12) (FIG. 8a-c, FIG. 7c). Elevated cell division was reflected in increased absolute counts, although not in frequency, of NKG2C+ NK cells after 7 and 14 days of culture (FIG. 8d-e, FIG. 7d-e). In vivo, CMV generates a systemic inflammatory milieu (35), which is required for the generation of MCMV-specific adaptive Ly49H+ mouse NK cells (36). Integration of pro-inflammatory signals by short-term addition of IL-12 and IL-18 (IL-12/18) to VMAPRTLVL (SEQ ID NO. 5)-, VMAPRTLIL (SEQ ID NO. 3)-, or VMAPRTLFL (SEQ ID NO. 2)-pulsed targets resulted in an increase of NKG2C+ NK-cell absolute counts as well as frequencies compared to the non-activating VMAPQSLLL (SEQ ID NO. 12) peptide (FIG. 9a-c), indicating a permissive role for pro-inflammatory cytokine signals in the accumulation of NKG2C+ cells in a peptide-dependent fashion. In the early culture period, presence of IL-12/18 lead to progressive NK-cell loss independent of peptide recognition, while at later time points, engagement of NKG2C by VMAPRTLFL (SEQ ID NO. 2) rescued cell numbers, resulting in increasing frequencies of NKG2C+ NK cells (FIG. 9d, e, FIG. 10a). In order to gain a quantitative understanding of NKG2C+NK-cell proliferation and accumulation dynamics in this setting, we modified the Gett-Hodgkin model (37) to explicitly take cell division and cell death as well as non-dividing, dying cells into account. Using experimentally determined precursor frequencies (FIG. 10b, c), division times as well as death rates as fitting parameters, the model could describe the data experimentally obtained in the first week of culture, both in the presence (FIG. 9f) and absence of IL-12/18 signaling (FIG. 10d). Without taking varying cell division times and death rates into account, experimental differences in precursor frequencies alone could not explain the observed dynamics of NKG2C+ NK cells (FIG. 10e, f). In the absence of IL-12/18, model analysis revealed shortened division times in the presence of VMAPRTLFL (SEQ ID NO. 2)—compared to VMAPQSLLL (SEQ ID NO. 12)-pulsed targets, while inferred cell death rates were similar (FIG. 10d). Provision of pro-inflammatory cytokines during the initial phase of culture resulted in dramatically accelerated NKG2C+ NK-cell division induced by VMAPRTLFL (SEQ ID NO. 2), while death rates were higher in the presence of VMAPQSLLL (SEQ ID NO. 12) compared to VMAPRTLFL (SEQ ID NO. 2) (FIG. 9f). Thus, mathematical model analysis suggests that the experimentally observed fast proliferation onset and increased absolute NKG2C+ NK-cell numbers in response to VMAPRTLFL (SEQ ID NO. 2)-pulsed targets can be largely explained by accelerated cell division; and presence of IL-12/18 results in slightly decreased cell death upon pulsing with VMAPRTLFL (SEQ ID NO. 2) compared to VMAPQSLLL (SEQ ID NO. 12).

Collectively, these data show that combined recognition of distinct HCMV peptides and pro-inflammatory cytokines control the relative accumulation of NKG2C+ NK cells from HCMV-individuals, potentially contributing to the variable size of the adaptive NKG2C+ NK-cell population observed in healthy HCMV+ individuals.

Example 5: Peptide Recognition and Pro-Inflammatory Cytokines Co-Operate in Guiding the Differentiation of Adaptive NKG2C+ NK Cells Bac Remodeled receptor repertoires and epigenetic landscapes are hallmarks of adaptive NKG2C+ NK cells in HCMV+ individuals (5, 6, 7, 8, 9). Since peptide recognition was required to enable relative accumulation of NKG2C+ NK-cells from HCMV− individuals in the presence of IL-12/18, we examined the individual and combined contributions of the potent VMAPRTLFL (SEQ ID NO. 2) peptide and of pro-inflammatory cytokines to initiate adaptive NK-cell differentiation. While culture with VMAPRTLFL (SEQ ID NO. 2) alone only had mild effects, the combination of VMAPRTLFL (SEQ ID NO. 2) with IL-12/18 skewed expression of several markers including CD2, Siglec-7, educating KIR, Syk, and CD161 preferentially in NKG2C+ cells (FIG. 11a-b, FIG. 12a). Moreover, short stimulation with IL-12/18 played a predominant role in inducing down-regulation of FcεR1γ and CD7 in both NKG2C+ and NKG2C− cells (FIG. 12a, b), while other factors might control NKG2A and DNAM-1 dynamics, since their expression was variable after culture (FIG. 12a, b). Notably, levels of DNA methylation of the IFNG conserved non-coding sequence (CNS1), which is hypomethylated in adaptive NK cells (9, 11), were strikingly reduced after combined treatment with VMAPRTLFL (SEQ ID NO. 2) and IL-12/18 (FIG. 11c, d). Overall, NKG2C engagement co-operated with pro-inflammatory cytokines in guiding the differentiation of NKG2C+ NK cells from HCMV− individuals. As VMAPRTLFL (SEQ ID NO. 2)+IL-12/18 stimulation of NKG2C+ NK cells from HCMV− individuals appeared to most efficiently favor the phenotypic skewing towards adaptive NK cells, we next analyzed the global transcriptional imprinting induced by the combined stimuli. Apart from SIGLEC7, CD7, SYK, and CD2, VMAPRTLFL (SEQ ID NO. 2)+IL-12/18 resulted in consistent transcriptional modulation of several other markers associated with adaptive NK cells including NCR3 (NKp30), SH2DB1 (EAT2) and ZBTB32 (PLZP), while the expression of other adaptive genes such as ZBTB16 (PLZF), ZBTB20, ITGAL or CRTAM was altered only in some individuals (FIG. 11e; FIG. 12c) (5, 7, 38). Functionally, VMAPRTLFL (SEQ ID NO. 2)+IL-12/18 promoted sustained up-regulation of activation and exhaustion markers such as HLA-DR, TNFRSF9 (4-1BB), LAGS, CTLA4, and PDCD1 (PD1) as well as of effector functions including IFNG, TNF, CCL3, CCL4, IL8, CSF2, 110, GZMB, and TNFSF10 (TRAIL) (FIG. 12d), indicating that the combination of these two stimuli promote broad transcriptional imprinting of phenotypic and effector features typical of adaptive NK cells.

Finally, to substantiate the data obtained from in vitro systems, we monitored a cohort of hematopoietic stem cell transplantation (HSCT) patients, which did or did not reactivate HCMV (Table 3). Upon detection of HCMV reactivation, the peptide-encoding UL40 region of the strain causing the acute infection was sequenced. Next, the NK-cell phenotype was comparatively analyzed after resolution of acute infection selectively in patients infected with VMAPRTLFL (SEQ ID NO. 2)- or VMAPRTLIL (SEQ ID NO. 3)-encoding viruses (FIG. 13a). In line with HCMV causing the expansion of NKG2C+ NK cells (39, 40), percentages of NKG2C-expressing CD56dim NK cells were elevated in patients with HCMV reactivation, although this was not consistently impacted by HCMV strains (FIG. 14a, b) and NKG2C+ NK-cell frequencies were dynamic in time among patients infected with both VMAPRTLIL (SEQ ID NO. 3) or VMAPRTLFL (SEQ ID NO. 2) HCMV variants (FIG. 13c). Notably, frequencies of NK cells displaying the adaptive phenotype CD2+ Siglec-7− NKG2A− FcεR1γ− were elevated in NKG2C+ NK cells derived from patients infected with VMAPRTLFL (SEQ ID NO. 2)-encoding viruses (FIG. 14c, FIG. 13b). Conversely, patients infected with VMAPRTLIL (SEQ ID NO. 3) variants displayed varying degrees of adaptive NK-cell differentiation (FIG. 14c, FIG. 13b). Phenotypic alterations were acquired early after HCMV-reactivation within the NKG2C+ compartment and remained relatively stable over time (FIG. 14d), implying that this phenomenon is largely uncoupled from NK-cell maturation after HSCT. Together with the data from in vitro experiments, these findings imply that recognition of distinct UL40-encoded peptides differentially contributes to the accumulation and differentiation of adaptive NKG2C+ NK cells during infection.

In summary, our data provide evidence for sensitive recognition of HCMV-encoded peptides by adaptive NKG2C+ NK cells, which—in co-operation with pro-inflammatory cytokine cues—drives their activation and shapes their population size as well as their phenotypic features in response to HCMV infection. Thus, we propose that the diversity of the NK-cell repertoire among healthy HCMV+ individuals is impacted by the HCMV strain causing the infection.

Discussion of Examples 1-5

HCMV-induced adaptive NKG2C+ NK cells display several features partially recapitulating aspects of T-cell biology, including clonal-like expansion, reprogramming of their recognition repertoire, and global epigenetic remodeling (41). In this study, we propose that expression of NKG2C marks an additional adaptive feature of innate lymphocytes, equipping NKG2C+ NK cells with a germ line-encoded receptor displaying fine peptide specificity and enabling differential recognition of HCMV strains. These findings are even more striking considering our previous identification of CD8+ T cells bearing T-cell receptors (TCR) specific for UL40 peptide/HLA-E complexes, which indicates UL40 as a shared epitope recognized by both NKG2C+ NK cells and CD8+ T cells (42). It seems counterintuitive that HCMV has maintained an activating ligand for NKG2C, despite extensive co-evolution with ist human host. Inversely, UL40-encoded peptides were suggested to serve as an immune evasion strategy by maintaining HLA-E surface expression in the absence of HLA-A/B/C-derived peptides, thus preventing activation of NK cells expressing the cognate inhibitory receptor NKG2A22. Indeed, peptides unable to stabilize HLA-E are rarely encoded by UL40, suggesting that expression of UL40 could be an advantage for the virus. However, our data indicate that the inhibitory function of NKG2A is only subtly tuned by recognition of distinct peptides, unlikely explaining highly polymorphic UL40 sequences. Conversely, UL40 polymorphisms result in NKG2C-mediated responses with different functional avidities: recognition of potent HCMV peptides is sufficient for optimal activation of NKG2C+ NK cells, while peptides with lower potency rely more stringently on co-stimulatory signals. Thus, peptides with lower potency might provide a window of opportunity for the virus to suppress activation of NKG2A+ NK cells and simultaneously allow a certain degree of NKG2C+ NK-cell activation on the host side. Therefore, we propose that immune pressure mediated by adaptive NKG2C+ NK cells could underlie the heterogeneity of UL40 sequences. This immune pressure potentially explains the relative rareness of the VMAPRTLFL (SEQ ID NO. 2) peptide—displaying potent functional avidity for NKG2C—and the high frequency of UL40-encoded peptides with low or intermediate avidity towards NKG2C.

Interestingly, commonly represented HCMV UL40 peptides with low or intermediate avidity toward NKG2C, such as VMAPRTLIL (SEQ ID NO. 3) and VMAPRTLVL (SEQ ID NO. 5), closely resemble self-peptides derived from HLA class I alleles. We envisage that these peptides would not promote expansion and differentiation of adaptive NKG2C+ NK cells at steady state. However, viral mimics with identical sequences might enable activation and differentiation of adaptive NKG2C+ NK cells in the presence of pro-inflammatory signaling and HLA class I down-regulation, which concomitantly occur during HCMV infection. Conversely, the rare UL40-derived VMAPRTLFL (SEQ ID NO. 2) peptide, which is particularly efficient in driving adaptive NKG2C+ NK-cell responses, mimics the signal peptide of HLA-G, the expression of which is restricted to pregnancy and up-regulated in tumors or during inflammation (43). In light of these data, it is conceivable that activation and expansion of adaptive NKG2C+ NK cells from HCMV+ individuals observed during heterologous infections (44, 45) could reflect cross-reactivity of NKG2C towards other viral or even self-peptides in the presence of co-stimulation and inflammatory conditions. Structural analyses of CD94/NKG2 heterodimers have indicated that the C-terminus of peptides presented on HLA-E primarily interacts with CD94 (25, 26, 27). Intriguingly, our data imply that engagement of CD94/NKG2A and CD94/NKG2C by HLA-E/peptide complexes results in strikingly differential and peptide-dependent functional consequences. Although NKG2A and NKG2C display high sequence homology, several amino acids distinct between the two proteins are located in close proximity to the interface with CD94 (25, 26). Accordingly, it was suggested that slight differences in the amino acid sequence between NKG2A and NKG2C could alter the conformation or orientation of the CD94/NKG2 heterodimers (25, 26). Such conformational changes could indirectly affect the recognition of the C-terminal sequence of HLA-E-bound peptides by CD94, resulting in distinct interaction strengths and functional avidities by the two heterodimers.

Despite the pivotal role of NKG2C in activating NK cells during infection and a case report suggesting that NKG2C+ NK cells can control HCMV infection in the absence of T cells in vivo (46), individuals deficient for KLRC2 (encoding NKG2C) lack a clinical phenotype (11, 47). These findings imply the presence of compensatory mechanisms and suggest that NKG2C recognition of HLA-E/UL40 peptide complexes does not represent the only HCMV-derived signal driving adaptive responses of specific NK-cell subsets. Indeed, adaptive NKG2C− NK cells expressing activating KIR have been described in KLRC2-deficient and -sufficient humans (8, 11, 48) and recognition of yet unknown viral ligands by activating KIR or other receptors could result in expansion and differentiation of adaptive cells within the NKG2C-compartment. Supporting this scenario, it was recently reported that selected HCMV strains can modulate HLA-C on infected cells and thereby induce activation of KIR2DS1+ NK cells (49). Similarly, Ly49H-independent NK-cell control of MCMV has been demonstrated in mouse strains other than C57BL/6 (50, 51), reinforcing the concept that NK-cell subsets expressing distinct receptors provide multiple and partially redundant recognition strategies of CMV-infected cells in both humans and mice. Generation of murine adaptive Ly49H+ NK cells requires cross-linking of Ly49H (12,13, 52) and is enhanced by DNAM-1 co-stimulation53. Furthermore, IL-12 is essential for the expansion and protective function of virus-specific Ly49H+ NK cells (36). Our data indicate that pro-inflammatory signaling via IL-12/18, which was shown to generate memory-like NK-cell properties independent of CMV infection (54, 55), results in fundamental phenotypic and functional changes and initiates adaptive NK-cell differentiation. However, provision of IL-12/18 is not sufficient to expand NKG2C+ NK cells form HCMV− individuals and induces sustained activation-induced cell death. When exposed to IL-12/18, the strength of peptide recognition by NKG2C correlated with the numerical and relative expansion of NKG2C+ NK cells, implying that the quality of peptide recognition contributes to configure variable pools of differentiated adaptive NK cells in infected individuals.

In conclusion, our data reveal an exquisite mechanism of specific innate recognition of HCMV-infected cells as a novel adaptive property of NKG2C+ NK cells. By recognizing variable UL40-encoded peptides, NKG2C can contribute to dynamic shifts in the NK-cell compartment, favoring the expansion and differentiation of adaptive subsets based on the strength of peptide recognition. On the pathogen side, variability in the UL40 peptide repertoire can be regarded as an adaptation attempt of HCMV to modulate host responses. Together, peptide recognition by NKG2C and sequence variants of UL40-derived peptides further expose the well-adapted host-pathogen interaction between NK cells and HCMV.

Example 6: Induction of a Protective Anti-Tumor Response

The HCMV peptide VMAPRTLFL is also found in the leader sequence of HLA-G (Llano et al., 1998; European journal of immunology 28, 2854-2863), another non-classical MHC class I molecule which is not expressed in most healthy tissues but frequently upregulated by tumors (Curigliano et al. 2013; Clin Cancer Res. 2013; 19(20):5564-71). HLA-G inhibits immune cells by directly binding to inhibitory receptors of the LIR-family, such as LILRB1, which allows tumor cells to evade immune recognition. On the other hand, VMAPRTLFL (SEQ ID NO. 2) is cleaved off the signal sequence of HLA-G and presented an HLA-E (Llano et al., 1998; European journal of immunology 28, 2854-2863), making HLA-G/HLA-E coexpressing tumors potentially susceptible to recognition by NKG2C+ NK cells.

Indeed, we could demonstrate this effect using a cell line transfected with HLA-G. Compared to the untransfected control, HLA-G-expressing cells specifically activated NKG2C+ NK cells, even in the context of low HLA-E expression (FIG. 15a-b, FIG. 16). The activation was blocked by an antibody against CD94 (FIG. 15c), demonstrating its role in recognition. These data demonstrate the reactivity of NKG2C+ NK cells against HLA G expressing targets. Since in this system HLA-G is extrinsically over-expressed to very high levels and the endogenous expression of HLA-E is low (Supp. FIG. 1), we assessed the activation under blockade of the inhibitory HLA-G receptor LILRB1. The blockade further increased the activation, arguing that the in vivo NK cell response might be even more pronounced, as endogenous expression of HLA-G will not be that much higher than of HLA-E and therefore the inhibitory signal through LILRB1 will be less dominant. Based on these findings, we propose the in vivo expansion of NKG2C+ NK cells as an immunotherapy to treat HLA-G/HLA-E co-expressing tumors.

To identify patients suitable for these treatment strategies, tumor biopsies or circulating tumor cells can be tested for HLA-G and HLA-E expression by flow cytometry or by RT-PCR. Isolated tumor cells from biopsies can also be directly tested for susceptibility to lysis by NKG2C+ adaptive NK cells in in vitro cytotoxicity assays using adaptive NKG2C+ NK cells. Our approach of NKG2C+ NK cell expansion might be especially valuable for patients receiving HSCT for the treatment of leukemia. In contrast to adaptive cell types targeted by classical vaccines, NK cells are among the first lymphocyte populations to recover after transplantation and therefore can be targeted early using our approach, thus potentially protecting against HCMV reactivation and tumor relapse. Secondly, an interesting correlation of reduced relapse rates in patients reactivating HCMV and presenting with adaptive NK cell expansions points towards an anti-leukemic effect of adaptive NK cells (Elmagaacli et al., Blood. 2011; 118(5):1402-12; Cichocki et al. Leukemia. 2016; 30(2):456-63.) Therefore, our approach might be of dual advantage for these patients, combining protective effects against HCMV with an enhanced graft-versus-leukemia response.

Tables

TABLE 2

Abundance of peptide identified peptide sequences in clinical isolates.

| SEQ ID NO | Identified Peptide Sequence | Number of clinical Isolates |
| --- | --- | --- |
| 3 | VMAPRTLIL | 88 |
| 4 | VMAPRTLLL | 35 |
| 5 | VMAPRTLVL | 27 |
| 6 | VMAPRSLLL | 7 |
| 7 | VMAPRSLIL | 6 |
| 8 | VMTPRTLVL | 6 |
| 2 | VMAPRTLFL | 3 |
| 9 | VMAPRILIL | 3 |
| 10 | AMAPRTLIL | 3 |
| 11 | VIAPRTLVL | 2 |
| 12 | VMAPQSLLL | 2 |
| 13 | VMAPRTFVL | 2 |
| 14 | VMTPRTLIL | 2 |
| 15 | VTAPRTLIL | 2 |
| 16 | VTAPRTLLL | 2 |
| 17 | VMAPWTLLL | 2 |
| 18 | VMVPRSLIL | 1 |
| 19 | AMAPRTLVL | 1 |
| 20 | VIAPRTLIL | 1 |
| 21 | VIAPRTLLL | 1 |

TABLE 2-continued

Abundance of peptide identified peptide sequences in clinical isolates.

| SEQ ID NO | Identified Peptide Sequence | Number of clinical Isolates |
|---|---|---|
| 22 | VLAPRTLIL | 1 |
| 23 | VMALRTLIL | 1 |
| 24 | VMAPRGLIL | 1 |
| 25 | VMAPRNLIL | 1 |
| 26 | VMAPRTLFV | 1 |
| 27 | VMAPRTLLM | 1 |
| 28 | VMAPRTLVM | 1 |
| 29 | VMAPRTSLL | 1 |
| 30 | VMAPRTSVL | 1 |
| 31 | VMAPWTLIL | 1 |
| 32 | VMAPWTLVL | 1 |
| 33 | VMDPRTLLL | 1 |
| 34 | VMGPRTLIL | 1 |
| 35 | VMGPRTLLL | 1 |
| 36 | VMVPQTLIL | 1 |
| 37 | VMVPRTLLL | 1 |
| 38 | VTAPRTLVL | 1 |
| 39 | VVAPRTLIL | 1 |
| 40 | VVAPRTLLL | 1 |
| 41 | VMVPRTLIL | 1 |
| 42 | VMATRTLLL | 1 |
|  | TOTAL | 217 |

TABLE 3

Patient Characteristics

| Patient ID | Age | Gender | Diagnosis | Conditioning | Graft type | GvHD prophylaxis | HCMV serostatus (pre Tx) | HCMV reactivation [days post Tx] (detection method) | UL40 peptide sequence | Phenotype analysis [days post Tx] | % CD56<sup>bright</sup> of CD3<sup>-</sup>CD56<sup>+</sup> | % NKG2A<sup>+</sup> of CD56<sup>dim</sup> | % NKG2C<sup>+</sup> of CD56<sup>dim</sup> | %CD2<sup>+</sup>NKG2A<sup>-</sup>Siglec-7<sup>-</sup>FcεRIγ<sup>-</sup> of |
|---|---|---|---|---|---|---|---|---|---|---|---|---|---|---|
| 1636 | 69 | Male | AML | BCNU/Flu/Mel | 10/10 | ATG/CsA/MMF | Negative | Not detected | N/A | 180 | 7.59 | 45.1 | 7.26 | 0.57 |
| 1555 | 66 | Female | AML | FLAMSA/Bu/Cy | 9/10 | ATG/CsA/MMF | Negative | Not detected | N/A | 180 | 18.9 | 73.7 | 10.3 | 1.33 |
| 1637 | 62 | Male | AML | BCNU/Flu/Mel | 10/10 | ATG/CsA/MMF | Negative | Not detected | N/A | 180 | 3.88 | 36.5 | 9.32 | 0.30 |
| 1642 | 39 | Male | Hodgkin | Cy/Flu/TBI | Mismatched sibling | Cyclo/CsA/MMF | Negative | Not detected | N/A | 60 | 29.7 | 88.9 | 10.8 | 0.90 |
| 1553 | 30 | Female | CML | Bu/Cy | 10/10 | ATG/CsA/MTX | Negative | Not detected | N/A | 60 | 38.6 | 69.6 | 6.05 | 0.76 |
| #018 | 58 | Female | AML | Bu/Flu/ATG | 10/10 sibling | CsA/MMF | Negative | Not detected | N/A | 35 | 45.0 | 81.2 | 8.56 | 0.00 |
| #050 | 52 | Male | AML | TBI/Flu/Cy/ATG | 10/10 | CsA/MMF | Negative | Not detected | N/A | 119 | 72.9 | 94.1 | 9.73 | 0.67 |
| #063 | 71 | Male | AML | TBI/Flu/Cy/ATG | 9/10 | CsA/MMF | Negative | Not detected | N/A | 35 | 42.5 | 91.0 | 3.97 | 7.16 |
| #071 | 60 | Male | AML | Bu/Flu/ATG | 10/10 sibling | CsA/MMF | Negative | Not detected | N/A | 153 | 29.7 | 88.9 | 8.49 | 2.75 |
| #078 | 72 | Male | AML | TBI/Flu/ATG | 10/10 | CsA/MMF | Negative | Not detected | N/A | 101 | 57.3 | 56.5 | 7.05 | 0.77 |
| 1553 | 33 | Female | AML | FLAMSA-Bu | 9/10 | ATG/CsA/MMF | Positive | 30-60 (pp65) | VMAPRTLIL | 120 | 5.44 | 33.7 | 38.7 | 5.49 |
| 1606 | 40 | Female | CML | Bu/Cy | 10/10 | ATG/CsA/MMF | Positive | 60 (pp65) | VMAPRTLIL | 180 | 27.1 | 41.6 | 37.9 | 9.89 |
| 1628 | 56 | Male | MDS | FLAMSA/Bu | 9/10 | ATG/CsA/MMF | Positive | 120 (pp65) | VMAPRTLIL | 180 | 5.41 | 27 | 25.1 | 22.4 |
| 1630 | 70 | Female | AML | BCNU/Flu/Mel | 10/10 | ATG/CsA/MMF | Positive | 60 (pp65) | VMAPRTLIL | 180 | 18.6 | 81.4 | 21.2 | 33.2 |
| 1640 | 29 | Male | AML | Thio/Bu/Flu TBI/Cy/ | Mismatched sibling | Cyclo/CsA/MMF | Positive | 30 (pp65) | VMAPRTLIL | 180 | 19.6 | 74.0 | 24.8 | 14.4 |

TABLE 3-continued

Patient Characteristics

| Patient ID | Age | Gender | Diagnosis | Conditioning | Graft type | GvHD prophylaxis | HCMV serostatus (pre Tx) | HCMV reactivation [days post Tx] (detection method) | UL40 peptide sequence | Phenotype analysis [days post Tx] | % CD56$^{bright}$ of CD3$^-$CD56$^+$ | % NKG2A$^+$ of CD56$^{dim}$ | % NKG2C$^+$ of CD56$^{dim}$ | %CD2$^+$ NKG2A$^-$ Siglec-7$^-$ FcεRIg$^-$ of |
|---|---|---|---|---|---|---|---|---|---|---|---|---|---|---|
| #074 | 53 | Female | AML | ATG | 10/10 | CsA/MTX | Positive | 12 (viremia) | VMAPRTLIL | 105 | 13.7 | 79.4 | 17.5 | 3.25 |
| #033 | 21 | Male | ALL | TBI/Cy/ATG | 9/10 | CsA/MTX | Positive | 25 (viremia) | VMAPRTLIL | 53 | 31.6 | 85.5 | 10.8 | 0.36 |
| #069 | 65 | Female | AML | Bu/Flu/ATG | 10/10 | CsA/MTX | Positive | 31 (viremia) | VMAPRTLIL | 46 | 13.9 | 87.9 | 9.10 | 2.86 |
| #008 | 43 | Male | AML | TBI/Cy/ATG | 10/10 | CsA/MTX | Positive | 12 (viremia) | VMAPRTLIL | 55 | 13.9 | 91.2 | 8.61 | 2.66 |
| #23 | 52 | Female | AML | Bu/Flu/ATG | 9/19 | CsA/MMF | Positive | 12 (viremia) | VMAPRTLIL | 215 | 9.31 | 53.1 | 10.8 | 9.74 |
| #087 | 58 | Male | AML | Bu/Flu/ATG | 10/10 | CsA/MMF | Positive | 27 (viremia) | VMAPRTLFL | 190 | 11.4 | 26.4 | 49.9 | 46.9 |
| #075 | 60 | Male | MDS | Bu/Flu/ATG | 10/10 | CsA/MMF + Basiliximab | Positive | 104 (viremia) | VMAPRTLFL | 278 | 17.8 | 78.6 | 15.3 | 35.2 |

TABLE 4

Antibodies Used for Flow Cytometry and Functional Assays.

| Antibody | Supplier | Catalogue number |
| --- | --- | --- |
| CD14 BV510 (clone: M5E2) | BioLegend | Cat#301842 |
| CD19 BV510 (clone: HIB19) | BioLegend | Cat#302242 |
| CD2 PerCP-Cy5.5 (clone: RPA-2.10) | BioLegend | Cat#300216 |
| CD3 PE-Cy5 (clone: UCHT1) | BioLegend | Cat#300410 |
| CD56 PE-Dazzle594 (clone: HCD56) | BioLegend | Cat#318348 |
| CD57 Pacific Blue (clone: HCD57) | BioLegend | Cat#322316 |
| HLA class I Pacific Blue (clone: W6/32) | BioLegend | Cat#311418 |
| IgM BV605 (clone: RMM-1) | BioLegend | Cat#406523 |
| KIR3DL1 Alexa700 (clone: DX9) | BioLegend | Cat#312712 |
| KIR3DL1 PerCP-Cy5.5 (clone: DX9) | BioLegend | Cat#312718 |
| LFA-3 PE (clone: TS2/9) | BioLegend | Cat#330905 |
| LFA-3 Purified (clone: TS2/9) | BioLegend | Cat#330912 |
| Streptavidin BV785 | BioLegend | Cat#405249 |
| TNF BV605 (clone: Mab11) | BioLegend | Cat#502936 |
| CD7 FITC (clone: CD7-6B7) | BioLegend | Cat#982704 |
| CD161 BV785 (clone: HP-3G10) | BioLegend) | Cat#339930 |
| CD3 Cy5 (clone: UCHT1) | In house | N/A |
| FcεR1γ FITC (rabbit polyclonal) | Merck Millipore | Cat#FCABS400F |
| HCMV-IE Alexa488 (clone: 8B1.2) | Merck Millipore | Cat#MAB810X |
| DNAM-1 PE-Vio770 (clone: DX11) | Miltenyi | Cat#130-099-966 |
| CCL3 APC (clone: REA254) | Miltenyi Biotec | Catv130-103-630 |
| HLA-E PE (clone: 3D12) | Miltenyi Biotec | Cat#130-096-849 |
| IFN-γ PE-Vio770 (clone: 45-15) | Miltenyi Biotec | Cat#130-096-752 |
| KIR2DL1 APC (clone: REA284) | Miltenyi Biotec | Cat#130-103-935 |
| KIR2DL1 APC-Vio770 (clone: REA284) | Miltenyi Biotec | Cat#130-103-937 |
| KIR2DL3 FITC (clone: REA147) | Miltenyi Biotec | Cat#130-100-125 |
| NKG2A Biotin (clone: REA110) | Miltenyi Biotec | Cat#130-098-819 |
| NKG2A PE-Vio770 (REA110) | Miltenyi Biotec | Cat#130-105-647 |
| NKG2C PE (clone: REA205) | Miltenyi Biotec | Cat#130-103-635 |
| Siglec-7 APC-Vio770 (clone: REA214) | Miltenyi Biotec | Cat#130-101-009 |
| Siglec-7 PE-Vio700 (clone: REA214) | Miltenyi Biotec | Cat#130-100-975 |
| KIR2DL2/2DS2/2DL3 Alexa700 (clone: GL183) | A. Morretta (in house conjugated) | N/A |
| CD94 unconjugated (clone: #131412) | RnD Systems | Cat#MAB1058 |
| IgG1 isotype control unconjugated (clone: #11711) | RnD Systems | Cat#MAB002 |
| CD107a Alexa488 (clone: H3A4) | ThermoFisher | Cat#65-0865-18 |
| CD57 unconjugated (clone: TBO1) | ThermoFisher | Cat#16-0577-85 |
| Syk APC (clone: 4D10.1) | ThermoFisher | Cat#17-6696-42 |

TABLE 5

Primer sequences used for nested PCR, RT-qPCR and DNA methylation analysis.

| Primer Name | SEQ ID No. | Primer Sequence |
| --- | --- | --- |
| UL40_forward | 43 | 5'-GGCTCTGTCTCGTCGTCATT-3' |
| UL40_reverse | 44 | 5'-TAAGGGCACTCGTGAGGATG-3' |
| UL40_nested_forward | 45 | 5'-CAACAGTCGGCAGAATGAAC-3' |
| UL40_nested_reverse | 46 | 5'-CTGGAACACGAGCGGACATA-3' |
| hGAPDH_forward | 47 | 5'-TTCGTCATGGGTGTGAACCA-3' |
| hGAPDH_reverse | 48 | 5'-GGACTGTGGTCATGAGTCCTT-3' |
| IFNG_CNS1_forward | 49 | 5'-TCTTTCCCTACACGACGCTCTTCCGATCATGAGTTAATATTGGATTTATGTTTTT-3' |
| IFNG_CNS1_reverse | 50 | 5'-GTGACTGGAGTTCAGACGTGTGCTCTTCCGATCTATATAAATAACATACCTTCTATATTCTTT-3' |
| NGS_forward | 51 | 5-CAAGCAGAAGACGGCATACGAGAT<u>XXXXXX</u>GTGACTGGAGTTCAGACGTGTGCTCTTCCGATCT-3' |
| NGS_reverse | 52 | 5'-AATGATACGGCGACCACCGAGATCTACAC<u>XXXXXX</u>TCTTTCCCTACACGACGCTCTTCCGATC-3' |

IFNG CNS1-specific oligos were designed to have a region-specific 3' part (bold) and a Next generation sequencing (NGS)-compatible 5' tag. NGS oligos were employed to introduce unique DNA barcodes (marked as X) to individual samples.

TABLE 6

Primer Sequences Used for HCMV Mutagenesis.

| Primer Name | SEQ ID No. | Primer Sequence |
| --- | --- | --- |
| US2-lox-tet.for | 53 | 5'-GATCACATCCCCTTGCAGTACCAGACGCAGGGCTATAACTTCGTATAATGTATGCTATACGAAGTTATGGCTGGTTTATGCATATCG-3' |
| G-lox-tet.rev | 54 | 5'-TGCATGCCATGGTACCCGGGAGCTCGAATTCGAAGCTTCTTTCCCTTTGTCAACAGCAA-3' |
| pIC1.for | 55 | 5'-CTAGCAGATCTGCAGGGACGCATCGTGGCCGGAT-3' |
| MC-Cre.rev | 56 | 5'-TAAGGATGCATGTTTAAACGTGACCACGTCGTGGAATGC-3' |
| KnR-ISce.for | 57 | 5'-GTGGTCACGTTTAAACATGCATCCTTAATTAAGGCTGCGATCTATCGAGTTTTCCCAGTCACGACG-3' |
| pIC.rev | 58 | 5'-TAGGAAGCTTGATATCGAACAAACGACCCAACACC-3' |
| loxPUS2.for | 59 | 5'-GCCAGATCACATCCCCTTGCAGTACCAGACGCAGGGCTAGGACGGTATCGATAAGCTGGAT-3' |
| KanRITyellow.rev | 60 | 5'-TGCATGCCATGGTACCCGGGAGCTCGAATTCGAAGCTTCTGACGCATCGTGGCCGGATCTC-3' |
| UL40_VMAPRTLIL.for | 61 | 5'-ACAGGAGTCCAAGCGTCAGAATTAAAGTCCGCGGAGCCATAACCGCGCAAGTGAAGCCGACGCATCGTGGCCGGAT-3' |
| UL40_VMAPRTLIL.rev | 62 | 5'-AAATTCAGCAACACTCGTATCGGCTTCACTTGCGCGGTTATGGCTCCGCGGACTTTAATGGTGACCACGTCGTGGA-3' |
| UL40_VMAPRTLFL.for | 63 | 5'-TCCTCATACACAGGAGTCCAAGCGTCAGAAATAAAGTCCGCGGAGCCATAACCGCGCAAGGACGCATCGTGGCCGGAT-3' |
| UL40_VMAPRTLFL.rev | 64 | 5'-AACACTCGTATCGGCTTCACTTGCGCGGTTATGGCTCCGCGGACTTTATTTCTGACGCTTTGGTGACCACGTCGTGGA-3' |
| UL40_VMAPQSLLL.for | 65 | 5'-TCCTCATACACAGGAGTCCAAGCGTCAGAAGTAAACTCTGCGGAGCCATAACCGCGCAAGGACGCATCGTGGCCGGAT-3' |
| UL40_VMAPQSLLL.rev | 66 | 5'-AACACTCGTATCGGCTTCACTTGCGCGGTTATGGCTCCGCAGAGTTTACTTCTGACGCTTTGGTGACCACGTCGTGGA-3' |

REFERENCES

1. Vivier, E., Tomasello, E., Baratin, M., Walzer, T. & Ugolini, S. Functions of natural killer cells. Nature immunology 9, 503-510 (2008).
2. Biron, C. A., Byron, K. S. & Sullivan, J. L. Severe herpesvirus infections in an adolescent without natural killer cells. The New England journal of medicine 320, 1731-1735 (1989).
3. O'Sullivan, T. E., Sun, J. C. & Lanier, L. L. Natural Killer Cell Memory. Immunity 43, 634-645 (2015).
4. Jackson, S. E., Mason, G. M. & Wills, M. R. Human cytomegalovirus immunity and immune evasion. Virus Res 157, 151-160 (2011).
5. Guma, M. et al. Imprint of human cytomegalovirus infection on the NK cell receptor repertoire. Blood 104, 3664-3671 (2004).
6. Beziat, V. et al. CMV drives clonal expansion of NKG2C+ NK cells expressing self-specific KIRs in chronic hepatitis patients. European journal of immunology 42, 447-457 (2012).
7. Schlums, H. et al. Cytomegalovirus infection drives adaptive epigenetic diversification of NK cells with altered signaling and effector function. Immunity 42, 443-456 (2015).
8. Beziat, V. et al. NK cell responses to cytomegalovirus infection lead to stable imprints in the human KIR repertoire and involve activating KIRs. Blood 121, 2678-2688 (2013).
9. Luetke-Eversloh, M. et al. Human cytomegalovirus drives epigenetic imprinting of the IFNG locus in NKG2Chi natural killer cells. PLoS pathogens 10, e1004441 (2014).
10. Lee, J. et al. Epigenetic modification and antibody-dependent expansion of memory-like NK cells in human cytomegalovirus-infected individuals. Immunity 42, 431-442 (2015).
11. Liu, L. L. et al. Critical Role of CD2 Co-stimulation in Adaptive Natural Killer Cell Responses Revealed in NKG2C-Deficient Humans. Cell reports 15, 1088-1099 (2016).
12. Arase, H., Mocarski, E. S., Campbell, A. E., Hill, A. B. & Lanier, L. L. Direct recognition of cytomegalovirus by activating and inhibitory NK cell receptors. Science 296, 1323-1326 (2002).
13. Smith, H. R. et al. Recognition of a virus-encoded ligand by a natural killer cell activation receptor. Proceedings of the National Academy of Sciences of the United States of America 99, 8826-8831 (2002).
14. Braud, V. M. et al. HLA-E binds to natural killer cell receptors CD94/NKG2A, B and C. Nature 391, 795-799 (1998).
15. Lee, N. et al. HLA-E is a major ligand for the natural killer inhibitory receptor CD94/NKG2A. Proceedings of the National Academy of Sciences of the United States of America 95, 5199-5204 (1998).
16. Brooks, A. G. et al. Specific recognition of HLA-E, but not classical, HLA class I molecules by soluble CD94/NKG2A and NK cells. Journal of immunology 162, 305-313 (1999).
17. Guma, M. et al. Expansion of CD94/NKG2C+ NK cells in response to human cytomegalovirus-infected fibroblasts. Blood 107, 3624-3631 (2006).
18. Rolle, A. et al. IL-12-producing monocytes and HLA-E control HCMV-driven NKG2C+ NK cell expansion. The Journal of clinical investigation 124, 5305-5316 (2014).

19. Braud, V., Jones, E. Y. & McMichael, A. The human major histocompatibility complex class 1b molecule HLA-E binds signal sequence-derived peptides with primary anchor residues at positions 2 and 9. European journal of immunology 27, 1164-1169 (1997).
20. Michaelsson, J. et al. A signal peptide derived from hsp60 binds HLA-E and interferes with CD94/NKG2A recognition. The Journal of experimental medicine 196, 1403-1414 (2002).
21. Ulbrecht, M. et al. Cutting edge: the human cytomegalovirus UL40 gene product contains a ligand for HLA-E and prevents NK cell-mediated lysis. Journal of immunology 164, 5019-5022 (2000).
22. Tomasec, P. et al. Surface expression of HLA-E, an inhibitor of natural killer cells, enhanced by human cytomegalovirus gpUL40. Science 287, 1031 (2000).
23. Cerboni, C. et al. Synergistic effect of IFN-gamma and human cytomegalovirus protein UL40 in the HLA-E-dependent protection from NK cell-mediated cytotoxicity. European journal of immunology 31, 2926-2935 (2001).
24. Wang, E. C. et al. UL40-mediated NK evasion during productive infection with human cytomegalovirus. Proceedings of the National Academy of Sciences of the United States of America 99, 7570-7575 (2002).
25. Sullivan, L. C. et al. The heterodimeric assembly of the CD94-NKG2 receptor family and implications for human leukocyte antigen-E recognition. Immunity 27, 900-911 (2007).
26. Kaiser, B. K., Pizarro, J. C., Kerns, J. & Strong, R. K. Structural basis for NKG2A/CD94 recognition of HLA-E. Proceedings of the National Academy of Sciences of the United States of America 105, 6696-6701 (2008).
27. Petrie, E. J. et al. CD94-NKG2A recognition of human leukocyte antigen (HLA)-E bound to an HLA class I leader sequence. The Journal of experimental medicine 205, 725-735 (2008).
28. Llano, M. et al. HLA-E-bound peptides influence recognition by inhibitory and triggering CD94/NKG2 receptors: preferential response to an HLA-G-derived nonamer. European journal of immunology 28, 2854-2863 (1998).
29. Vales-Gomez, M., Reyburn, H. T., Erskine, R. A., Lopez-Botet, M. & Strominger, J. L. Kinetics and peptide dependency of the binding of the inhibitory NK receptor CD94/NKG2-A and the activating receptor CD94/NKG2-C to HLA-E. The EMBO journal 18, 4250-4260 (1999).
30. Heatley, S. L. et al. Polymorphism in human cytomegalovirus UL40 impacts on recognition of human leukocyte antigen-E (HLA-E) by natural killer cells. The Journal of biological chemistry 288, 8679-8690 (2013).
31. Garrigue, I. et al. Variability of UL18, UL40, UL111a and US3 immunomodulatory genes among human cytomegalovirus clinical isolates from renal transplant recipients. J Clin Virol 40, 120-128 (2007).
32. Andreatta, M. & Nielsen, M. Gapped sequence alignment using artificial neural networks: application to the MHC class I system. Bioinformatics 32, 511-517 (2016).
33. Djaoud, Z. et al. Cytomegalovirus-Infected Primary Endothelial Cells Trigger NKG2C+ Natural Killer Cells. Journal of innate immunity 8, 374-385 (2016).
34. Garcia-Sastre, A. & Biron, C. A. Type 1 interferons and the virus-host relationship: a lesson in detente. Science 312, 879-882 (2006).
35. van de Berg, P. J. et al. Human cytomegalovirus induces systemic immune activation characterized by a type 1 cytokine signature. The Journal of infectious diseases 202, 690-699 (2010).
36. Sun, J. C. et al. Proinflammatory cytokine signaling required for the generation of natural killer cell memory. The Journal of experimental medicine 209, 947-954 (2012).
37. Gett, A. V. & Hodgkin, P. D. A cellular calculus for signal integration by T cells. Nature immunology 1, 239-244 (2000).
38. Beaulieu, A. M., Zawislak, C. L., Nakayama, T. & Sun, J. C. The transcription factor Zbtb32 controls the proliferative burst of virus-specific natural killer cells responding to infection. Nature immunology 15, 546-553 (2014).
39. Foley, B. et al. Cytomegalovirus reactivation after allogeneic transplantation promotes a lasting increase in educated NKG2C+ natural killer cells with potent function. Blood 119, 2665-2674 (2012).
40. Lopez-Verges, S. et al. Expansion of a unique CD57(+) NKG2Chi natural killer cell subset during acute human cytomegalovirus infection. Proceedings of the National Academy of Sciences of the United States of America 108, 14725-14732 (2011).
41. Hammer, Q. & Romagnani, C. About Training and Memory: NK-Cell Adaptation to Viral Infections. Advances in immunology 133, 171-207 (2017).
42. Pietra, G. et al. HLA-E-restricted recognition of cytomegalovirus-derived peptides by human CD8+ cytolytic T lymphocytes. Proceedings of the National Academy of Sciences of the United States of America 100, 10896-10901 (2003).
43. Carosella, E. D., Moreau, P., Lemaoult, J. & Rouas-Freiss, N. HLA-G: from biology to clinical benefits. Trends in immunology 29, 125-132 (2008).
44. Bjorkstrom, N. K. et al. Rapid expansion and long-term persistence of elevated NK cell numbers in humans infected with hantavirus. The Journal of experimental medicine 208, 13-21 (2011).
45. Petitdemange, C. et al. Unconventional repertoire profile is imprinted during acute chikungunya infection for natural killer cells polarization toward cytotoxicity. PLoS pathogens 7, e1002268 (2011).
46. Kuijpers, T. W. et al. Human NK cells can control CMV infection in the absence of T cells. Blood 112, 914-915 (2008).
47. Goodier, M. R. et al. Rapid NK cell differentiation in a population with near-universal human cytomegalovirus infection is attenuated by NKG2C deletions. Blood 124, 2213-2222 (2014).
48. Della Chiesa, M. et al. Human cytomegalovirus infection promotes rapid maturation of NK cells expressing activating killer Ig-like receptor in patients transplanted with NKG2C−/− umbilical cord blood. Journal of immunology 192, 1471-1479 (2014).
49. van der Ploeg, K. et al. Modulation of Human Leukocyte Antigen-C by Human Cytomegalovirus Stimulates KIR2DS1 Recognition by Natural Killer Cells. Frontiers in immunology 8 (2017).
50. Adam, S. G. et al. Cmv4, a new locus linked to the NK cell gene complex, controls innate resistance to cytomegalovirus in wild-derived mice. Journal of immunology 176, 5478-5485 (2006).
51. Kielczewska, A. et al. Ly49P recognition of cytomegalovirus-infected cells expressing H2-Dk and CMV-encoded m04 correlates with the NK cell antiviral response. The Journal of experimental medicine 206, 515-523 (2009).
52. Sun, J. C., Beilke, J. N. & Lanier, L. L. Adaptive immune features of natural killer cells. Nature 457, 557-561 (2009).

53. Nabekura, T. et al. Costimulatory molecule DNAM-1 is essential for optimal differentiation of memory natural killer cells during mouse cytomegalovirus infection. Immunity 40, 225-234 (2014).
54. Cooper, M. A. et al. Cytokine-induced memory-like natural killer cells. Proceedings of the National Academy of Sciences of the United States of America 106, 1915-1919 (2009).
55. Romee, R. et al. Cytokine activation induces human memory-like NK cells. Blood 120, 4751-4760 (2012).
56. Hammer, Q. & Romagnani, C. OMIP-039: Detection and analysis of human adaptive NKG2C+ natural killer cells. Cytometry A (2017).
57. Ravens, S. et al. Human gammadelta T cells are quickly reconstituted after stem-cell transplantation and show adaptive clonal expansion in response to viral infection. Nat. Immunol. 18, 393-401 (2017).
58. Borrego, F., Ulbrecht, M., Weiss, E. H., Coligan, J. E. & Brooks, A. G. Recognition of human histocompatibility leukocyte antigen (HLA)-E complexed with HLA class I signal sequence-derived peptides by CD94/NKG2 confers protection from natural killer cell-mediated lysis. J. Exp. Med. 187, 813-818 (1998).
59. Crooks, G. E., Hon, G., Chandonia, J. M. & Brenner, S. E. WebLogo: a sequence logo generator. Genome Res. 14, 1188-1190 (2004).
60. Roederer, M. Interpretation of cellular proliferation data: avoid the panglossian. Cytometry A 79, 95-101 (2011).
61. Cossarizza, A. et al. Guidelines for the use of flow cytometry and cell sorting in immunological studies. Eur. J. Immunol. 47, 1584-1797 (2017).
62. Roederer, M., Nozzi, J. L. & Nason, M. C. SPICE: exploration and analysis of post-cytometric complex multivariate datasets. Cytometry A 79, 167-174 (2011).
63. Sinzger, C. et al. Cloning and sequencing of a highly productive, endotheliotropic virus strain derived from human cytomegalovirus TB40/E. J. Gen. Virol. 89, 359-368 (2008).
64. Borst, E. M., Hahn, G., Koszinowski, U. H. & Messerle, M. Cloning of the human cytomegalovirus (HCMV) genome as an infectious bacterial artificial chromosome in *Escherichia coli*: a new approach for construction of HCMV mutants. J. Virol. 73, 8320-8329 (1999).
65. Hobom, U., Brune, W., Messerle, M., Hahn, G. & Koszinowski, U. H. Fast screening procedures for random transposon libraries of cloned herpesvirus genomes: mutational analysis of human cytomegalovirus envelope glycoprotein genes. J. Virol. 74, 7720-7729 (2000).
66. Tischer, B. K., Smith, G. A. & Osterrieder, N. En passant mutagenesis: a two step markerless red recombination system. Methods Mol. Biol. 634, 421-430 (2010).
67. Smith, G. A. & Enquist, L. W. A self-recombining bacterial artificial chromosome and its application for analysis of herpesvirus pathogenesis. Proc. Natl. Acad. Sci. U.S.A 97, 4873-4878 (2000).
68. Crnkovic-Mertens, I. et al. Virus attenuation after deletion of the cytomegalovirus Fc receptor gene is not due to antibody control. J. Virol. 72, 1377-1382 (1998).
69. Gibson, D. G. et al. Enzymatic assembly of DNA molecules up to several hundred kilobases. Nat Methods 6, 343-345 (2009).
70. Elbasani, E., Gabaev, I., Steinbruck, L., Messerle, M. & Borst, E. M. Analysis of essential viral gene functions after highly efficient adenofection of cells with cloned human cytomegalovirus genomes. Viruses 6, 354-370 (2014).
71. De Boer, R. J., Ganusov, V. V., Milutinovic, D., Hodgkin, P. D. & Perelson, A. S. Estimating lymphocyte division and death rates from CFSE data. Bull. Math. Biol. 68, 1011-1031 (2006).
72. Kim, D. et al. TopHat2: accurate alignment of transcriptomes in the presence of insertions, deletions and gene fusions. Genome Biol. 14, R36 (2013).
73. Langmead, B. & Salzberg, S. L. Fast gapped-read alignment with Bowtie 2. Nat Methods 9, 357-359 (2012).
74. Liao, Y., Smyth, G. K. & Shi, W. featureCounts: an efficient general purpose program for assigning sequence reads to genomic features. Bioinformatics 30, 923-930 (2014).
75. Love, M. I., Huber, W. & Anders, S. Moderated estimation of fold change and dispersion for RNA-seq data with DESeq2. Genome Biol. 15, 550 (2014).

---

What is claimed is:

1. A method of treating a subject having or being at risk of developing a medical condition associated with pathogenic cells expressing HLA-E and a peptide comprising an amino acid sequence according to SEQ ID NO: 1 or SEQ ID NO: 2, the method comprising administering to said subject an effective amount of an isolated peptide of 9 to 30 amino acids comprising an amino acid sequence according to SEQ ID NO:2 (VMAPRTLFL), wherein the method expands and/or activates NKG2C+ natural killer (NK) cells, wherein the medical condition is a cancer associated with expression of HLA-G and HLA-E, wherein the cancer is identified by:
   a) providing a sample comprising cancer cells from the subject, and
   b) determining expression of HLA-G and HLA-E in said sample.

2. The method according to claim 1, wherein the expression of HLA-G and HLA-E is above levels in healthy control cells.

3. The method according to claim 1, wherein the cancer is selected from the group consisting of leukemia, Melanoma, choriocarcinoma, breast cancer, endometrial cancer, ovarian cancer, cervical cancer, esophageal squamous cell carcinoma, colorectal cancer, gastric cancer, hepatocellular carcinoma, glioblastoma, lung cancer, nasopharyngeal carcinoma, pancreatic adenocarcinoma, thyroid carcinoma and renal carcinoma.

4. The method according to claim 1, wherein the peptide is administered in combination with an adjuvant that enhances production of, or comprises, IL-15, IL-12 and/or IL-18.

5. The method according to claim 1, wherein the peptide is administered in combination with a check point inhibitor.

6. The method according to claim 5, wherein the peptide is administered in combination with an inhibitor of a receptor selected from the group consisting of LILRB1, inhibitory KIRs, NKG2A, PD-1, CTLA-4, TIM-3, TIGIT and LAG-3.

7. The method according to claim 1, wherein the peptide is administered by a vector comprising or encoding the peptide according to claim 1, wherein the peptide is encoded by a nucleic acid molecule operably linked to a promoter for expression in mammalian subjects.

8. The method according to claim 7, wherein the vector is a genetically modified virus selected from the group consisting of attenuated HCMV, vaccinia virus, adenovirus, adeno-associated virus, retrovirus, and lentivirus.

9. The method according to claim 1, the method comprising administering to said subject an effective amount of a genetically engineered virus encoding a peptide comprising or consisting of a polypeptide according to claim 1.

10. An in vitro method for cultivating and/or expanding NKG2C+ natural killer (NK) cells, said method comprising:
    providing leukocyte cells from a donor, wherein said leukocytes comprise NK cells;
    contacting said NK cells with a peptide comprising the amino acid sequence according to SEQ ID NO: 2; and
    optionally isolating or enriching for NKG2C+ NK cells.

11. An isolated population of NKG2C+ natural killer (NK) cells produced by the method according to claim 10.

12. A method of treating a subject having or being at risk of developing a medical condition associated with pathogenic cells expressing HLA-E and a peptide comprising an amino acid sequence according to SEQ ID NO; 1, comprising administering to said subject an effective amount of an isolated population of NKG2C+ natural killer (NK) cells according to claim 11.

13. The method according to claim 12, wherein the medical condition is a cancer associated with expression of HLA-G and HLA-E.

* * * * *

UNITED STATES PATENT AND TRADEMARK OFFICE
CERTIFICATE OF CORRECTION

PATENT NO. : 10,864,245 B2
APPLICATION NO. : 16/355577
DATED : December 15, 2020
INVENTOR(S) : Chiara Romagnani It is certified that error appears in the above-identified patent and that said Letters Patent is hereby corrected as shown below:

On the Title Page

On Page 2, Column 1, Item (56), Line 35, under Other Publications, delete "lb" and insert --Ib--.

On Page 2, Column 1, Item (56), Line 47, under Other Publications, delete "Edependent" and insert --E dependent--.

On Page 2, Column 2, Item (56), Line 60, under Other Publications, delete "Cytomegalovirusinfected" and insert --Cytomegalovirus-infected--.

On Page 2, Column 2, Item (56), Line 61, under Other Publications, delete "D K" and insert --Dk--.

On Page 2, Column 2, Item (56), Line 61, under Other Publications, delete "Cmvencoded" and insert --Cmv-encoded--.

On Page 3, Column 1, Item (56), Line 50, under Other Publications, delete "Ff" and insert --Of--.

On Page 3, Column 1, Item (56), Line 51, under Other Publications, delete "Cytomegalovirusderived" and insert --Cytomegalovirus-derived--.

On Page 3, Column 2, Item (56), Line 56, under Other Publications, delete "_C" and insert -- -C--.

In the Specification

In Column 5, Line 49, delete "NO2" and insert --NO: 2--.

In Column 11, Line 60, delete "FcεR1g-" and insert --FcεR1γ- --.

In Column 12, Line 2, delete "KIR2DL3+" and insert --KIR2DL3+,--.

Signed and Sealed this
Twenty-ninth Day of June, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,864,245 B2

In Column 12, Line 55, delete "(VMAPRTLXL" and insert --VMAPRTLXL--.

In Column 14, Line 41, delete "RMA-Si/" and insert --RMA-S/--.

In Column 16, Line 60, delete "FcεR1g," and insert --FcεR1γ,--.

In Column 17, Line 11, delete "NKcell" and insert --NK cell--.

In Column 17, Line 12, delete "zscores" and insert --z-scores--.

In Column 17, Line 20, delete "FcεR1g," and insert --FcεR1γ,--.

In Column 18, Line 28 (Approx.), delete "sequencesof" and insert --sequences of--.

In Column 24, Line 29, delete "by" and insert --be--.

In Column 24, Line 32, delete "NO1" and insert --NO: 1--.

In Column 24, Line 43, delete "leukemias." and insert --leukemia.--.

In Column 24, Line 57, delete "leukemias" and insert --leukemia--.

In Column 24, Line 63, delete "leukemias," and insert --leukemia,--.

In Column 24, Line 66, delete "Leukemias" and insert --Leukemia--.

In Column 25, Line 3, delete "basophylic" and insert --basophilic--.

In Column 25, Lines 24-25, delete "chorio carcinoma," and insert --choriocarcinoma,--.

In Column 25, Line 35, delete "telangiectaltic" and insert --telangiectatic--.

In Column 25, Line 41, delete "subungal" and insert --subungual--.

In Column 25, Line 51, delete "comedo carcinoma," and insert --comedocarcinoma,--.

In Column 25, Line 55, delete "epiermoid" and insert --epidermoid--.

In Column 25, Line 56, delete "adenoides," and insert --adenoids,--.

In Column 25, Lines 56-57, delete "exulcere," and insert --ex ulcere,--.

In Column 25, Lines 58-59, delete "gigantocellulare," and insert --gigantocellular,--.

In Column 26, Line 11, delete "solanoid" and insert --solenoid--.

CERTIFICATE OF CORRECTION (continued)
U.S. Pat. No. 10,864,245 B2

In Column 26, Lines 14-15, delete "telangiectaticurn," and insert --telangiectaticum,--.

In Column 26, Line 24, delete "insulanoma," and insert --insulinoma,--.

In Column 26, Line 32, delete "choloangiocellular" and insert --cholangiocellular--.

In Column 26, Line 34, delete "glioblastma" and insert --glioblastoma--.

In Column 27, Line 16, delete "monophosphryl" and insert --monophosphoryl--.

In Column 27, Line 55, delete "CXCL-8," and insert --CXCL8,--.

In Column 30, Line 14, delete "(UVNis)" and insert --(UV/Vis)--.

In Column 34, Line 5, delete "intraocularally," and insert --intraocularly,--.

In Column 38, Line 4, delete "QIAmp" and insert --QIAamp--.

In Column 38, Line 17, delete "HLA E" and insert --HLA-E--.

In Column 38, Line 61, delete "(3000)" and insert --(300 μm)--.

In Column 39, Line 10, delete "(3000)" and insert --(300 μm)--.

In Column 40, Line 29, delete "IoxP" and insert --loxP--.

In Column 40, Line 30, delete "pIC1.for" and insert --plC1 for--.

In Column 40, Line 38, delete "pIC1$^{68}$" and insert --plC1$^{68}$--.

In Column 40, Line 41, delete "pIC" and insert --plC--.

In Column 40, Line 43, delete "pIC" and insert --plC--.

In Column 42, Line 16, delete "NKG2C+" and insert --NKG2C$^+$--.

In Column 42, Line 17, delete "QIAmp" and insert --QIAamp--.

In Column 42, Line 56, delete "NKG2C+" and insert --NKG2C$^+$--.

In Column 43, Lines 19-20, delete "Graph Pad" and insert --GraphPad--.

In Column 43, Line 20, delete "(Graph Pad" and insert --(GraphPad--.

In Column 43, Line 31, delete "pre workshop:" and insert --preworkshop:--.

CERTIFICATE OF CORRECTION (continued)
U.S. Pat. No. 10,864,245 B2

In Column 43, Line 49, delete "bp" and insert --bp.--.

In Column 44, Line 15, delete "MeI," and insert --Mel,--.

In Column 44, Line 17, delete "thiopeta;" and insert --thiotepa;--.

In Column 44, Line 51 (Approx.), delete "FcεR17-" and insert --FcεR1γ- --.

In Column 45, Line 11, delete "2," and insert --2),--.

In Column 45, Line 31, delete "algorithm 32" and insert --algorithm[32]--.

In Column 48, Line 49, delete "LAGS," and insert --LAG3,--.

In Column 48, Line 51, delete "110," and insert --IL10,--.

In Column 49, Line 47, delete "ist" and insert --1st--.

In Column 50, Line 62, delete "KIR2DS1$^+$" and insert --KIR2DS1+--.

In Column 51, Line 3, delete "co-stimulation53." and insert --co-stimulation[53].--.

In Column 51, Line 48, delete "coexpressing" and insert --co-expressing--.

In Column 51, Line 57, delete "HLA G" and insert --HLA-G--.

In Columns 55-56, Line 7 (Approx.), delete "FceR1g" and insert --FcεR1γ--.

In Columns 57-58, Line 7 (Approx.), delete "FceR1g" and insert --FcεR1γ--.

In Columns 59-60, Line 19 (Approx.), delete "BioLegend)" and insert --BioLegend--.

In Columns 59-60, Line 24 (Approx.), delete "Catv130" and insert --Cat#130--.

In Columns 61-62, Line 8 (Approx.), delete "pIC1.for" and insert --plC1.for--.

In Columns 61-62, Line 11 (Approx.), delete "pIC.rev" and insert --plC.rev--.

In Column 63, Line 2, delete "1b" and insert --Ib--.

In the Claims

In Column 89, Line 22, Claim 1, delete "NO:2" and insert --NO: 2--.

In Column 90, Line 41, Claim 12, delete "NO;" and insert --NO:--.